US011732249B2

(12) United States Patent
Kornfeld et al.

(10) Patent No.: US 11,732,249 B2
(45) Date of Patent: *Aug. 22, 2023

(54) COMPOSITIONS COMPRISING A MODIFIED GICNAC-1-PHOSPHOTRANSFERASE AND METHODS OF USE THEREOF

(71) Applicant: Washington University, St. Louis, MO (US)

(72) Inventors: Stuart Kornfeld, St. Louis, MO (US); Lin Liu, St. Louis, MO (US); Wang Lee, St. Louis, MO (US); Balraj Doray, St. Louis, MO (US)

(73) Assignee: Washington University, St. Louis, MO (US)

( * ) Notice: Subject to any disclaimer, the term of this patent is extended or adjusted under 35 U.S.C. 154(b) by 221 days.

This patent is subject to a terminal disclaimer.

(21) Appl. No.: 17/125,480

(22) Filed: Dec. 17, 2020

(65) Prior Publication Data

US 2021/0180035 A1 Jun. 17, 2021

Related U.S. Application Data

(63) Continuation of application No. 16/338,347, filed as application No. PCT/US2017/054755 on Oct. 2, 2017, now Pat. No. 10,907,139.

(60) Provisional application No. 62/402,468, filed on Sep. 30, 2016.

(51) Int. Cl.
| C12N 9/10 | (2006.01) |
| C12N 9/12 | (2006.01) |
| C12N 9/24 | (2006.01) |
| A61K 38/04 | (2006.01) |

(52) U.S. Cl.
CPC ......... *C12N 9/1288* (2013.01); *C12N 9/2402* (2013.01); *C12Y 207/08017* (2013.01)

(58) Field of Classification Search
CPC .................................. C12N 9/12; C12N 9/24
See application file for complete search history.

(56) References Cited

U.S. PATENT DOCUMENTS

| 10,907,139 | B2 | 2/2021 | Kornfeld et al. |
| 2003/0119088 | A1 | 6/2003 | Canfield et al. |
| 2014/0018338 | A1 | 1/2014 | Chandran et al. |
| 2019/0225953 | A1 | 7/2019 | Kornfeld et al. |

FOREIGN PATENT DOCUMENTS

WO 2018064667 A1 4/2018

OTHER PUBLICATIONS

GenBank EAW97684.1 entitled N-acetylglucosamine-1-phosphate transferase, alpha and beta subunits, isoform CRA_c [*Homo sapiens*], Mar. 23, 2015; 2 pgs.
Office Action dated Jul. 13, 2021 from related Japanese Patent Application No. 2019-538575; with English translation, 13 pgs.
Decision to Grant dated Jan. 27, 2022 from related South Korean Patent Application No. 62021024349.4; 3 pgs, with partial English translation.
Office Action dated Feb. 14, 2022 from related Canadian Patent Application No. 3,038,598; 4 pgs.
Altschul, S. et al., "Basic Local Alignment Search Tool," J. Mo. Biol., 1990, pp. 403-410, vol. 215, Academic Press Limited.
Altschul, S. et al., "Gapped BLAST and PSI-BLAST: a new generation of protein database search programs," Nucl. Acid Res., 1997, pp. 3389-3402, vol. 25, No. 17, Oxford University Press.
Bao, M. et al., "Bovine UDP-N-acetylglucosamine:Lysosomal-enzyme N-acetylglucosamine-1-phosphotransferase," J. Biol. Chem., Dec. 6, 1996, pp. 31437-31445, vol. 271, No. 49.
Barton, N. et al., "Replacement Therapy for Inherited Enzyme Deficiency—Macrophage-Targed Glucocerebrosidase for Gaucher's Disease," N. Engl. J. Med., May 23, 1991, pp. 1464-1470, vol. 324, No. 21.
Blanchard, F. et al., "The Mannose 6-Phosphate/Insulin-like Growth Factor II Receptor Is a Nanomolar Affinity Receptor for Glycosylated Human Leukemia Inhibitory Factor," J. Biol. Chem., Aug. 14, 1998, pp. 20886-20893, vol. 273, No. 33.
De Pace, R. et al., "Subunit interactions of the disease-related hexameric GlcNAc-1-phosphotransferase complex," Human Mol. Genet., 2015, pp. 6826-6835, vol. 24, No. 23.
Dustin, M. et al., "A Novel Mutagenesis Strategy Identifies Distantly Spaced Amino Acid Sequences That Are Required for the Phosphorylation of Both the Oligosaccharides of Procathepsin D by N-Acetylglucosamine 1-Phosphotransferase," J. Biol. Chem., Jan. 6, 1995, pp. 170-179, vol. 270, No. 1.
EBI Accession No. EMBL: EAW97684, Jul. 30, 2005; 3 pgs.
Elagoz, A. et al., "Biosynthesis and Cellular Trafficking of the Convertase SKI-1/S1P," J. Biol. Chem., Mar. 29, 2002, pp. 11265-11275, vol. 277, No. 13.
Extended European Search Report dated Mar. 13, 2020 from related European Patent Application No. 17857616.1; 10 pgs.
Faust, P. et al., "Renin, a Secretory Glycoprotein, Acquires Phosphomannosyl Residues," J. Cell Biol., Nov. 1987, pp. 1947-1955, vol. 105, No. 5, The Rockefeller University Press.
Gabel, C. et al., "Lysosomal Enzyme Trafficking in Mannose 6-Phosphate Receptor-positive Mouse L-Cells: Demonstration of a Steady State Accumulation of Phosphorylated Acid Hydrolases," J. Cell Biol., 1986, pp. 943-950, vol. 102, No. 3, The Rockefeller University Press.
Hay, B. et al., "Aminopyrrolidineamide inhibitors of site-1 protease," Bioorg. Med. Chem. Lett., Aug. 15, 2007, pp. 4411-4414, vol. 17, No. 16.
International Search Report and Written Opinion dated Mar. 5, 2018 from related Patent Application No. PCT/US2017/054755; 13 pgs.
Karlin, S. et al., "Methods for assessing the statistical significance of molecular sequence features by using general scoring schemes," PNAS, Mar. 1990, 2264-2268, vol. 87.

(Continued)

*Primary Examiner* — Maryam Monshipouri
(74) *Attorney, Agent, or Firm* — Polsinelli PC

(57) ABSTRACT

The disclosure provides a modified UDP-GlcNAc:Lysosomal Enzyme GlcNAc phosphotransferase with enhanced ability to phosphorylate lysosomal enzymes and methods of use thereof.

8 Claims, 31 Drawing Sheets
(17 of 31 Drawing Sheet(s) Filed in Color)
Specification includes a Sequence Listing.

(56) References Cited

OTHER PUBLICATIONS

Kornfeld, S., "Trafficking of Lysosomal Enzymes in Normal and Disease States," J. Clin. Invest., Jan. 1986, pp. 1-6, vol. 77.

Kudo, M. et al., "The alpha- and beta-subunits of the Human UDP-N-acetylglucosamine: Lysosomal Enzyme Phosphotransferase Are Encoded by a Single cDNA," J. Biol. Chem., Oct. 28, 2005, pp. 36141-36149, vol. 280, No. 43.

Lachmann, R., "Enzyme replacement therapy for lysosomal storage diseases," Curr. Opin. Pediatr., Dec. 1, 2011, pp. 588-593, vol. 23, No. 6, Lippincott Williams & Wilkins.

Lang, L. et al., "Lysosomal Enzyme Phosphorylation," J. Biol. Chem., Dec. 10, 1984, pp. 14663-14671, vol. 259, No. 23.

Liu, L. et al., "Role of spacer-1 in the maturation and function of GlcNAc-1-phosphotransferase," FEBS Lett., 2017, pp. 47-55, vol. 591.

Liu, L. et al., "Engineering of GlcNAc-1-Phosphotransferase for Production of Highly Phosphorylated Lysosomal Enzymes for Enzyme Replacement Therapy," Mol. Ther. Methods Clin. Develop., Jun. 2017, pp. 59-65, vol. 5.

Marschner, K. et al., "A Key Enzyme in the Biogenesis of Lysosomes Is a Protease That Regulates Cholesterol Metabolism," Sci., Jul. 1, 2011, pp. 87-90, vol. 333.

Mcvie-Wylie, A. et al., "Biochemical and pharmacological characterization of different recombinant acid alpha-glucosidase preparations evaluated for the treatment of Pompe disease," NIH Public Access Author Manuscript, Nov. 8, 2009, pp. 1-18, published in final edited form as: Mol. Genet. Metab., Aug. 2008, pp. 448-455, vol. 94, No. 4.

Mishikawa, A. et al., "Identification of Amino Acids That Modulate Mannose Phosphorylation of Mouse DNase I, a Secretory Glycoprotein," J. Biol. Chem., Jul. 2, 1999, pp. 19309-19315, vol. 274, No. 27.

Notice of Allowance dated Nov. 30, 2020 from related Korean Patent Application No. 10-2019-7010267, with English translation, 3 pgs.

Office Action dated Feb. 14, 2020 from related Korean Patent Application No. 10-2019-7010267, with English translation, 11 pgs.

Qian, Y. et al., "Functions of the alpha, beta, and gamma Subunits of UDP-GlcNAc:Lysosomal Enzyme N-Acetylglucosamine-1-Phosphotransferase," J. Biol. Chem., Jan. 29, 2010, pp. 3360-3370, vol. 285, No. 5.

Qian, Y. et al., "The DMAP interaction domain of UDP-GlcNAc:lysosomal enzyme N-acetylglucosamine-1-phosphotransferase is a substrate recognition module," PNAS, Jun. 18, 2013, pp. 10246-10251, vol. 110, No. 25.

Qian, Y. et al., "Analysis of Mucolipidosis III/II GNPTAB Missense Mutations Identifies Domains of UDP-GlcNAc: lysosomal Enzyme GlcNAc-1-phosphotransferase Involved in Catalytic Function and Lysosomal Enzyme Recognition," J. Biol. Chem., Jan. 30, 2015, pp. 3045-3056, vol. 290, No. 5.

Reitman, M. et al., "Lysosomal Enzyme Targeting," J. Biol. Chem., Dec. 10, 1981, pp. 11977-11980, vol. 256, No. 23.

Roces, D. et al., "Efficacy of enzyme replacement therapy in alpha-mannosidosis mice: a preclinical animal study," Hum. Mol. Genet., 2004, pp. 1979-1988, vol. 13, No. 18.

Serrano, P. et al., "NMR structure of the 140-315 fragment of the N-acetylglucosamine-1-phosphate transferase, alpha and beta subunits," RCSB Protein Data Bank, Aug. 19, 2015, available at: http://www.rcsb.org/pdb/explore/explore.do?structureId=2N6D; 3 pgs.

Sleat, D. et al., "Identification of Sites of Mannose 6-Phosphorylation on Lysosomal Proteins," Mol. Cell. Proteomics, 2006, pp. 686-701, vol. 5, No. 4.

Sleat, D. et al., "Extending the Mannose 6-Phosphate Glycoproteome by High Resolution/Accuracy Mass Spectrometry Analysis of Control and Acid Phosphatase 5-Deficient Mice," Mol. Cell. Proteomics, 2013, pp. 1806-1817, vol. 12.

Sperisen, P. et al., "Stealth Proteins: In Silico Identification of a Novel Protein Family Rendering Bacterial Pathogens Invisible to Host Immune Defense," PLoS Comput. Biol., Nov. 2005, pp. 0492-0499, vol. 1, No. 6, e63.

Steet, R. et al., "Identification of the Minimal Lysosomal Enzyme Recognition Domain in Cathepsin D," J. Biol. Chem., Sep. 30, 2005, pp. 33318-33323, vol. 280, No. 39.

Tong, P. et al., "Ligand Interactions of the Cation-independent Mannose 6-Phosphate Receptor," J. Biol. Chem., May 15, 1989, pp. 7962-7969, vol. 264, No. 14.

Valenzano, K. et al., "Soluble Insulin-like Growth Factor II/Mannose 6-Phosphate Receptor Carries Multiple High Molecular Weight Forms of Insulin-like Growth Factor II in Fetal Bovine Serum," J. Biol. Chem., Jul. 7, 1995, pp. 16441-16448, vol. 270, No. 27.

Van Meel, E. et al., "Multiple Domains of GlcNAc-1-phosphotransferase Mediate Recognition of Lysosomal Enzymes," J. Biol. Chem., Apr. 8, 2016, pp. 8295-8307, vol. 291, No. 15.

Velho, R. et al., "Analyses of disease-related GNPTAB mutations define a novel GlcNAc-1-phosphotransferase interaction domain and an alternative site-1 protease cleavage site," Hum. Mol. Genet., 2015, pp. 3497-3505, vol. 24, No. 12, Oxford University Press.

Weinreb, N. et al., "Long-term clinical outcomes in type 1 Gaucher disease following 10 years of imiglucerase treatment," J. Inherit. Metab. Dis., 2013, pp. 543-553, vol. 36, No. 3, Springer.

Auton, Destabilization of the A1 Domain in von Willebrand Factor Dissociates the A1A2A3 Tri-domain and Provokes Spontaneous Binding to Glycoprotein Iba and Platelet Activation under Shear Stress, The Journal of Biological Chemistry, Jul. 23, 2010, vol. 285, No. 30, pp. 22831-22839.

Yuan, The unfolded von Willebrand factor response in bloodstream: the self-association perspective, Journal of Hematology & Oncology, 2012, vol. 5:65, 10 pgs.

UniProt Reference Sequence P04275 "A1A2A3 VWF Human" Mar. 20, 1987, 24 pgs.

| Precursor | Cleavage site sequence | | | | | | | |
|---|---|---|---|---|---|---|---|---|
| | -6 | -5 | -4 | -3 | -2 | -1 | 1 | 2 |
| Pro-BDNF | G | S | R | G | L | T | S | L |
| ATF6 | Q | R | R | H | L | L | G | F |
| SREBP-1a | P | G | R | N | V | L | G | T |
| ProS1P site B | V | F | R | S | L | K | Y | A |
| GNPTAB-928 | T | G | R | Q | L | K | D | T |
| GNPTAB-882 | L | G | R | K | L | Q | H | Y |

SEQUENCE LISTING

```
<160> NUMBER OF SEQ ID NOS: 7

<210> SEQ ID NO 1
<211> LENGTH: 1256
<212> TYPE: PRT
<213> ORGANISM: Homo sapiens

<400> SEQUENCE: 1

Met Leu Phe Lys Leu Leu Gln Arg Gln Thr Tyr Thr Cys Leu Ser His
1               5                   10                  15

Arg Tyr Gly Leu Tyr Val Cys Phe Leu Gly Val Val Val Thr Ile Val
                20                  25                  30

Ser Ala Phe Gln Phe Gly Glu Val Val Leu Glu Trp Ser Arg Asp Gln
            35                  40                  45

Tyr His Val Leu Phe Asp Ser Tyr Arg Asp Asn Ile Ala Gly Lys Ser
        50                  55                  60

Phe Gln Asn Arg Leu Cys Leu Pro Met Pro Ile Asp Val Val Tyr Thr
65                  70                  75                  80

Trp Val Asn Gly Thr Asp Leu Glu Leu Leu Lys Glu Leu Gln Gln Val
                85                  90                  95

Arg Glu Gln Met Glu Glu Glu Lys Ala Met Arg Glu Ile Leu Gly
                100                 105                 110
```

```
Lys Asn Thr Thr Glu Pro Thr Lys Lys Ser Glu Lys Gln Leu Glu Cys
            115                 120                 125

Leu Leu Thr His Cys Ile Lys Val Pro Met Leu Val Leu Asp Pro Ala
130                 135                 140

Leu Pro Ala Asn Ile Thr Leu Lys Asp Leu Pro Ser Leu Tyr Pro Ser
145                 150                 155                 160

Phe His Ser Ala Ser Asp Ile Phe Asn Val Ala Lys Pro Lys Asn Pro
                165                 170                 175

Ser Thr Asn Val Ser Val Val Phe Asp Ser Thr Lys Asp Val Glu
            180                 185                 190

Asp Ala His Ser Gly Leu Leu Lys Gly Asn Ser Arg Gln Thr Val Trp
        195                 200                 205

Arg Gly Tyr Leu Thr Thr Asp Lys Glu Val Pro Gly Leu Val Leu Met
    210                 215                 220

Gln Asp Leu Ala Phe Leu Ser Gly Phe Pro Pro Thr Phe Lys Glu Thr
225                 230                 235                 240

Asn Gln Leu Lys Thr Lys Leu Pro Glu Asn Leu Ser Ser Lys Val Lys
                245                 250                 255

Leu Leu Gln Leu Tyr Ser Glu Ala Ser Val Ala Leu Leu Lys Leu Asn
            260                 265                 270

Asn Pro Lys Asp Phe Gln Glu Leu Asn Lys Gln Thr Lys Lys Asn Met
        275                 280                 285

Thr Ile Asp Gly Lys Glu Leu Thr Ile Ser Pro Ala Tyr Leu Leu Trp
    290                 295                 300

Asp Leu Ser Ala Ile Ser Gln Ser Lys Gln Asp Glu Asp Ile Ser Ala
305                 310                 315                 320

Ser Arg Phe Glu Asp Asn Glu Glu Leu Arg Tyr Ser Leu Arg Ser Ile
                325                 330                 335

Glu Arg His Ala Pro Trp Val Arg Asn Ile Phe Ile Val Thr Asn Gly
            340                 345                 350

Gln Ile Pro Ser Trp Leu Asn Leu Asp Asn Pro Arg Val Thr Ile Val
        355                 360                 365

Thr His Gln Asp Val Phe Arg Asn Leu Ser His Leu Pro Thr Phe Ser
    370                 375                 380

Ser Pro Ala Ile Glu Ser His Ile His Arg Ile Glu Gly Leu Ser Gln
385                 390                 395                 400

Lys Phe Ile Tyr Leu Asn Asp Asp Val Met Phe Gly Lys Asp Val Trp
                405                 410                 415

Pro Asp Asp Phe Tyr Ser His Ser Lys Gly Gln Lys Val Tyr Leu Thr
            420                 425                 430

Trp Pro Val Pro Asn Cys Ala Glu Gly Cys Pro Gly Ser Trp Ile Lys
        435                 440                 445

Asp Gly Tyr Cys Asp Lys Ala Cys Asn Asn Ser Ala Cys Asp Trp Asp
    450                 455                 460

Gly Gly Asp Cys Ser Gly Asn Ser Gly Gly Ser Arg Tyr Ile Ala Gly
465                 470                 475                 480

Gly Gly Gly Thr Gly Ser Ile Gly Val Gly Gln Pro Trp Gln Phe Gly
                485                 490                 495

Gly Gly Ile Asn Ser Val Ser Tyr Cys Asn Gln Gly Cys Ala Asn Ser
            500                 505                 510

Trp Leu Ala Asp Lys Phe Cys Asp Gln Ala Cys Asn Val Leu Ser Cys
        515                 520                 525

Gly Phe Asp Ala Gly Asp Cys Gly Gln Asp His Phe His Glu Leu Tyr
```

```
            530               535               540
Lys Val Ile Leu Leu Pro Asn Gln Thr His Tyr Ile Pro Lys Gly
545                 550               555               560

Glu Cys Leu Pro Tyr Phe Ser Phe Ala Glu Val Ala Lys Arg Gly Val
                    565               570               575

Glu Gly Ala Tyr Ser Asp Asn Pro Ile Ile Arg His Ala Ser Ile Ala
                580               585               590

Asn Lys Trp Lys Thr Ile His Leu Ile Met His Ser Gly Met Asn Ala
            595               600               605

Thr Thr Ile His Phe Asn Leu Thr Phe Gln Asn Thr Asn Asp Glu Glu
        610               615               620

Phe Lys Met Gln Ile Thr Val Glu Val Asp Thr Arg Glu Gly Pro Lys
625               630               635               640

Leu Asn Ser Thr Ala Gln Lys Gly Tyr Glu Asn Leu Val Ser Pro Ile
                645               650               655

Thr Leu Leu Pro Glu Ala Glu Ile Leu Phe Glu Asp Ile Pro Lys Glu
                660               665               670

Lys Arg Phe Pro Lys Phe Lys Arg His Asp Val Asn Ser Thr Arg Arg
            675               680               685

Ala Gln Glu Glu Val Lys Ile Pro Leu Val Asn Ile Ser Leu Leu Pro
        690               695               700

Lys Asp Ala Gln Leu Ser Leu Asn Thr Leu Asp Leu Gln Leu Glu His
705               710               715               720

Gly Asp Ile Thr Leu Lys Gly Tyr Asn Leu Ser Lys Ser Ala Leu Leu
                725               730               735

Arg Ser Phe Leu Met Asn Ser Gln His Ala Lys Ile Lys Asn Gln Ala
            740               745               750

Ile Ile Thr Asp Glu Thr Asn Asp Ser Leu Val Ala Pro Gln Glu Lys
        755               760               765

Gln Val His Lys Ser Ile Leu Pro Asn Ser Leu Gly Val Ser Glu Arg
    770               775               780

Leu Gln Arg Leu Thr Phe Pro Ala Val Ser Val Lys Val Asn Gly His
785               790               795               800

Asp Gln Gly Gln Asn Pro Pro Leu Asp Leu Glu Thr Thr Ala Arg Phe
                805               810               815

Arg Val Glu Thr His Thr Gln Lys Thr Ile Gly Gly Asn Val Thr Lys
            820               825               830

Glu Lys Pro Pro Ser Leu Ile Val Pro Leu Glu Ser Gln Met Thr Lys
            835               840               845

Glu Lys Lys Ile Thr Gly Lys Glu Lys Glu Asn Ser Arg Met Glu Glu
        850               855               860

Asn Ala Glu Asn His Ile Gly Val Thr Glu Val Leu Leu Gly Arg Lys
865               870               875               880

Leu Gln His Tyr Thr Asp Ser Tyr Leu Gly Phe Leu Pro Trp Glu Lys
                885               890               895

Lys Lys Tyr Phe Gln Asp Leu Leu Asp Glu Glu Ser Leu Lys Thr
            900               905               910

Gln Leu Ala Tyr Phe Thr Asp Ser Lys Asn Thr Gly Arg Gln Leu Lys
        915               920               925

Asp Thr Phe Ala Asp Ser Leu Arg Tyr Val Asn Lys Ile Leu Asn Ser
    930               935               940

Lys Phe Gly Phe Thr Ser Arg Lys Val Pro Ala His Met Pro His Met
945               950               955               960
```

-continued

```
Ile Asp Arg Ile Val Met Gln Glu Leu Gln Asp Met Phe Pro Glu Glu
                965                 970                 975

Phe Asp Lys Thr Ser Phe His Lys Val Arg His Ser Glu Asp Met Gln
                980                 985                 990

Phe Ala Phe Ser Tyr Phe Tyr Tyr Leu Met Ser Ala Val Gln Pro Leu
            995                1000                1005

Asn Ile Ser Gln Val Phe Asp Glu Val Asp Thr Asp Gln Ser Gly
        1010                1015                1020

Val Leu Ser Asp Arg Glu Ile Arg Thr Leu Ala Thr Arg Ile His
        1025                1030                1035

Glu Leu Pro Leu Ser Leu Gln Asp Leu Thr Gly Leu Glu His Met
        1040                1045                1050

Leu Ile Asn Cys Ser Lys Met Leu Pro Ala Asp Ile Thr Gln Leu
        1055                1060                1065

Asn Asn Ile Pro Pro Thr Gln Glu Ser Tyr Tyr Asp Pro Asn Leu
        1070                1075                1080

Pro Pro Val Thr Lys Ser Leu Val Thr Asn Cys Lys Pro Val Thr
        1085                1090                1095

Asp Lys Ile His Lys Ala Tyr Lys Asp Lys Asn Lys Tyr Arg Phe
        1100                1105                1110

Glu Ile Met Gly Glu Glu Ile Ala Phe Lys Met Ile Arg Thr
        1115                1120                1125

Asn Val Ser His Val Val Gly Gln Leu Asp Asp Ile Arg Lys Asn
        1130                1135                1140

Pro Arg Lys Phe Val Cys Leu Asn Asp Asn Ile Asp His Asn His
        1145                1150                1155

Lys Asp Ala Gln Thr Val Lys Ala Val Leu Arg Asp Phe Tyr Glu
        1160                1165                1170

Ser Met Phe Pro Ile Pro Ser Gln Phe Glu Leu Pro Arg Glu Tyr
        1175                1180                1185

Arg Asn Arg Phe Leu His Met His Glu Leu Gln Glu Trp Arg Ala
        1190                1195                1200

Tyr Arg Asp Lys Leu Lys Phe Trp Thr His Cys Val Leu Ala Thr
        1205                1210                1215

Leu Ile Met Phe Thr Ile Phe Ser Phe Phe Ala Glu Gln Leu Ile
        1220                1225                1230

Ala Leu Lys Arg Lys Ile Phe Pro Arg Arg Ile His Lys Glu
        1235                1240                1245

Ala Ser Pro Asn Arg Ile Arg Val
        1250                1255

<210> SEQ ID NO 2
<211> LENGTH: 8
<212> TYPE: PRT
<213> ORGANISM: Artificial Sequence
<220> FEATURE:
<223> OTHER INFORMATION: Synthesized

<400> SEQUENCE: 2

Gly Ser Arg Gly Leu Thr Ser Leu
1               5

<210> SEQ ID NO 3
<211> LENGTH: 8
<212> TYPE: PRT
<213> ORGANISM: Artificial Sequence
```

```
<220> FEATURE:
<223> OTHER INFORMATION: Synthesized

<400> SEQUENCE: 3

Gln Arg Arg His Leu Leu Gly Phe
1               5

<210> SEQ ID NO 4
<211> LENGTH: 8
<212> TYPE: PRT
<213> ORGANISM: Artificial Sequence
<220> FEATURE:
<223> OTHER INFORMATION: Synthesized

<400> SEQUENCE: 4

Pro Gly Arg Asn Val Leu Gly Thr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthesized

<400> SEQUENCE: 5

Val Phe Arg Ser Leu Lys Tyr Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Synthesized

<400> SEQUENCE: 6

Thr Gly Arg Gln Leu Lys Asp Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Synthesized

<400> SEQUENCE: 7

Leu Gly Arg Lys Leu Gln His Tyr
1               5
```

COMPOSITIONS COMPRISING A MODIFIED GICNAC-1-PHOSPHOTRANSFERASE AND METHODS OF USE THEREOF

CROSS REFERENCE TO RELATED APPLICATIONS

This application claims the benefit of U.S. Provisional Application No. 62/402,468, filed Sep. 30, 2016 the disclosure of which is hereby incorporated by reference in its entirety.

GOVERNMENTAL RIGHTS

This invention was made with government support under CA 008759 awarded by the National Institutes of Health (NIH). The government has certain rights in the invention.

FIELD OF THE INVENTION

The disclosure provides a modified UDP-GlcNAc:Lysosomal Enzyme GlcNAc-1-phosphotransferase with enhanced ability to phosphorylate lysosomal enzymes and methods of use thereof.

BACKGROUND OF THE INVENTION

Enzyme Replacement Therapy (ERT) is currently the major form of treatment for a number of lysosomal storage diseases, although its efficacy varies among the individual disorders. Most of these inherited disorders arise from the lack of activity of a single lysosomal enzyme which leads to the accumulation of the material normally degraded by the enzyme. The buildup of the storage material in the lysosome eventually results in cell and organ dysfunction. The goal of ERT is to introduce sufficient amounts of normal enzyme into the lysosomes of the defective cells to clear the storage material and restore lysosome function. This form of therapy was first used in patients with Type 1 Gaucher disease who lack acid β-glucocebrosidase activity and accumulate glucosylceramide primarily in macrophage type cells. The replacement enzyme, containing N-linked glycans with terminal mannose residues, is infused intravenously and taken up by macrophages via cell surface mannose receptors. The endocytosed enzyme is then transported via endosomes to lysosomes where it functions with good clinical results in this disorder.

Since most cell types lack mannose receptors, the replacement enzymes used to treat lysosomal storage disorders that involve cell types other than macrophages utilize binding to mannose 6-phosphate (Man-6-P) receptors at the cell surface for subsequent delivery to lysosomes. These enzymes are purified from the secretions of mammalian cells, mostly Chinese Hamster Ovary cells, engineered to produce high levels of the enzyme of interest. This approach is dependent upon the ability of the endogenous GlcNAc-1-phosphotransferase to phosphorylate mannose residues of the N-glycans of the expressed lysosomal enzyme. Some of the replacement enzymes produced by this technique are highly phosphorylated and bind well to the Man-6-P receptors. Others, however, are poorly phosphorylated, limiting their effectiveness in ERT. This includes the Pompe disease enzyme (acid α-glucosidase, GAA) and the alpha-mannosidosis enzyme (lysosomal acid α-mannosidase, LAMAN).

Thus, there is a need in the art for improved methods of enzyme replacement therapy and improved enzyme production.

SUMMARY OF THE INVENTION

In an aspect, the disclosure provides a modified GlcNAc-1-phosphotransferase (GlcNAc-1-PT) α/β subunit comprising internal deletion of amino acids with reference to full-length human GlcNAc-1-PT α/β subunit of SEQ ID NO:1. The full-length GlcNAc-1-PT α/β includes a spacer-1 domain (spacer-1), a Notch 1 domain (Notch 1), a Notch 2 domain (Notch 2), a spacer-2 domain (spacer-2), a DNA methyltransferase-associated protein interaction domain (DMAP), a spacer-3 domain (spacer-3), a α/β subunit cleavage site, and a spacer-4 domain (spacer-4), arranged from the N- to C-terminus of the polypeptide. In the modified GlcNAc-1-PT α/β subunit, the spacer-1 is internally deleted. In addition, the region between the Notch-1 and α/β subunit cleavage site may also be deleted.

In another aspect, the disclosure provides a vector comprising the polynucleotide of a modified GlcNAc-1-PT α/β subunit, in which the spacer-1, or spacer-1 and region between the Notch-1 and α/β subunit cleavage site is deleted.

In an aspect, the disclosure provides a host cell that includes a vector comprising the polynucleotide of a modified GlcNAc-1-PT α/β subunit, in which the spacer-1, or spacer-1 and region between the Notch-1 and α/β subunit cleavage site are deleted.

In an aspect, the disclosure provides a method to increase oligosaccharide phosphorylation of a protein of interest, such as β-glucocebrosidase (GBA), GalA, Cathepsin D (CathD), Niemann-Pick disease type C2 (NPC2), β-hexosaminidase (HEXB), α-Galactosidase (GLA), β-Mannosidase (MANBA), alpha-L-idurnoidase, iduronate sulfatase, arylsulfatase B, acid α-glucosidase (GAA), or lysosomal acid α-mannosidase (LAMAN), by expressing an exogenous GlcNAc-1-PT α/β subunit in a cell.

In an aspect, the disclosure provides method to increase binding of a protein of interest to cell surface mannose 6-phosphate (Man-6-P) receptors (Man-6-P), by expressing a modified GlcNAc-1-PT α/β subunit in a cell.

In an aspect, the disclosure provides method of enhancing phosphorylation of lysosomal enzymes, by co-expressing a modified GlcNAc-1-PT α/β with a lysosomal enzyme of interest such as GBA, GalA, CathD, NPC2, HEXB, GLA, MANBA, alpha-L-idurnoidase, iduronate sulfatase, arylsulfatase B, GAA, or LAMAN in a cell.

BRIEF DESCRIPTION OF THE FIGURES

The application file contains at least one drawing executed in color. Copies of this patent application publication with color drawing(s) will be provided by the Office upon request and payment of the necessary fee.

FIG. 1A, FIG. 1B, FIG. 1C, FIG. 1D, FIG. 1E, FIG. 1F and FIG. 1G depict a schematic, alignment, immunoblots and graphs showing that the spacer-1 domain regulates the site of cleavage of the α/β precursor. (FIG. 1A) Schematic of GlcNAc-1-PT α/β subunit modular arrangement and replacement of the human spacer-1 sequence with *D. discoideum* spacer-1. (FIG. 1B) Immunoblot analysis of WT α/β versus the DS1 deletion mutant expressed in GNPTAB$^{-/-}$ HeLa cells probed with anti-V5 antibody. (FIG. 1C) Phosphotransferase activity toward the simple sugar αMM, using extracts of GNPTAB$^{-/-}$ cells transfected with vector, WT α/β precursor or the various mutant cDNAs. Activity was normalized to total protein concentration. (FIG. 1D) Inhibition of S1P activity of GNPTAB$^{-/-}$ HeLa cells transfected with either WT α/β precursor or the DS1 mutant cDNA. 24 h post-transfection, PF-429242 was added to the cells at a final concentration of 10 μM and cells were incubated for a further 24 h before being harvested. Cell extracts were prepared and 20 μg of each lysate was separated by SDS-PAGE and subject to western blotting. (FIG. 1E) Amino acid alignment of the two GlcNAc-1-PT a subunit S1P substrate sites with other known S1P sites. The shaded box shows the conserved consensus cleavage motif (SEQ ID NOs 2-7). (FIG. 1F) Immunoblot analysis of the point mutants, R925A, R879A, and R925A/R879A in the context of either WT α/β or the DS1 deletion mutant. Proteins expressed in GNPTAB$^{-/-}$ HeLa cells were separated by SDS-PAGE gel, transferred to nitrocellulose and probed with anti-V5 antibody. (FIG. 1G) Transfection of GNPTAB$^{-/-}$ HeLa cells with either WT α/β or the various mutants shown in FIG. 1F to determine enzyme phosphorylation as determined by binding of three endogenous lysosomal enzymes to CI-MPR-affinity beads. Bound material was assayed for activity and values obtained with cells transfected with WT α/β are set to 100%.

(FIG. 2A) Mannose phosphorylation of total soluble proteins was determined by transfecting GNPTAB$^{-/-}$ HeLa cells with either vector alone, WT α/β precursor or the DS1 mutant cDNA, followed by [2-$^3$H]mannose labeling. Values shown are calculated as the percentage of counts recovered with the CI-MPR affinity beads as a fraction of the total counts in the phosphotungstic acid precipitate. * represents $p = <0.05$. (FIG. 2B) GNPTAB$^{-/-}$ HeLa cells were co-transfected with plasmids encoding either the 3 lysosomal proteins or 4 non-lysosomal proteins along with WT α/β precursor or the DS1 mutant cDNA. Cells were labeled with [2-$^3$H]-mannose, followed by immunoprecipitation of the proteins secreted into the media and determination of the percent N-glycans containing Man-6-P. Values obtained with WT are set to 1.0. The absolute values of phosphorylation for the indicated proteins coexpressed with WT α/β precursor were: GLA, 36±3%; NPC2, 51±6% C; CathD 25±8%; DNase I, 23±4%; Renin, 21±4%; LIF, 24±7%; PoFut2, 12.6%. (FIG. 2C) Western blot of GNPTAB$^{-/-}$ HeLa cells co-transfected with the expression plasmids for the indicated proteins along with empty vector, WT α/β precursor or the DS1 mutant cDNA. Cell lysates were incubated with CI-MPR-affinity beads and the binding of the various proteins was determined by probing the blot with the following antibodies: Renin—anti-HA; NPC2, GP, Lamp1 and Lamp2 with antibodies generated against the native protein.

(FIG. 3A) Schematic of the various α/β precursor deletion constructs expressed in GNPTAB$^{-/-}$ HeLa cells. (FIG. 3B) Mannose phosphorylation of total soluble proteins was determined by transfecting GNPTAB$^{-/-}$ HeLa cells with WT α/β precursor or the indicated deletion mutant cDNAs, followed by [2-$^3$H]mannose labeling. Values shown are calculated as the percentage of counts recovered with the CI-MPR affinity beads as a fraction of the total counts in the phosphotungstic acid precipitate. The background value of 0.8±0.3% was subtracted to yield the final depicted vales. * represents $p = <0.05$ and ** represents $p = <0.01$. (FIG. 3C) Transfection of GNPTAB$^{-/-}$ HeLa cells with either WT α/β precursor, the N1-D or S1-D deletion mutant cDNAs. The degree of phosphorylation mediated WT or mutant proteins was determined by binding of three endogenous lysosomal enzymes to CI-MPR-affinity beads. Bound material was assayed for activity and values obtained with cells transfected with WT α/β are set to 100%. (FIG. 3D) Western blot of WT α/β precursor and the deletion mutants expressed in GNPTAB$^{-/-}$ HeLa cells. The indicated amount of each cell extract was loaded and the α/β precursor and β subunits were detected with an anti-V5 antibody. (FIG. 3E) Catalytic activity of WT α/β precursor and the mutants toward αMM using equal amounts of whole cell extracts. The vector-only transfected GNPTAB$^{-/-}$ HeLa cell extract served as a control and WT value was set to 100% after subtraction of vector-only background. (FIG. 3F) Immunoblot analysis of GNPTAB$^{-/-}$ HeLa cells co-transfected with the expression plasmids for the indicated proteins along with empty vector, WT α/β precursor or the indicated deletion mutant cDNAs. Cell lysates were incubated with CI-MPR-affinity beads and the binding of the various proteins was determined by probing the blots with the antibodies as described in FIG. 2C, or with anti-myc for PoFut2 and anti-Strep tag for the vWF A1A2A3 domains. (FIG. 3G) Transfection of GNPTAB$^{-/-}$ HeLa cells with either WT α/β precursor, the N1-S3 or S1-S3 deletion mutant cDNAs. The degree of phosphorylation mediated WT or mutant proteins was determined by binding of three endogenous lysosomal enzymes to CI-MPR-affinity beads. Bound material was assayed for activity and values obtained with cells transfected with WT α/β are set to 100%.

(FIG. 12A) Schematic of WT GlcNAc-1-phosphotransferase α/β subunit modular arrangement and that of the minimal enzyme, S1-S3. The minimal enzyme was generated by replacement of the human spacer-1 sequence with *D. discoideum* spacer-1 and removal of amino acids 438-928. (FIG. 12B) Expi293F cells or mouse D9 cells were co-transfected with expression plasmids for the indicated lysosomal enzymes along with empty vector, WT α/β precursor or the S1-S3 mutant cDNA. The degree of phosphorylation mediated by either the WT α/β precursor or the S1-53 mutant was determined for each enzyme by binding to CI-MPR-affinity beads and assaying the activity of the bound material as described under Methods. Values obtained with empty vector are indicative of activity mediated by the endogenous GlcNAc-1-phosphotransferase. (FIG. 12C) GNPTAB$^{-/-}$ HeLa cells were co-transfected with either WT α/β precursor or the S1-S3 deletion mutant cDNA, along with expression plasmids for 4 lysosomal enzymes, while parental HeLa cells were transfected with only cDNAs for the latter and utilized the endogenous GlcNAc phosphotransferase activity. 48 h post-transfection, cells were labeled for 2 h with [2-$^3$H]-mannose, followed by immunoprecipitation of the proteins secreted into the media and determination of the percent N-glycans containing Man-6-P. The absolute values of the % phosphorylation are shown.

DETAILED DESCRIPTION OF THE INVENTION

Figure 1A:
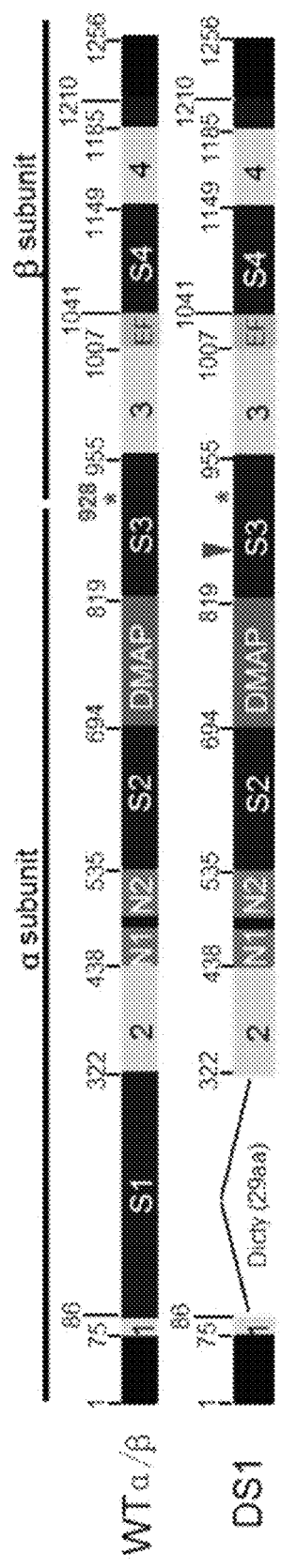

The inventors show that a truncated α/β precursor that lacks a number of the a subunit elements while retaining the catalytic "Stealth" domains is expressed at very high levels resulting in a 20-fold greater catalytic activity than occurs with the WT enzyme. The truncated α/β precursor stimulated mannose phosphorylation over endogenous levels of various lysosomal and non-lysosomal proteins. Further, the truncated enzyme increased the formation of glycans with two Man-6-P residues which results in much higher affinity for the Manose-6-P receptors. Lysosomal enzyme phosphorylation can be substantially increased by co-transfection with either WT or truncated α/β precursor of GlcNAc-1-phosphotransferase. The enhanced phosphorylation increases binding and uptake by cells. This effect even occurs with lysosomal enzymes such as GalA that are well phosphorylated by the endogenous GlcNAc-1-phosphotransferase. Furthermore, this method enhances the phosphorylation and uptake of LAMAN and GAA, two lysosomal enzymes that are poorly phosphorylated by endogenous GlcNAc-1-phosphotransferase. Various aspects of the disclosure are described in more detail below.

I. Compositions

In an aspect, the disclosure provides an isolated polypeptide, the polypeptide comprising GlcNAc-1-phosphotransferase (GlcNAc-1-PT) α/β subunit. In another aspect, the disclosure provides an isolated polynucleotide, the polynucleotide encoding at least one polypeptide, the polypeptide comprising GlcNAc phosphotransferase (GlcNAc-1-PT) α/β subunit. In still another aspect, the disclosure provides a vector comprising a polynucleotide, the polynucleotide encoding at least one polypeptide, the polypeptide comprising GlcNAc-1-phosphotransferase (GlcNAc-1-PT) α/β subunit. In still yet another aspect, the disclosure provides a host cell comprising a vector comprising a polynucleotide, the polynucleotide encoding at least one polypeptide, the polypeptide comprising GlcNAc-1-phosphotransferase (GlcNAc-1-PT) α/β subunit.

In an aspect, a full length GlcNAc-1-PT protein may include 3 subunits, α, β, and γ subunits. The α and β (GlcNAc-1-PT α/β) subunits may be able to phosphorylate most lysosomal enzymes in the absence of the γ subunit. GlcNAc-1-PT α/β subunits may include various conserved domains. The conserved domains of the GlcNAc-1-PT α/β subunits may include, arranged from the N- to C-terminus of the polypeptide, a spacer-1 domain (spacer-1), a Notch 1 domain (Notch 1), a Notch 2 domain (Notch 2), a spacer-2 domain (spacer-2), a DNA methyltransferase-associated protein interaction domain (DMAP), a spacer-3 domain (spacer-3), and a spacer-4 domain (spacer-4). The α subunit may include arranged from the N- to C-terminus of the polypeptide a spacer-1, a Notch 1, a Notch 2, a spacer-2, and a DMAP. Spacer-3 may span the α and β subunit, and may include the site at which the α and β subunit may be cleaved, the α/β subunit cleavage site. The spacer-4 may be in the β subunit.

In an aspect, a GlcNAc-1-PT α/β subunit may be modified by deletion of one or more conserved domains. By way of non-limiting example, a modified GlcNAc-1-PT α/β subunit may include a deletion of one or more of spacer-1, Notch 1, Notch 2, spacer-2, DMAP, and a part of spacer-3. In an aspect, a modified GlcNAc-1-PT α/β subunit may include a spacer-1 deletion. In an aspect, a modified GlcNAc-1-PT α/β subunit may include a spacer-1 and Notch 1 deletion. In an aspect, a modified GlcNAc-1-PT α/β subunit may include a spacer-1, and Notch 2 deletion. In an aspect, a modified GlcNAc-1-PT α/β subunit may include a spacer-1, Notch 1, and Notch 2 deletion. In an aspect, a modified GlcNAc-1-PT α/β subunit may include a spacer-1, Notch 1, Notch 2, and spacer-2 deletion. In an aspect, a modified GlcNAc-1-PT α/β subunit may include a spacer-1, Notch 1, Notch 2, spacer-2, and DMAP deletion. In an aspect, a modified GlcNAc-1-PT α/β subunit may include a spacer-1, Notch 1, Notch 2, spacer-2, and DMAP deletion, and a deletion of a part of spacer-3 at the α/β subunit cleavage site of spacer-3.

In an aspect, the disclosure provides an isolated polypeptide, the polypeptide comprising GlcNAc-1-phosphotransferase (GlcNAc-1-PT) α/β subunit, wherein spacer-1 is deleted and the region between Notch 1 and the α/β cleavage site is deleted. In another aspect, the disclosure provides an isolated polynucleotide, the polynucleotide encoding at least one polypeptide, the polypeptide comprising GlcNAc-1-phosphotransferase (GlcNAc-1-PT) α/β subunit, wherein spacer-1 is deleted and the region between Notch 1 and the α/β cleavage site is deleted. In still another aspect, the disclosure provides a vector comprising a polynucleotide, the polynucleotide encoding at least one polypeptide, the polypeptide comprising GlcNAc-1-phosphotransferase (GlcNAc-1-PT) α/β subunit, wherein spacer-1 is deleted and the region between Notch 1 and the α/β cleavage site is deleted. In still yet another aspect, the disclosure provides a host cell comprising a vector comprising a polynucleotide, the polynucleotide encoding at least one polypeptide, the polypeptide comprising GlcNAc-1-phosphotransferase (GlcNAc-1-PT) α/β subunit, wherein spacer-1 is deleted and the region between Notch 1 and the α/β cleavage site is deleted.

(a) GlcNAc-1-Phosphotransferase

In an aspect, the disclosure provides a GlcNAc-1-phosphotransferase (GlcNAc-1-PT). As used herein, the term "GlcNAc-1-phosphotransferase" includes wild-type GlcNAc-1-phosphotransferase, mutant GlcNAc-1-phosphotransferase, functional homologs of GlcNAc-1-phosphotransferase and fragments thereof. GlcNAc-1-PT is an α2β2γ2 hexameric protein encoded by two genes. The smaller γ subunit is encoded by the GNPTG gene, whereas the a and β subunits are encoded as a single α/β precursor by the GNPTAB gene. Proteolytic cleavage of the human α/β precursor at K928 is mediated by the Site-1 protease (S1P) in the Golgi and this cleavage is essential for catalytic competency of the protein. GlcNAc-1-PT performs the initial and most crucial step in the generation of the Man-6-P tag by selectively binding to conformation-dependent protein determinants on lysosomal acid hydrolases and catalyzing the transfer of GlcNAc-1-P from UDP-GlcNAc to mannose residues on high mannose-type N-linked glycans of the hydrolases. Accordingly, a GlcNAc-1-PT of the disclosure, including a functional homolog or fragment, generates a Man-6-P tag. In certain embodiments, a GlcNAc-1-P of the disclosure comprises the α/β subunit. The sequence information for the full length human α/β GlcNAc-1-phosphotransferase amino acid sequence can be found using, for example, the GenBank accession number CAJ30014.1. The sequence information for the full length human α/β GlcNAc-1-phosphotransferase mRNA sequence can be found using, for example, the GenBank accession number AM085438.1. In certain embodiments, an α/β GlcNAc-1-phosphotransferase of the disclosure comprises the sequence set forth in SEQ ID NO:1 (MLFKLLQRQT YTCLSHRYGL YVCFLGVVVT IVSAFQFGEV VLEWSRDQYH VLFDSYRDNI AGKSFQNRLC LPMPIDWYT WVNGTDLELL KELQQVREQM EEEQKAMREI LGKNTTEPTK KSEKQLECLL THCIKVPMLV LDPALPANIT LKDLPSLYPS FHSASDIFNV AKPKNPSTNV SVWFDSTKD VEDAHSGLLK GNSRQTVWRG YLTTD- KEVPG LVLMQDLAFL SGFPPTFKET NQLKTKLPEN LSSKVKLLQL YSEASVALLK LNNPKDFQEL NKQTK- KNMTI DGKELTISPA YLLWDLSAIS QSKQDEDISA SRFEDNEELR YSLRSIERHA PWVRNIFIVT NGQIPSWLNL DNPRVTIVTH QDVFRNLSHL PTFS- SPAIES HIHRIEGLSQ KFIYLNDDVM FGKDVWPDDF YSHSKGQKVY LTWPVPNCAE GCPGSWIKDG YCDKACNNSA CDWDGGDCSG NSGGSRYIAG GGGTGSIGVG QPWQFGGGIN SVSYCNQGCA NSWLADKFCD QACNVLSCGF DAGDCGQDHF HELYKVILLP NQTHYIIPKG ECLPYFSFAE VAKRGVEGAY SDNPIIRHAS IANKWKTIHL IMHSGMNATT IHFNLTFQNT NDEEFKMQIT VEVDTREGPK LNSTAQKGYE NLVSPITLLP EAEIL- FEDIP KEKRFPKFKR HDVNSTRRAQ EEVKIPLVNI SLLPKDAQLS LNTLDLQLEH GDITLKGYNL SKSALLRSFL MNSQHAKIKN QAIITDETND SLVAPQEKQV HKSILPNSLG VSERLQRLTF PAVSVKVNGH DQGQNPPLDL ETTARFRVET HTQKTIGGNV TKEKPPSLIV PLESQMTKEK KITGKEKENS RMEENAENHI GVTEVLLGRK LQHYTDSYLG FLPWEKKKYF QDLLDEEESL KTQLAYFTDS KNTGRQLKDT FADSLRYVNK ILNSKFGFTS RKVPAHMPHM IDRIVMQELQ DMFPEEFDKT SFHKVRHSED MQFAFSYFYY LMSAVQPLNI SQVFDEVDTD QSGVLSDREI RTLA- TRIHEL PLSLQDLTGL EHMLINCSKM LPADITQLNN IPPTQESYYD PNLPPVTKSL VTNCKPVTDK IHKAYKDKNK YRFEIMGEEE IAFKMIRTNV SHVVGQLDDI RKNPRKFVCL NDNIDHNHKD AQTVKAVLRD FYESMFPIPS QFELPREYRN RFLHMHELQE WRAYRDKLKF WTHCVLATLI MFTIFSFFAE QLIALKRKIF PRRRIHKEAS PNRIRV). In other embodiments, a GlcNAc-1-phosphotransferase of the disclosure may have about 80% identity to SEQ ID NO:1, provided it has the same functional activity as GlcNAc-1-PT. For example, a GlcNAc-1-phosphotransferase of the disclosure may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:1, provided it has the same functional activity as GlcNAc-1-PT.

In an aspect, in reference to the full length GlcNAc-1-PT (SEQ ID No:1) the spacer-1 is approximately between amino acid 86 and amino acid 322, the Notch 1 and Notch 2 are approximately between amino acid 438 and amino acid 435, the spacer-2 is approximately between amino acid 535 and amino acid 694, DMAP is approximately between amino acid 694 and amino acid 819, the spacer-3 is approximately between amino acid 819 and amino acid 955, the α/β subunit cleavage site is approximately at amino acid 928, and a spacer-4 is approximately between amino acid 1041 and amino acid 1149.

It is appreciated that the present directed is directed to homologs of GlcNAc-1-PT in other organisms and is not limited to the human GlcNAc-1-PT. Homologs can be found in other species by methods known in the art. In determining whether a protein has significant homology or shares a certain percentage of sequence identity with a sequence of the invention, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See ncbi.nlm.nih.gov for more details.

A GlcNAc-1-PT homolog may be at least 65, 70, 75, 80, 85, 90, or 95% homologous to human GlcNAc-1-PT provided it has the same functional activity as GlcNAc-1-PT. In certain embodiments, a GlcNAc-1-PT homolog may be at least 65, 66, 67, 68, 69, or 70% homologous to human GlcNAc-1-PT provided it has the same functional activity as GlcNAc-1-PT. In different embodiments, a GlcNAc-1-PT homolog may be at least 71, 72, 73, 74, 75, 76, 77, 78 or 79% homologous to human GlcNAc-1-PT provided it has the same functional activity as GlcNAc-1-PT. In one embodiment, a GlcNAc-1-PT homolog may be at least 80, 81, 82, 83, 84, 85, 86, 87, 88, or 89% homologous to human GlcNAc-1-PT. In another embodiment, a GlcNAc-1-PT homolog may be at least 90, 91, 92, 93, 94, 95, 96, 97, 98, 99, or 100% homologous to GlcNAc-1-PT. In yet another embodiment, a GlcNAc-1-PT homolog may be a truncation or variant that has the same functional activity as the full length GlcNAc-1-PT.

Figure 3A:
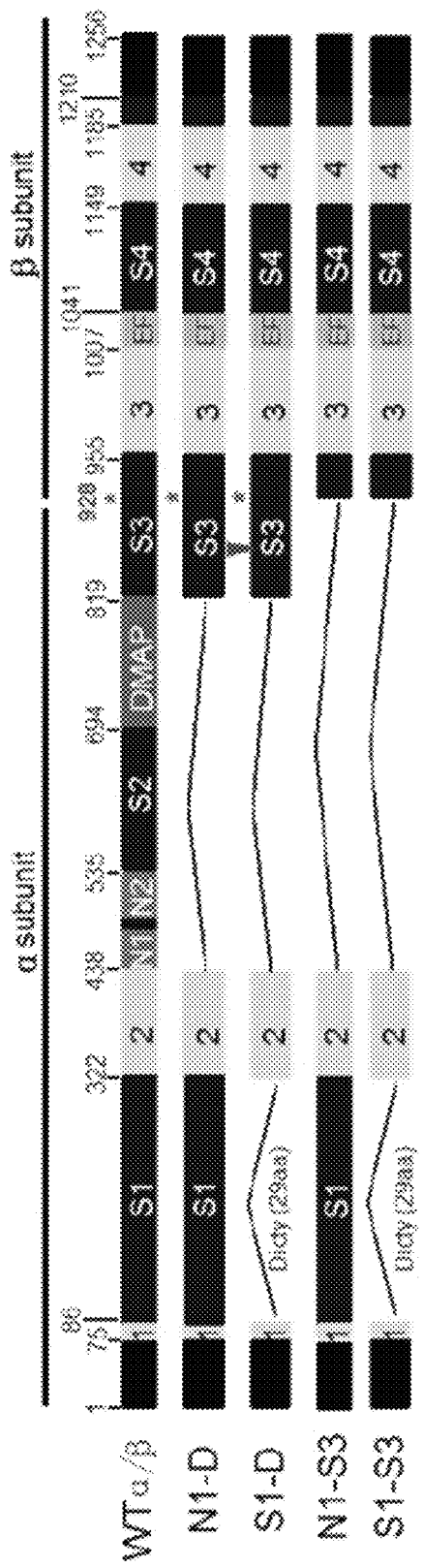
FIG. 3A, FIG. 3B, FIG. 3C, FIG. 3D, FIG. 3E, FIG. 3F and FIG. 3G depict a schematic, graphs and immunoblots showing the generation of a minimal enzyme capable of phosphorylating many glycoproteins non-specifically.

In other embodiments, a GlcNAc-1-P of the disclosure comprises the α/β subunit, wherein spacer-1 is deleted. More specifically, a GlcNAc-1-P of the disclosure comprises the α/β subunit, wherein the amino acids between about amino acid 86 to about amino acid 322 are deleted in reference to SEQ ID NO:1. Deletion of spacer-1 gives rise to a GlcNAc-1-P with enhanced ability to phosphorylate a number of non-lysosomal glycoproteins that are poorly phosphorylated by the wild-type a GlcNAc-1-P. In still other embodiments, a GlcNAc-1-P of the disclosure comprises the α/β subunit, wherein the region between Notch 1 and the α/β cleavage site is deleted. More specifically, a GlcNAc-1-P of the disclosure comprises the α/β subunit, wherein the amino acids between about amino acid 928 are deleted in reference to SEQ ID NO:1. In specific embodiments, a GlcNAc-1-P of the disclosure comprises the α/β subunit, wherein spacer-1 is deleted and the region between Notch 1 and the α/β cleavage site is deleted. More specifically, a GlcNAc-1-P of the disclosure comprises the α/β subunit, wherein the amino acids between about amino acid 86 to about amino acid 322 are deleted and the amino acids between about amino acid 438 and about amino acid 928 are deleted in reference to SEQ ID NO:1. Importantly, the deletion cannot extend beyond amino acid 928. Removal of spacer-1, together with the region between Notch1 and the α/β cleavage site, results in a GlcNAc-1-P that is reminiscent of the bacterial proteins and cells expressing this minimal GlcNAc-1-PT display dramatically increased activity toward the simple sugar α-methyl D-mannoside (αMM) and non-lysosomal glycoproteins as a consequence of its high expression level. A GlcNAc-1-PT α/β subunit wherein spacer-1 is deleted and the region between Notch 1 and the α/β cleavage site is deleted has about 5-fold greater catalytic activity than wild-type GlcNAc-1-PT α/β subunit. For example, a GlcNAc-1-PT α/β subunit wherein spacer-1 is deleted and the region between Notch 1 and the α/β cleavage site is deleted has about 10-fold, about 15-fold, about 20-fold, about 25-fold, or about 30 fold greater catalytic activity than wild-type GlcNAc-1-PT α/β subunit. A GlcNAc-1-PT α/β subunit wherein spacer-1 is deleted and the region between Notch 1 and the α/β cleavage site is deleted increases the content of glycans with 2 Man-6-P residues relative to wild-type GlcNAc-1-PT α/β subunit. For example, a GlcNAc-1-PT α/β subunit wherein spacer-1 is deleted and the region between Notch 1 and the α/β cleavage site is deleted increases the content of glycans with 2 Man-6-P residues by about 1%, about 2%, about 3%, about 4%, about 5%, about 10%, about 15%, about 20% or about 25% relative to wild-type GlcNAc-1-PT α/β subunit. Other modified GlcNAc-1-Ps of the disclosure are depicted in FIG. 3A.

(b) Enzyme Construct

In an aspect, the present disclosure provides an enzyme construct. An enzyme construct of the disclosure is a polynucleotide sequence encoding at least one polypeptide, the polypeptide comprising a GlcNAc-1-phosphotransferase or a fragment thereof. As used herein, the terms "polynucleotide sequence of the disclosure" and "enzyme construct" are interchangeable. The present disclosure also provides isolated polypeptides encoded by enzyme constructs, vectors comprising enzyme constructs, and isolated cells comprising said vectors.

i. Polynucleotide Sequence

An enzyme construct of the disclosure is a polynucleotide sequence encoding at least one polypeptide, the polypeptide comprising a GlcNAc-1-phosphotransferase or a fragment thereof. In certain embodiments, the enzyme construct is a polynucleotide sequence encoding at least one polypeptide, the polypeptide comprising GlcNAc-1-phosphotransferase α/β subunit. In another embodiment, the enzyme construct is a polynucleotide sequence encoding at least one polypeptide, the polypeptide comprising GlcNAc-1-phosphotransferase α/β subunit, wherein spacer-1 is deleted. In still another embodiment, the enzyme construct is a polynucleotide sequence encoding at least one polypeptide, the polypeptide comprising GlcNAc-1-phosphotransferase α/β subunit, wherein the region between Notch 1 and the α/β cleavage site is deleted. In still yet another embodiment, the enzyme construct is a polynucleotide sequence encoding at least one polypeptide, the polypeptide comprising GlcNAc-1-phosphotransferase α/β subunit, wherein spacer-1 is deleted and the region between Notch 1 and the α/β cleavage site is deleted. In a different embodiment, the enzyme construct is a polynucleotide sequence encoding at least two polypeptides, the polypeptides comprising GlcNAc-1-phosphotransferases or fragments thereof.

When more than one polypeptide is encoded by a polynucleotide of the disclosure, the polynucleotide may comprise more than one promoters operably linked to each polynucleotide encoding a polypeptide. By way of non-limiting example, a polynucleotide encoding a polypeptide comprising a first GlcNAc-1-phosphotransferase or a fragment thereof may be operably linked to a first promoter and a polynucleotide encoding a polypeptide comprising a second GlcNAc-1-phosphotransferase or a fragment thereof may be operably linked to a second promoter. The first and second GlcNAc-1-phosphotransferase or a fragment thereof may be the same or different. The first and second promoter may be the same or different. Promoters are described in more detail below.

Alternatively, when more than one polypeptide is encoded by a polynucleotide of the disclosure, the polynucleotide may be operably linked to a single promoter. In such an embodiment, several strategies common in the art may be used to generate more than one expression product. By way of non-limiting example, a splicing signal, internal ribosomal entry site (IRES) or proteolytic cleavage site may be inserted between the polynucleotides encoding the polypeptides. By way of non-limiting example, a polynucleotide encoding a polypeptide comprising a first GlcNAc-1-phosphotransferase or a fragment thereof and a second GlcNAc-1-phosphotransferase or a fragment thereof operably linked to a single promoter may further comprise a splicing signal, IRES or proteolytic cleavage site between the coding regions of the first and second GlcNAc-1-phosphotransferase or a fragment thereof.

In each of the above embodiments, "GlcNAc-1-phosphotransferase," "a fragment thereof," "GlcNAc-1-phosphotransferase α/β subunit," and "GlcNAc-1-phosphotransferase S1-S3" may be as described in detail above in Section I(a), which is hereby incorporated by reference into this section.

Polynucleotide sequences of the disclosure may be produced from nucleic acids molecules using molecular biological methods known to in the art. Any of the methods known to one skilled in the art for the amplification of polynucleotide fragments and insertion of polynucleotide fragments into a vector may be used to construct the polynucleotide sequences of the disclosure. These methods may include in vitro recombinant DNA and synthetic techniques and in vivo recombinations (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

ii. Vector

In another aspect, the present disclosure provides a vector comprising an enzyme construct of the disclosure. As used herein, a vector is defined as a nucleic acid molecule used as a vehicle to transfer genetic material. Vectors include but are not limited to, plasmids, phasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

The vector may have a high copy number, an intermediate copy number, or a low copy number. The copy number may be utilized to control the expression level for the enzyme construct, and as a means to control the expression vector's stability. In one embodiment, a high copy number vector may be utilized. A high copy number vector may have at least 31, 35, 40, 45, 50, 55, 60, 65, 70, 75, 80, 85, 90, 95, or 100 copies per bacterial cell. In other embodiments, the high copy number vector may have at least 100, 125, 150, 175, 200, 225, 250, 275, 300, 325, 350, 375, or 400 copies per host cell. In an alternative embodiment, a low copy number vector may be utilized. For example, a low copy number vector may have one or at least two, three, four, five, six, seven, eight, nine, or ten copies per host cell. In another embodiment, an intermediate copy number vector may be used. For instance, an intermediate copy number vector may have at least 10, 11, 12, 13, 14, 15, 16, 17, 18, 19, 20, 21, 22, 23, 24, 25, 26, 27, 28, 29, or 30 copies per host cell.

Vectors of the present disclosure are typically used for protein expression. As is well known in the art, such vectors may possess a wide array of replication origins, multiple cloning sequences, promoters, ribosomal binding sites/ribosome entry sites, translation initiation sites, transcription terminators, etc. Vectors may also contain one or more polynucleotides sequences encoding for selectable markers, reporters, and peptide tags.

A nucleic acid encoding an enzyme construct may also be operably linked to a nucleotide sequence encoding a selectable marker. A selectable marker may be used to efficiently select and identify cells that have integrated the exogenous nucleic acids. Selectable markers give the cell receiving the exogenous nucleic acid a selection advantage, such as resistance towards a certain toxin or antibiotic. Suitable examples of antibiotic resistance markers include, but are not limited to, those coding for proteins that impart resistance to kanamycin, spectomycin, neomycin, gentamycin (G418), ampicillin, tetracycline, chloramphenicol, puromycin, hygromycin, zeocin, and blasticidin.

In some embodiments, the vector may also comprise a transcription cassette for expressing reporter proteins. By way of example, reporter proteins may include a fluorescent protein, luciferase, alkaline phosphatase, beta-galactosidase, beta-lactamase, horseradish peroxidase, and variants thereof.

An expression vector encoding an enzyme construct may be delivered to the cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. An expression construct encoding an enzyme construct that is introduced to the cell may be linear or circular, may be single-stranded or double-stranded, and may be DNA, RNA, or any modification or combination thereof.

An expression construct encoding an enzyme construct may be introduced into the cell by transfection. Methods for transfecting nucleic acids are well known to persons skilled in the art. Transfection methods include, but are not limited to, viral transduction, cationic transfection, liposome transfection, dendrimer transfection, electroporation, heat shock, nucleofection transfection, magnetofection, nanoparticles, biolistic particle delivery (gene gun), and proprietary transfection reagents such as Lipofectamine, Dojindo Hilymax, Fugene, jetPEI, Effectene, or DreamFect.

Upon introduction into the cell, an expression construct encoding an enzyme construct may be integrated into a chromosome. In some embodiments, integration of the expression construct encoding an enzyme construct into a cellular chromosome may be achieved with a mobile element. The mobile element may be a transposon or a retroelement. A variety of transposons are suitable for use in the invention. Examples of DNA transposons that may be used include the Mu transposon, the P element transposons from *Drosophila*, and members of the Tc1/Mariner superfamily of transposons such as the sleeping beauty transposon from fish. A variety of retroelements are suitable for use in the invention and include LTR-containing retrotransposons and non-LTR retrotransposons. Non-limiting examples of retrotransposons include Copia and gypsy from *Drosophila melanogaster*, the Ty elements from *Saccharomyces cerevisiae*, the long interspersed elements (LINEs), and the short interspersed elements (SINEs) from eukaryotes. Suitable examples of LINEs include L1 from mammals and R2Bm from silkworm.

Integration of the exogenous nucleic acid into a cellular chromosome may also be mediated by a virus. Viruses that integrate nucleic acids into a chromosome include bacteriophages, adeno-associated viruses and retroviruses. Adeno-associated virus (AAV) vectors may be from human or nonhuman primate AAV serotypes and variants thereof. Suitable adeno-associated viruses include AAV type 1, AAV type 2, AAV type 3, AAV type 4, AAV type 5, AAV type 6, AAV type 7, AAV type 8, AAV type 9, AAV type 10, and AAV type 11. A variety of retroviruses are suitable for use in the invention. Retroviral vectors may either be replication-competent or replication-defective. The retroviral vector may be an alpharetrovirus, a betaretrovirus, a gammaretrovirus, a deltaretrovirus, an epsilonretrovirus, a lentivirus, or a spumaretrovirus. In an embodiment, the retroviral vector may be a lentiviral vector. The lentiviral vector may be derived from human, simian, feline, equine, bovine, or lentiviruses that infect other mammalian species. Non-limiting examples of suitable lentiviruses includes human immunodeficiency virus (HIV), simian immunodeficiency virus (SIV), feline immunodeficiency virus (FIV), bovine immunodeficiency virus (BIV), and equine infectious anemia virus (EIAV).

Integration of an expression construct encoding an enzyme construct into a chromosome of the cell may be random. Alternatively, integration of an expression construct encoding an enzyme construct may be targeted to a particular sequence or location of a chromosome. In general, the general environment at the site of integration may affect whether the integrated expression construct encoding an enzyme construct is expressed, as well as its level of expression.

Cells transfected with the expression construct encoding an enzyme construct generally will be grown under selection to isolate and expand cells in which the nucleic acid has integrated into a chromosome. Cells in which the expression construct encoding an enzyme construct has been chromosomally integrated may be maintained by continuous selection with the selectable marker as described above. The presence and maintenance of the integrated exogenous nucleic acid sequence may be verified using standard techniques known to persons skilled in the art such as Southern blots, amplification of specific nucleic acid sequences using the polymerase chain reaction (PCR), and/or nucleotide sequencing.

Nucleic acid molecules are inserted into a vector that is able to express the fusion polypeptides when introduced into an appropriate host cell. Appropriate host cells include, but are not limited to, bacterial, yeast, insect, and mammalian cells.

iii. Regulation

In certain aspects, the expression of a polynucleotide sequence of the disclosure may be regulated. Such regulation may allow control over when and where an enzyme construct functions.

Expression vectors typically contain one or more of the following elements: promoters, terminators, ribosomal binding sites/ribosomal entry sites, and translation initiation sites. Such elements may be used to control the expression of an enzyme construct of the disclosure. Expression of the nucleic acid molecules of the disclosure may be regulated by a second nucleic acid sequence so that the molecule is expressed in a host transformed with the recombinant DNA molecule. For example, expression of the nucleic acid molecules of the disclosure may be controlled by any promoter/enhancer element known in the art. The term "promoter", as used herein, may mean a synthetic or naturally-derived molecule that is capable of conferring, activating or enhancing expression of a nucleic acid. A promoter may be constitutive, inducible/repressible or cell type specific. In certain embodiments, the promoter may be constitutive. Non-limiting examples of constitutive promoters for mammalian cells include CMV, UBC, EF1α, SV40, PGK, CAG, CBA/CAGGS/ACTB, CBh, MeCP2, U6 and H1. In other embodiments, the promoter may be an inducible promoter. The inducible promoter may be selected from the group consisting of: tetracycline, heat shock, steroid hormone, heavy metal, phorbol ester, adenovirus E1A element, interferon, and serum inducible promoters. In different embodiments, the promoter may be cell type specific. For example, cell type specific promoters for neurons (e.g. syapsin), astrocytes (e.g. GFAP), oligodendrocytes (e.g. myelin basic protein), microglia (e.g. CX3CR1), neuroendocrine cells (e.g. chromogranin A), muscle cells (e.g. desmin, Mb), or cardiomyocytes (e.g. alpha myosin heavy-chain promoter) could be used. In an exemplary embodiment, a promoter may be the Nrl (rod photoreceptor-specific) promoter or the HBB (haemoglobin beta) promoter. A promoter may further comprise one or more specific transcriptional regulatory sequences to further enhance expression and/or to alter the spatial expression and/or temporal expression of a nucleic acid. Non-limiting examples of enhancer include the CMV enhancer and the SP1 enhancer.

In an embodiment where more than one polypeptide is encoded by a polynucleotide of the disclosure and the polynucleotide comprises more than one promoters operably linked to each polynucleotide encoding a polypeptide, the promoters may be the same or different. The term "operably linked," as used herein, means that expression of a nucleic acid sequence is under the control of a promoter with which it is spatially connected. A promoter may be positioned 5' (upstream) of the nucleic acid sequence under its control. The distance between the promoter and a nucleic acid sequence to be expressed may be approximately the same as the distance between that promoter and the native nucleic acid sequence it controls. As is known in the art, variation in this distance may be accommodated without loss of promoter function.

iv. Host Cell

In another aspect, the present disclosure provides a host cell comprising a vector of the disclosure. The cell may be a prokaryotic cell or a eukaryotic cell. Appropriate cells include, but are not limited to, bacterial, yeast, fungal, insect, and mammalian cells. Host cells according to the present disclosure are cells are maintained in vitro in substantially pure cultures (i.e. isolated cells). A host cell comprising a vector of the disclosure may be used for protein expression and, optionally, purification. Methods for expressing and, optionally, purifying an expressed protein from a host are standard in the art.

In some embodiments, the host cell comprising a vector of the disclosure may be used to produce a polypeptide encoded by an enzyme construct of the disclosure. Generally, production of a polypeptide of the disclosure involves transfecting host cells with a vector comprising an enzyme construct and then culturing the cells so that they transcribe and translate the desired polypeptide. The isolated host cells may then be lysed to extract the expressed polypeptide for subsequent purification.

In some embodiments, the host cell is a prokaryotic cell. Non-limiting examples of suitable prokaryotic cells include *E. coli* and other Enterobacteriaceae, *Escherichia* sp., *Campylobacter* sp., *Wolinella* sp., *Desulfovibrio* sp. *Vibrio* sp., *Pseudomonas* sp. *Bacillus* sp., *Listeria* sp., *Staphylococcus* sp., *Streptococcus* sp., *Peptostreptococcus* sp., *Megasphaera* sp., *Pectinatus* sp., *Selenomonas* sp., *Zymophilus* sp., *Actinomyces* sp., *Arthrobacter* sp., *Frankia* sp., *Micromonospora* sp., *Nocardia* sp., *Propionibacterium* sp., *Streptomyces* sp., *Lactobacillus* sp., *Lactococcus* sp., *Leuconostoc* sp., *Pediococcus* sp., *Acetobacterium* sp., *Eubacterium* sp., *Heliobacterium* sp., *Heliospirillum* sp., *Sporomusa* sp., *Spiroplasma* sp., *Ureaplasma* sp., *Erysipelothrix* sp., *Corynebacterium* sp. *Enterococcus* sp., *Clostridium* sp., *Mycoplasma* sp., *Mycobacterium* sp., *Actinobacteria* sp., *Salmonella* sp., *Shigella* sp., *Moraxella* sp., *Helicobacter* sp, *Stenotrophomonas* sp., *Micrococcus* sp., *Neisseria* sp., *Bdellovibrio* sp., *Hemophilus* sp., *Klebsiella* sp., *Proteus mirabilis*, *Enterobacter cloacae*, *Serratia* sp., *Citrobacter* sp., *Proteus* sp., *Serratia* sp., *Yersinia* sp., *Acinetobacter* sp., *Actinobacillus* sp. *Bordetella* sp., *Brucella* sp., *Capnocytophaga* sp., *Cardiobacterium* sp., *Eikenella* sp., *Francisella* sp., *Haemophilus* sp., *Kingella* sp., *Pasteurella* sp., *Flavobacterium* sp. *Xanthomonas* sp., *Burkholderia* sp., *Aeromonas* sp., *Plesiomonas* sp., *Legionella* sp. and alpha-proteobaeteria such as *Wolbachia* sp., cyanobacteria, spirochaetes, green sulfur and green non-sulfur bacteria, Gram-negative cocci, Gram negative bacilli which are fastidious, Enterobacteriaceae-glucose-fermenting gram-negative bacilli, Gram negative bacilli-non-glucose fermenters, Gram negative bacilli-glucose fermenting, oxidase positive. Particularly useful bacterial host cells for protein expression include Gram negative bacteria, such as *Escherichia coli*, *Pseudomonas fluorescens*, *Pseudomonas haloplanctis*, *Pseudomonas putida* AC10, *Pseudomonas pseudoflava*, *Bartonella henselae*, *Pseudomonas syringae*, *Caulobacter crescentus*, *Zymomonas mobilis*, *Rhizobium meliloti*, *Myxococcus xanthus* and Gram positive bacteria such as *Bacillus subtilis*, *Corynebacterium*, *Streptococcus cremoris*, *Streptococcus lividans*, and *Streptomyces lividans*. *E. coli* is one of the most widely used expression hosts. Accordingly, the techniques for overexpression in *E. coli* are well developed and readily available to one of skill in the art. Further, *Pseudomonas fluorescens*, is commonly used for high level production of recombinant proteins (i.e. for the development of bio-therapeutics and vaccines).

In some embodiments, a host cell is a yeast or fungal cell. Particularly useful fungal host cells for protein expression include *Aspergillis oryzae*, *Aspergillis niger*, *Trichoderma reesei*, *Aspergillus nidulans*, *Fusarium graminearum*. Particularly useful yeast host cells for protein expression include *Candida albicans*, *Candida maltose*, *Hansenula polymorpha*, *Kluyveromyces fragilis*, *Kluyveromyces lactis*, *Pichia guillerimondii*, *Pichia pastoris*, *Saccharomyces cerevisiae*, *Schizosaccharomyces pombe*, and *Yarrowia lipolytica*.

In some embodiments, a host cell is a mammalian cell. Particularly useful mammalian host cells for protein expression include Chinese hamster ovary (CHO) cells, HeLa cells, baby hamster kidney (BHK) cells, monkey kidney cells (COS), human hepatocellular carcinoma cells (eg. Hep G2), human embryonic kidney cells, *Bos primigenius*, and *Mus musculus*. In a specific embodiment, the host cells are CHO cells. Additionally, the mammalian host cell may be an established, commercially-available cell line (e.g., American Type Culture Collection (ATCC), Manassas, Va.). The host cell may be an immortalized cell. Alternatively, the host cell may be a primary cell. "Primary cells" are cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

In an aspect, the host cell has been engineered to produce high levels of a protein of interest. For example, the host cell has been engineered to produce a protein that would benefit from being tagged with mannose-6-phosphate (Man-6-P). In certain embodiments, the protein of interest is a lysosomal protein. Non-limiting examples of lysosomal proteins include β-glucocebrosidase (GBA), GalA, Cathepsin D (CathD), Niemann-Pick disease type C2 (NPC2), β-hexosaminidase (HEXB), α-Galactosidase (GLA), β-Mannosidase (MANBA), alpha-L-idurnoidase, iduronate sulfatase, arylsulfatase B, acid α-glucosidase (GAA), and lysosomal acid α-mannosidase (LAMAN). Specifically, the lysosomal protein is acid α-glucosidase (GAA) or lysosomal acid α-mannosidase (LAMAN). These proteins are especially useful in combination with the disclosed GlcNAc-1-PT as they may be poorly phosphorylated with endogenous GlcNAc-1-PT. In other embodiments, the protein of interest is a non-lysosomal protein. Non-limiting examples of non-lysosomal proteins include DNase1, Renin, leukemia inhibitory factor (LIF), protein O-fucosyltransferase 2 (PoFUT2), glycopepsinogen (GP), and the von Willebrand factor A1A2A3 domains.

v. Polypeptide Sequence

In another aspect, the present disclosure provides one or more isolated polypeptide(s) encoded by a polynucleotide sequence of the disclosure. Polynucleotide sequences of the disclosure are described in detail in Section I(b)i, and are hereby incorporated by reference into this section. As used herein, the term "isolated polypeptide" refers to a polypeptide that has been partially or completely purified from the cell from which it was produced. Isolated polypeptides of the disclosure may be produced using molecular biological methods known to in the art. Generally speaking, a polynucleotide sequence encoding the polypeptide is inserted into a vector that is able to express the polypeptide when introduced into an appropriate host cell. Appropriate vectors and host cells are described in Section I(b)iii and Section I(b)iv, respectively. Once expressed, polypeptides may be obtained from cells using common purification methods. For example, if the polypeptide has a secretion signal, expressed polypeptides may be isolated from cell culture supernatant. Alternatively, polypeptides lacking a secretion signal may be purified from inclusion bodies and/or cell extract. Polypeptides of the disclosure may be isolated from culture supernatant, inclusion bodies or cell extract using any methods known to one of skill in the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Isolation of polypeptides is greatly aided when the polypeptide comprises affinity tag or purification tag, as described herein.

In an embodiment, an isolated polypeptide of the disclosure comprises GlcNAc-1-phosphotransferase or a fragment thereof. In another embodiment, an isolated polypeptide of the disclosure comprises GlcNAc-1-phosphotransferase α/β subunit. In still another embodiment, an isolated polypeptide of the disclosure comprises GlcNAc-1-phosphotransferase α/β subunit, wherein spacer-1 is deleted. In still yet another embodiment, an isolated polypeptide polypeptide of the disclosure comprises GlcNAc-1-phosphotransferase α/β subunit, wherein the region between Notch 1 and the α/β cleavage site is deleted. In still yet another embodiment, an isolated polypeptide of the disclosure comprises GlcNAc-1-phosphotransferase α/β subunit, wherein spacer-1 is deleted and the region between Notch 1 and the α/β cleavage site is deleted.

II. Methods

In an aspect, the disclosure provides a method to increase oligosaccharide phosphorylation of a protein of interest, the method comprising expressing an exogenous GlcNAc-1-PT in a cell. The exogenous GlcNAc-1-PT may be as described in Section I(a). The cell may be a host cell as described in Section I(b)iv. Specifically, the cell is a CHO cell. The amount of phosphorylation may be increased by greater than 1% relative to phosphorylation in the presence of endogenous GlcNAc PT only. Additionally, the amount of phosphorylation may be increased by greater than 2%, greater than 3%, greater than 4%, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, or greater than 75% relative to phosphorylation in the presence of endogenous GlcNAc-1-PT only. Specifically, when the exogenous GlcNAc-1-PT is GlcNAc-1-phosphotransferase α/β subunit, the amount of phosphorylation may be increased by greater than 2%, greater than 3%, greater than 4%, greater than 5%, greater than 10%, greater than 15%, greater than 20%, or greater than 25% relative to phosphorylation in the presence of endogenous GlcNAc-1-PT only. Further, when the exogenous GlcNAc-1-PT is GlcNAc-1-phosphotransferase α/β subunit, wherein spacer-1 is deleted and the region between Notch 1 and the α/β cleavage site is deleted, the amount of phosphorylation may be increased by greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, or greater than 75% relative to phosphorylation in the presence of endogenous GlcNAc-1-PT only. Further, the method may increase the content of glycans with 2 Man-6-P residues. For example, a GlcNAc-1-PT α/β subunit wherein spacer-1 is deleted and the region between Notch 1 and the α/β cleavage site is deleted increases the content of glycans with 2 Man-6-P residues by about 1%, about 2%, about 3%, about 4%, about 5%, about 10%, about 15%, about 20% or about 25% relative to wild-type GlcNAc-1-PT α/β subunit. The protein of interest is a protein that would benefit from being tagged with mannose-6-phosphate (Man-6-P). In certain embodiments, the protein of interest is a lysosomal protein. Non-limiting examples of lysosomal proteins include β-glucocebrosidase (GBA), GalA, Cathepsin D (CathD), Niemann-Pick disease type C2 (NPC2), β-hexosaminidase (HEXB), α-Galactosidase (GLA), β-Mannosidase (MANBA), alpha-L-idurnoidase, iduronate sulfatase, arylsulfatase B, acid α-glucosidase (GAA), and lysosomal acid α-mannosidase (LAMAN). Specifically, the lysosomal protein is acid α-glucosidase (GAA) or lysosomal acid α-mannosidase (LAMAN). In other embodiments, the protein of interest is a non-lysosomal protein. Non-limiting examples of non-lysosomal proteins include DNase1, Renin, leukemia inhibitory factor (LIF), protein O-fucosyltransferase 2 (PoFUT2), glycopepsinogen (GP), and the von Willebrand factor A1A2A3 domains.

In another aspect, the disclosure provides a method to increase binding of a protein of interest to cell surface (Man-6-P)receptors, the method comprising expressing an exogenous GlcNAc-1-PT in a cell. The exogenous GlcNAc-1-PT may be as described in Section I(a). The cell may be a host cell as described in Section I(b)iv. Specifically, the cell is a CHO cell. An increase in binding of a protein of interest to cell surface (Man-6-P) receptors may result in increased protein of interest uptake. The binding may be increased by greater than 1.5-fold relative to phosphorylation in the presence of endogenous GlcNAc-1-PT only. Additionally, the binding may be increased by greater than 2-fold, greater than 3-fold, greater than 4-fold, greater than 5-fold, greater than 10-fold, greater than 20-fold, greater than 30-fold, greater than 40-fold, greater than 50-fold, greater than 60-fold, greater than 70-fold, greater than 80-fold, greater than 90-fold, greater than 100-fold, greater than 110-fold, greater than 120-fold, greater than 130-fold, greater than 140-fold, or greater than 150-fold relative to binding in the presence of endogenous GlcNAc-1-PT only. Specifically, when the exogenous GlcNAc-1-PT is GlcNAc-1-phosphotransferase α/β subunit, the binding may be increased by greater than 1.5-fold, greater than 2-fold, greater than 3-fold, greater than 4-fold, greater than 5-fold, greater than 10-fold, greater than 20-fold, greater than 30-fold, greater than 40-fold, greater than 50-fold, greater than 60-fold, greater than 70-fold, greater than 80-fold, greater than 90-fold, greater than 100-fold, greater than 110-fold, greater than 120-fold, greater than 130-fold, greater than 140-fold, or greater than 150-fold relative to binding in the presence of endogenous GlcNAc-1-PT only. Further, when the exogenous GlcNAc-1-PT is GlcNAc phosphotransferase α/β subunit, wherein spacer-1 is deleted and the region between Notch 1 and the α/β cleavage site is deleted, the binding may be increased by greater than 2-fold, greater than 3-fold, greater than 4-fold, greater than 5-fold, greater than 10-fold, greater than 20-fold, greater than 30-fold, greater than 40-fold, greater than 50-fold, greater than 60-fold, greater than 70-fold, greater than 80-fold, greater than 90-fold, greater than 100-fold, greater than 110-fold, greater than 120-fold, or greater than 130-fold relative to binding in the presence of endogenous GlcNAc-1-PT only. The protein of interest is a protein that would benefit from being tagged with mannose-6-phosphate (Man-6-P). In certain embodiments, the protein of interest is a lysosomal protein. Non-limiting examples of lysosomal proteins include β-glucocebrosidase (GBA), GalA, Cathepsin D (CathD), Niemann-Pick disease type C2 (NPC2), β-hexosaminidase (HEXB), α-Galactosidase (GLA), β-Mannosidase (MANBA), alpha-L-idurnoidase, iduronate sulfatase, arylsulfatase B, acid α-glucosidase (GAA), and lysosomal acid α-mannosidase (LAMAN). Specifically, the lysosomal protein is acid α-glucosidase (GAA) or lysosomal acid α-mannosidase (LAMAN). In other embodiments, the protein of interest is a non-lysosomal protein. Non-limiting examples of non-lysosomal proteins include DNase1, Renin, leukemia inhibitory factor (LIF), protein O-fucosyltransferase 2 (PoFUT2), glycopepsinogen (GP), and the von Willebrand factor A1A2A3 domains.

In various aspects, the method further comprises isolating or purifying the protein of interest for use in enzyme replacement therapy. Methods of isolating or purifying a protein are known in the art. Enzyme replacement therapy (ERT) may be used to treat lysosomal storage diseases. Non-limiting examples of enzymes (and their corresponding lysosomal storage diseases) for use in ERT include glucocerebrosidase (Gaucher disease), α-galactosidase A (Fabry disease), acid α-glucosidase (Pompe disease), alpha-L-idurnoidase (mucopolysaccharidosis I, Hurler syndrome, Hurler-Scheie syndrome, Scheie syndrome), iduronate sulfatase (mucopolysaccharidosis II, Hunter syndrome), arylsulfatase B (mucopolysaccharidosis VI, Maroteaux-Lamy syndrome). Enzyme replacement therapy is a lifelong therapy. All products are administered intravenously either through a peripheral line or central access device. Infusions typically occur once every 2 weeks, or sometimes weekly. Using a GlcNAc-1-PT of the disclosure, the enzyme prepared may be administered at lowers doses or less frequent intervals. Further, using a GlcNAc-1-PT of the disclosure, lysosomal enzymes generally not available for use due to low phosphorylation maybe used for ERT. Further, the production of GBA containing high levels of Man-6-P offers the opportunity to restore enzyme activity to cell types in patients with Gaucher disease that lack the mannose receptor.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to Examples 1-4

The ability of lysosomes to efficiently degrade intracellular and endocytosed material is dependent upon proper trafficking of the 60 or so soluble acid hydrolases to this organelle. In higher eukaryotes, the sorting process is mediated by the mannose 6-phosphate (Man-6-P) recognition system. Newly synthesized acid hydrolases acquire Man-6-P residues in the cis-Golgi, which serve as high affinity ligands for binding to Man-6-P receptors (MPRs) in the trans-Golgi network and subsequent transport to the endo-lysosomal system (1). The cis-Golgi enzyme UDP-GlcNAc:lysosomal enzyme N-acetylglucosamine-1-phosphotransferase (GlcNAc-1-PT) performs the initial and most crucial step in the generation of the Man-6-P tag by selectively binding to conformation-dependent protein determinants on lysosomal acid hydrolases and catalyzing the transfer of GlcNAc-1-P from UDP-GlcNAc to mannose residues on high mannose-type N-linked glycans of the hydrolases (2). Secretory glycoproteins with identical N-linked glycans do not acquire the Man-6-P tag as they traverse the secretory pathway. Previous studies from our laboratory have demonstrated roles for the two Notch modules and the DNA methyltransferase-associated protein (DMAP) interaction domains of GlcNAc-1-PT in the specific recognition of protein determinants on lysosomal acid hydrolases, resulting in phosphorylation of their high mannose oligosaccharides (3). The likely reason non-lysosomal N-glycosylated proteins are precluded from this process and prevented from being incorrectly targeted to lysosomes is their lack of such determinants.

GlcNAc-1-PT is an $\alpha2\beta2\gamma2$ hexameric protein encoded by two genes. The smaller γ subunit is encoded by the GNPTG gene, whereas the α and β subunits are encoded as a single α/β precursor by the GNPTAB gene (4, 5). Proteolytic cleavage of the human α/β precursor at K928 is mediated by the Site-1 protease (S1P) in the Golgi and this cleavage is essential for catalytic competency of the protein (6). Besides the Notch and DMAP interaction domains, the α and β subunits also harbor four Stealth domains that together form the catalytic core of the protein (FIG. 1A). The Stealth domains of all eukaryotic GlcNAc-1-PTs are highly conserved and resemble sequences within bacterial genes that encode sugar-phosphate transferases involved in cell wall polysaccharide biosynthesis (FIG. 6) (7). Since the bacterial enzymes transfer sugar-phosphates directly to polysaccharide acceptors without the involvement of protein determinants, the currently held view is that mammalian GlcNAc-1-PT, in the course of protein evolution, acquired the Notch and DMAP interaction domains to function in the specific recognition of protein determinants on lysosomal acid hydrolases.

In addition, GlcNAc-1-PT has four so-called "spacer" domains of which only one, spacer-2, has been characterized as the γ-subunit binding site (3, 8). Hitherto, no function has been ascribed to the other spacer regions. In this study, we investigated the role of spacer-1 in the function of GlcNAc-1-PT. Unexpectedly, we found that spacer-1 dictates cleavage of the α/β precursor precisely at K928 by the site-1 protease (S1P) so as to allow for full catalytic activity since removal of spacer-1 results in cleavage at an alternate site (Q882) and a catalytically impaired enzyme. In addition, deletion of spacer-1 gives rise to an enzyme with enhanced ability to phosphorylate a number of non-lysosomal glycoproteins that are poorly phosphorylated by the WT enzyme. Removal of spacer-1, together with the region between Notch1 and the α/β cleavage site, results in a minimal enzyme that is reminiscent of the bacterial proteins. Cells expressing this minimal GlcNAc-1-PT display dramatically increased activity toward the simple sugar α-methyl D-mannoside (αMM) and non-lysosomal glycoproteins as a consequence of its high expression level. Together, these findings reveal a novel and unexpected role for spacer-1 in inhibiting phosphorylation of non-lysosomal proteins and provide new insight into how GlcNAc-1-PT evolved to specifically phosphorylate lysosomal enzymes while at the same time excluding non-lysosomal proteins from becoming phosphorylated and missorted to lysosomes.

Figure 1B:
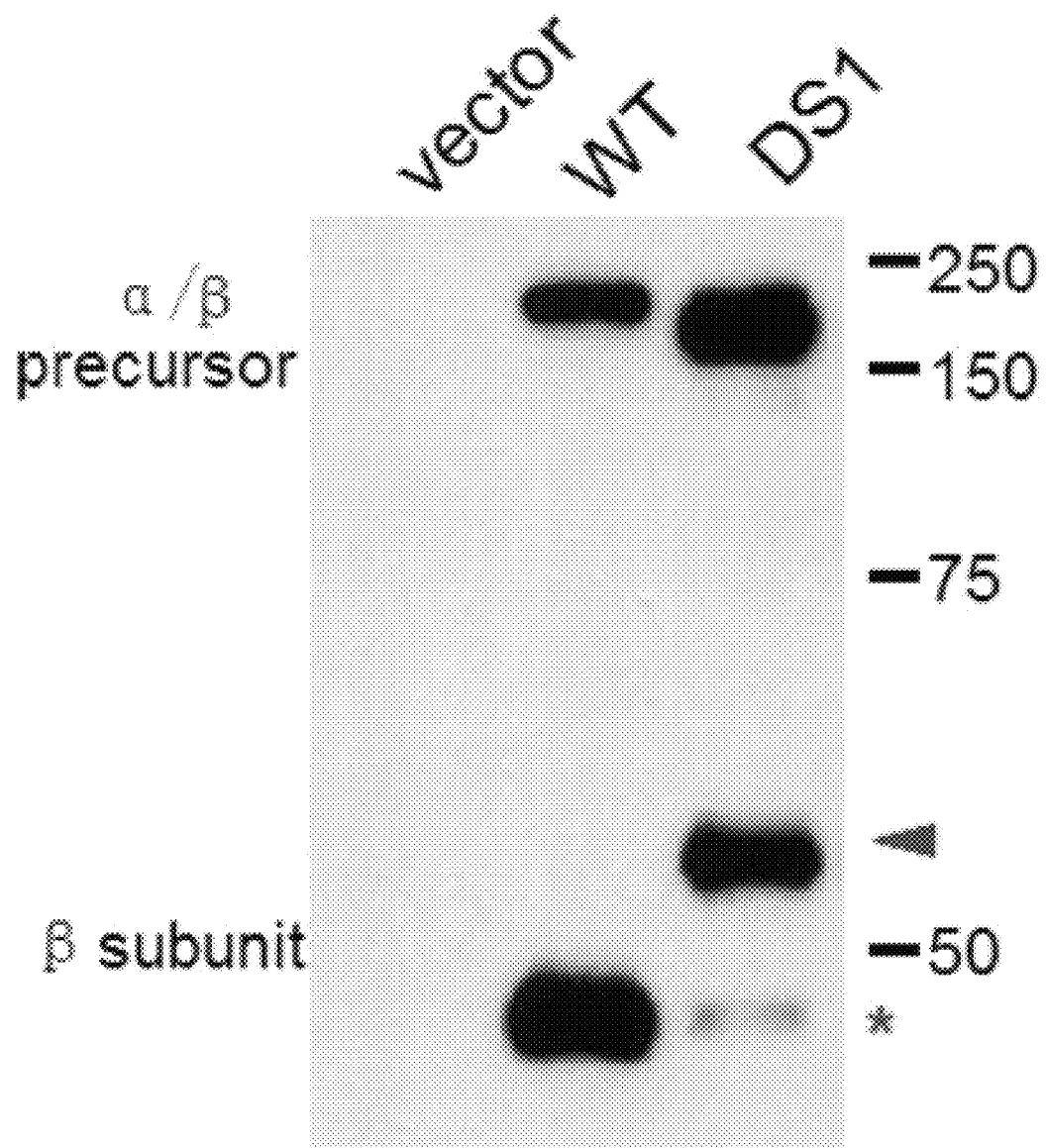
Figure 1C:
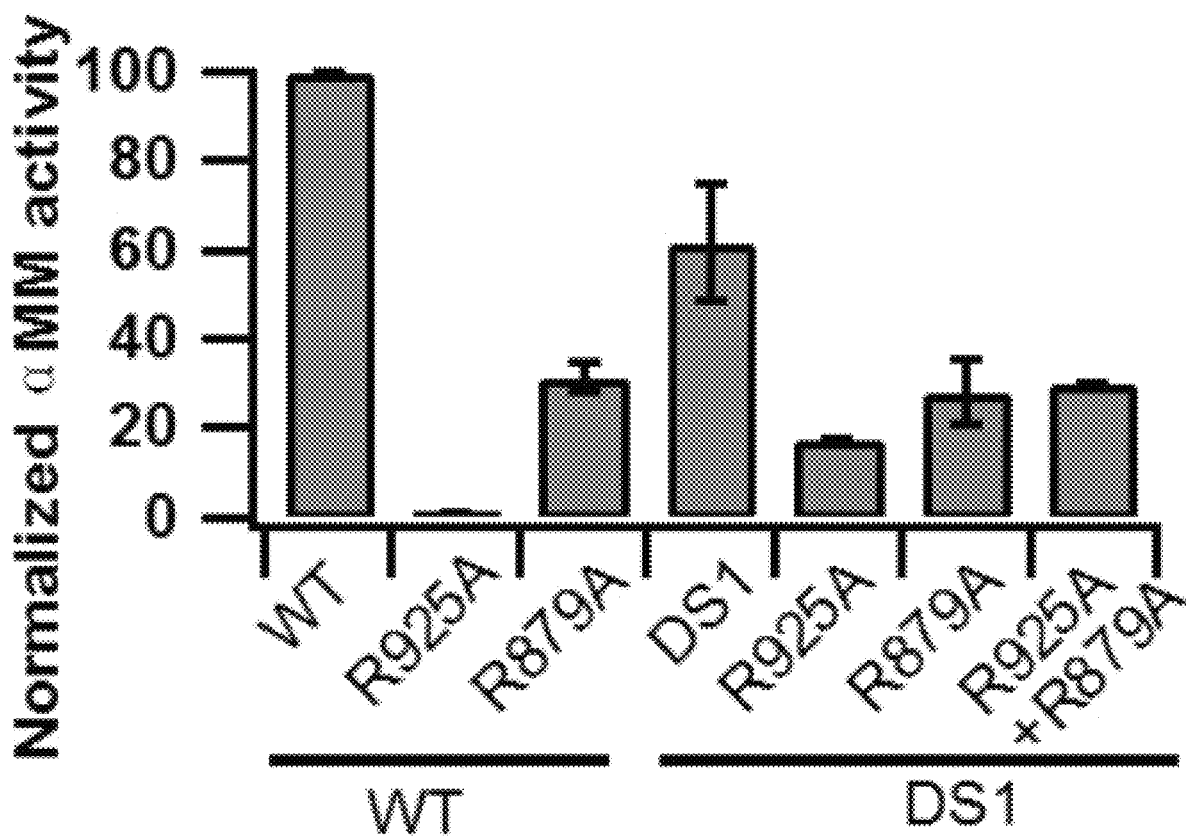
Figure 1D:
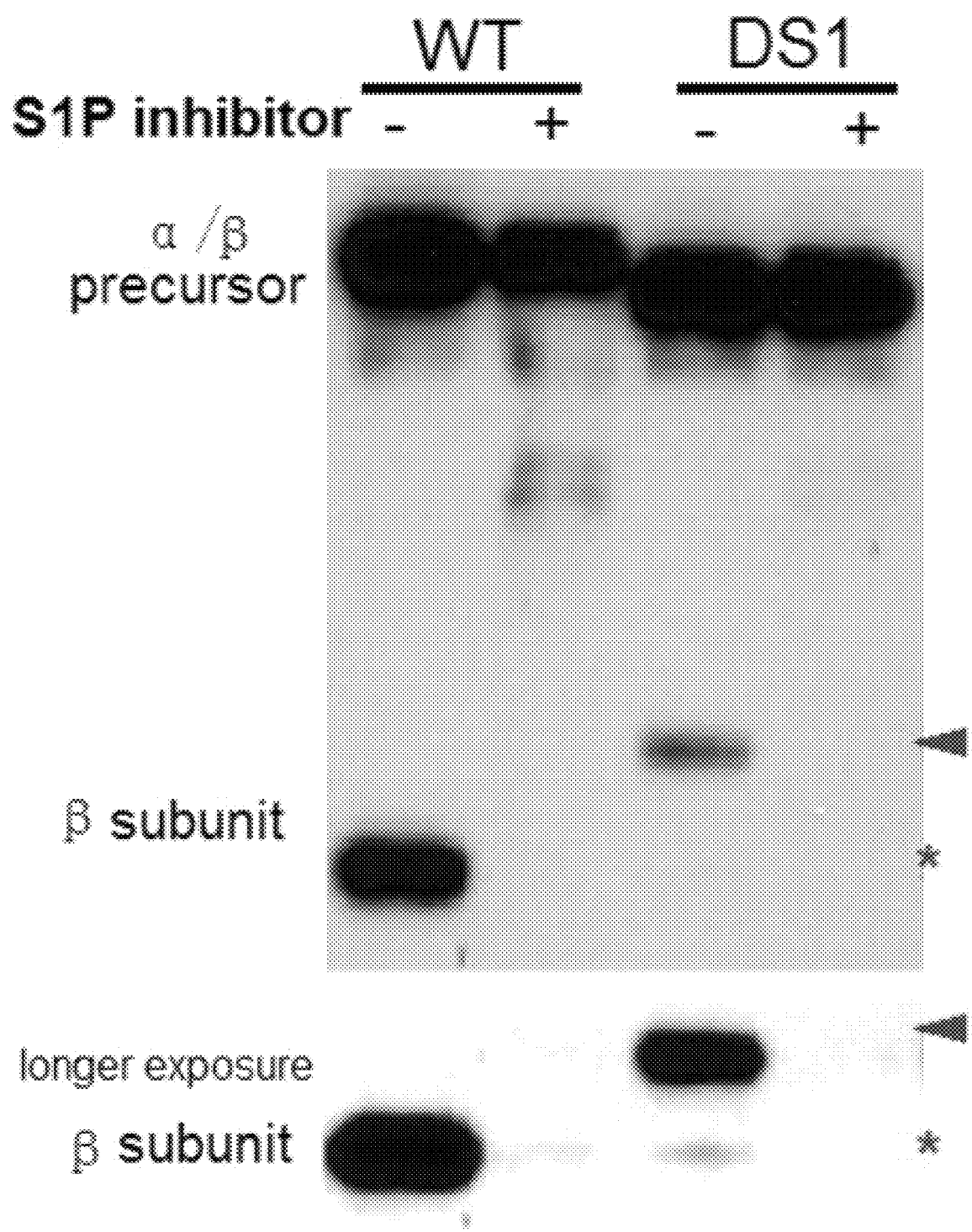
Figure 1F:
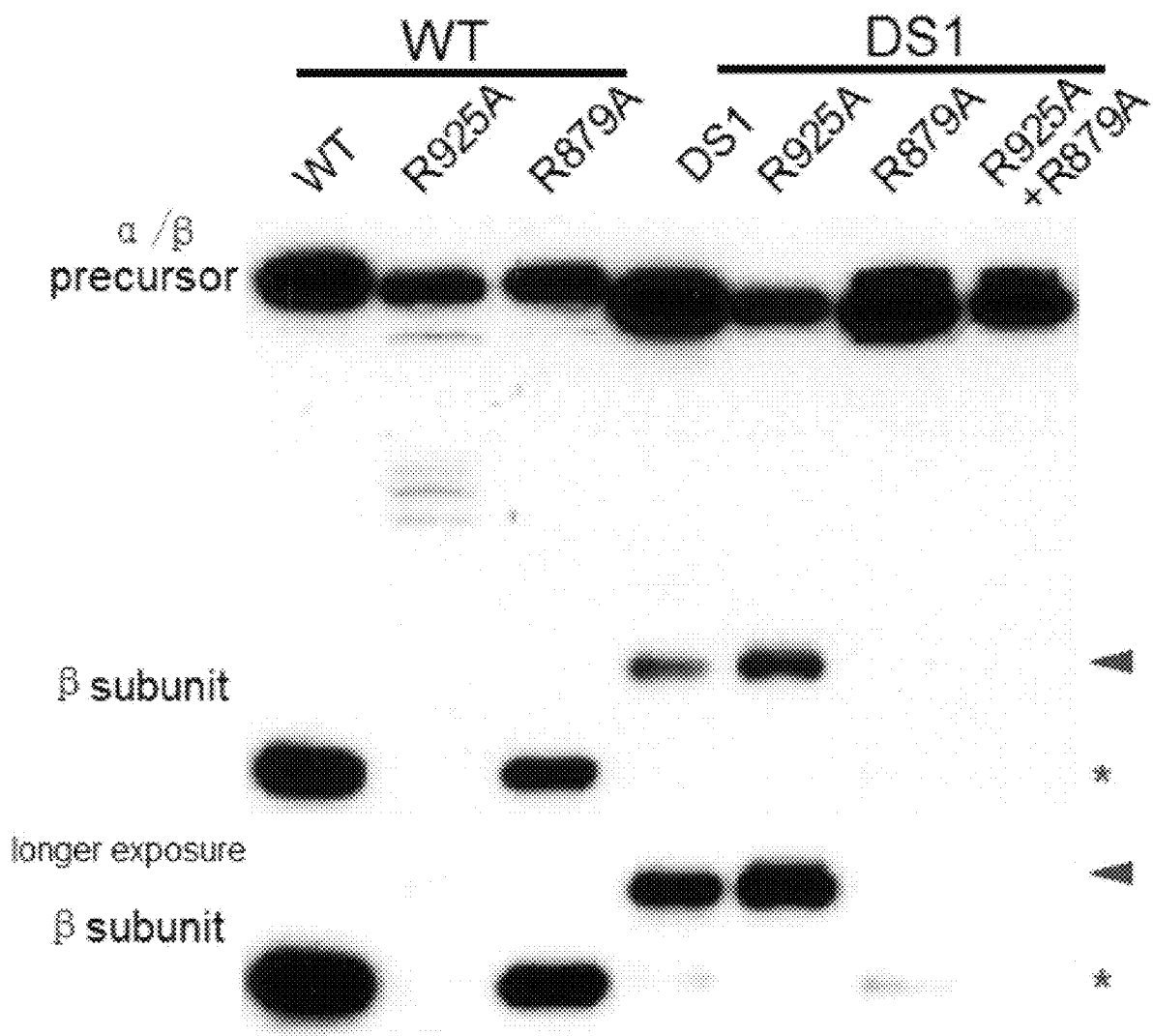
Figure 6:
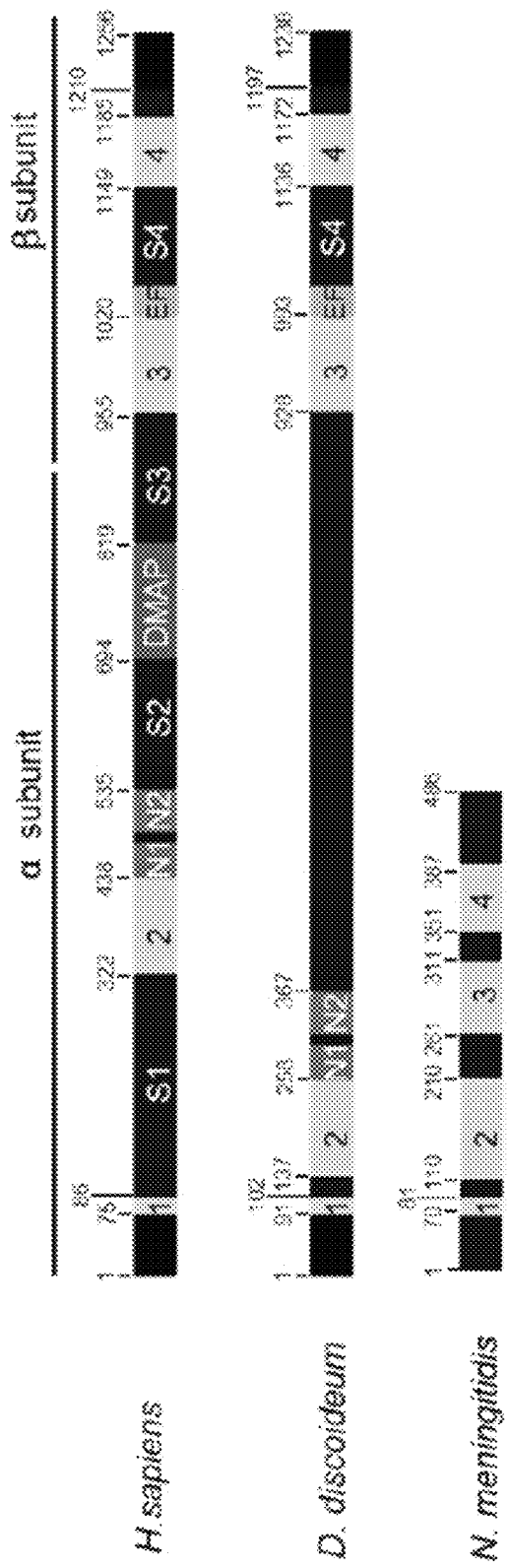
FIG. 6 depicts a schematic showing the modular organization of the different domains of human GlcNAc-1-PT α/13 precursor and alignment with the *D. discoideum* and *N. meningitidis* GlcNAc-1-PT. It is not certain if the *D. discoideum* protein undergoes proteolytic processing like the human protein. The 4 regions shown in green together comprise the Stealth, an evolutionarily conserved domain first identified in bacterial proteins involved in capsular polysaccharide biosynthesis.
Figure 7:
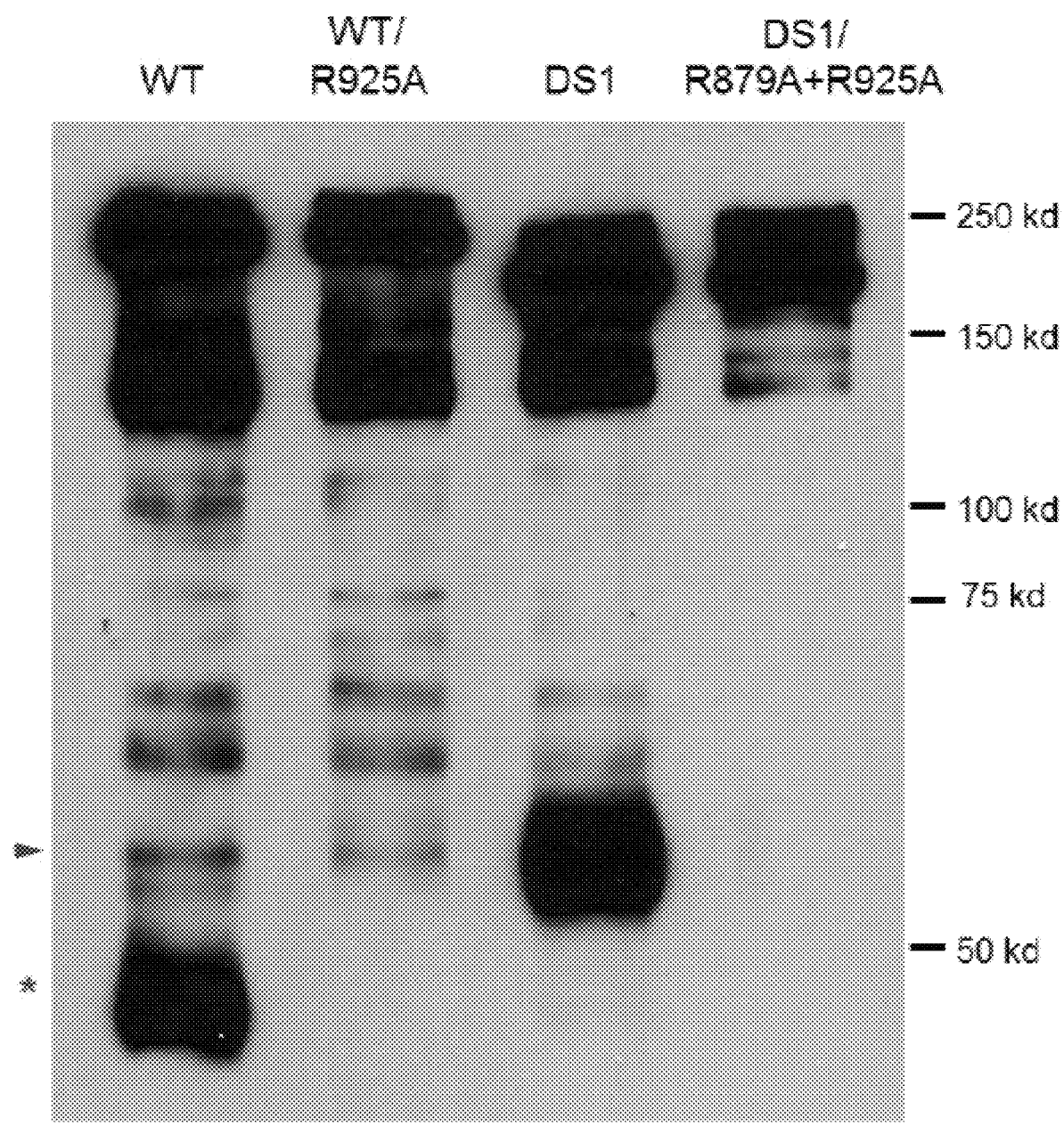
FIG. 7 depicts a Western blot of HEK 293 cells transfected with either WT α/β precursor or the indicated mutant cDNAs. Cell lysates were incubated with Ni-NTA-agarose to affinity purify the α/β precursor as well as the β subunit since the various constructs had in addition to the V-epitope, a 6x-His histidine tag at the C-terminus. The arrowhead indicates the small amount of Q882 cleaved β subunit seen with the WT protein while the * is the normal β due to cleavage at K928. The R925A mutant also showed a small amount of the Q882-cleaved β while K928-cleaved β is completely gone in this case. Both 13 subunits are completely absent with the DS1/R879A/R925A mutant.

Example 1. Deletion of Spacer-1 Results in GlcNAc-1-PT α/β Cleavage at an Alternate Site In order to analyze the function of the spacer-1 domain of the α/β subunit of GlcNAc-1-PT, an alignment between the human and *D. discoideum* GlcNAc-1-PT protein sequence and the bacterial N-acetylglucosamine-1-phosphate transferase sequence was initially performed. As shown in FIG. 6, the human spacer-1 sequence is 200 aa longer than that of the *D. discoideum* and bacterial proteins, as is the case with all mammalian GlcNAc-1-PT spacer-1 regions for which sequence data is available. This suggested that the mammalian spacer-1 region could play a unique role not associated with the *D. discoideum* spacer-1 sequence. Hence the 236 aa human spacer-1 sequence was replaced with 29 aa of the *D. discoideum* sequence at the DNA level and the resulting construct (FIG. 1A, DS1) was transfected into GNPTAB$^{-/-}$ HeLa cells generated by the CRISPR/Cas9 method (3). Western blot analysis of whole cell extracts expressing the WT and DS1 mutant was performed to determine if replacement of human spacer-1 with the *D. discoideum* sequence allowed for efficient folding of the mutant protein and its exit from the endoplasmic reticulum (ER) to the cis-Golgi where the α/β precursor is cleaved to the α and β subunits. As shown in FIG. 1B and FIG. 1C, the mutant protein is indeed expressed well, exits the ER, and exhibits 60% of WT catalytic activity toward the simple sugar αMM. However, the bulk of the β subunit product of the proteolytic cleavage migrated slower on an SDS-PAGE gel than the WT β subunit (FIG. 1B, arrowhead), indicating that most of the β in DS1 mutant is being cleaved at an alternate site relative to the WT protein which is cleaved at K928 (FIG. 1B, *). A small amount of the normal β subunit was also seen with DS1 (FIG. 1B and FIG. 1D, longer exposure, *). This raised the question as to whether the alternate cleavage resulting from removal of spacer-1 is due to the same protease, S1P, that cleaves WT α/β precursor at K928, or if a different protease may be involved. To address this issue, we treated cells with an inhibitor of S1P, the aminopyrrolidineamide PF-429242 (9). The presence of the inhibitor resulted in loss of the β subunit formation in both the WT GlcNAc-1-PT and the DS1 mutant (FIG. 1D), demonstrating that cleavage at the alternate site is mediated by S1P. If this is the case, an additional consensus S1P cleavage site should exist N-terminal to the original cleavage site. An examination of GlcNAc-1-PT α/β amino acid sequence revealed this to be true with the consensus key arginine residue, R879, occurring at the invariant −4 position, and cleavage postulated to occur at Q882 (FIG. 1E) (10). Cleavage at Q882 is consistent with the increase in molecular mass of the β subunit seen with DS1. Mutation of R925 abolishes cleavage of WT GlcNAc-1-PT at K928 (FIG. 1F, lane 2). Mutation of R879, on the other hand, did not affect the normal processing of the full-length α/β precursor at K928 (FIG. 1F, lane 3), but abolished cleavage at Q882 for the DS1 mutant, as shown by loss of the slower migrating β subunit (FIG. 1F, lane 6). The trace amount of K928 cleaved β in this case was not affected (FIG. 1F, lane 6, longer exposure). Mutation of both R925 and R879 resulted in complete loss of β formation (FIG. 1F, lane 7). These data clearly identify Q882 as a novel S1P cleavage site in GlcNAc-1-PT that is rarely utilized except in the absence of spacer-1 (FIG. 7).

Figure 8A:
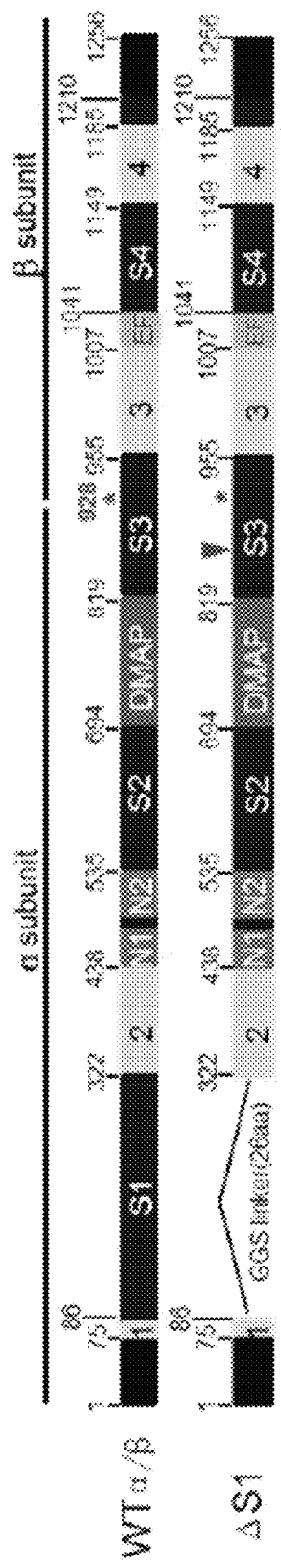
FIG. 8A depicts a schematic of GlcNAc-1-PT α/β subunit modular arrangement and replacement of the human spacer-1 sequence with a 26 aa linker sequence comprising of Gly and Ser residues.
Figure 8B:
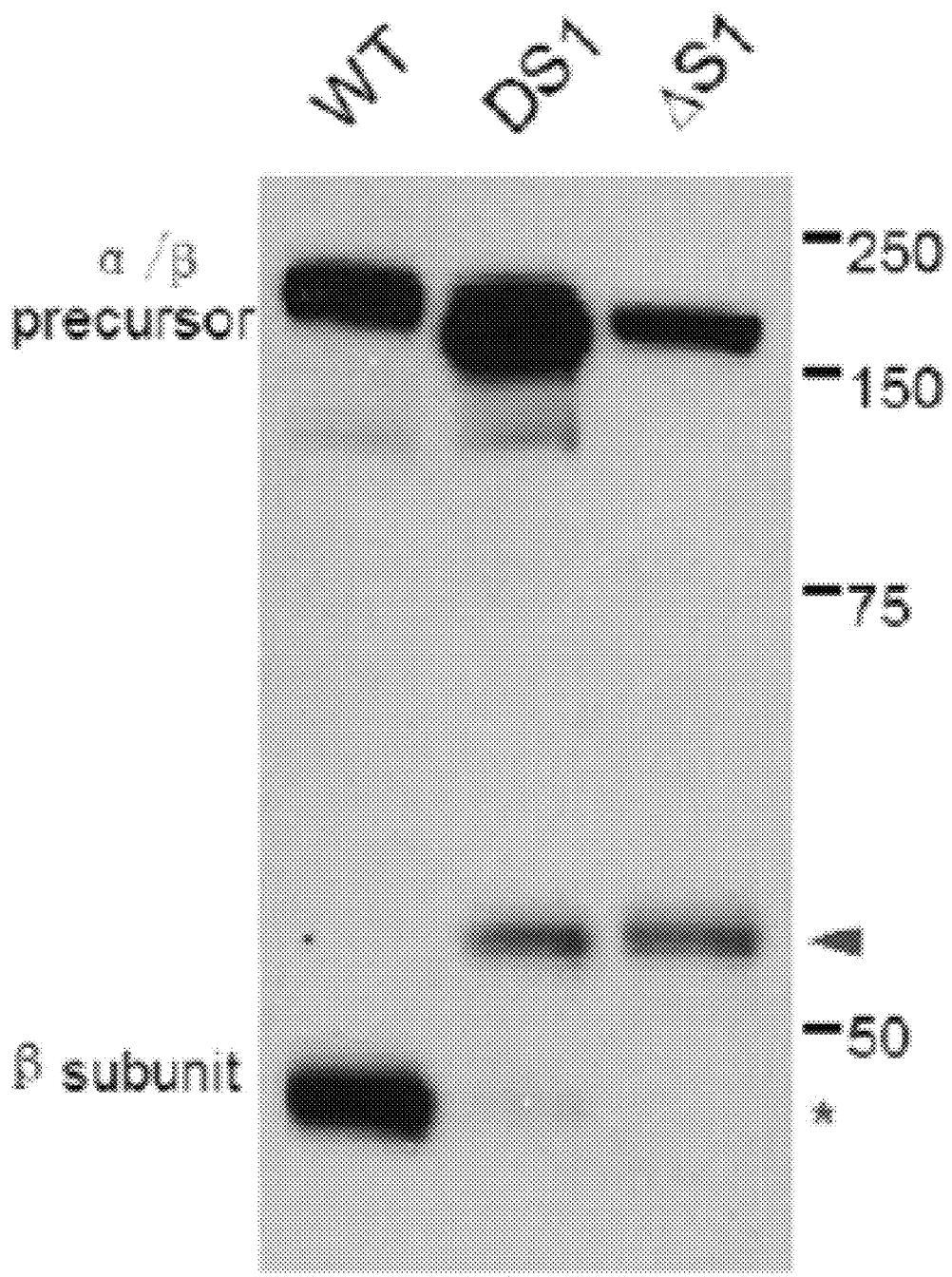
FIG. 8B depicts immunoblot analysis of WT α/β versus the DS1 and ΔS1 deletion mutants expressed in GNPTAB$^{-/-}$ HeLa cells and probed with anti-V5 antibody.
Figure 8C:
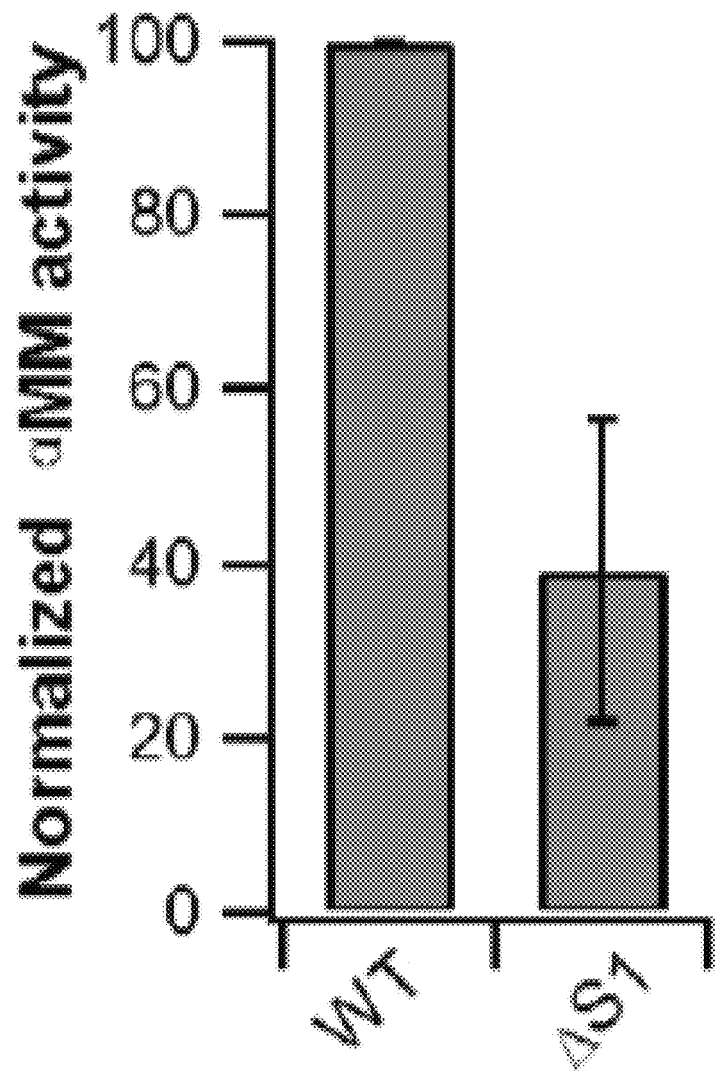
FIG. 8C depicts a graph showing phosphotransferase activity toward the simple sugar αMM, using extracts of GNPTAB$^{-/-}$ cells transfected with WT α/β precursor or the ΔS1 mutant cDNA. Activity was normalized to total protein concentration.
Figure 8D:
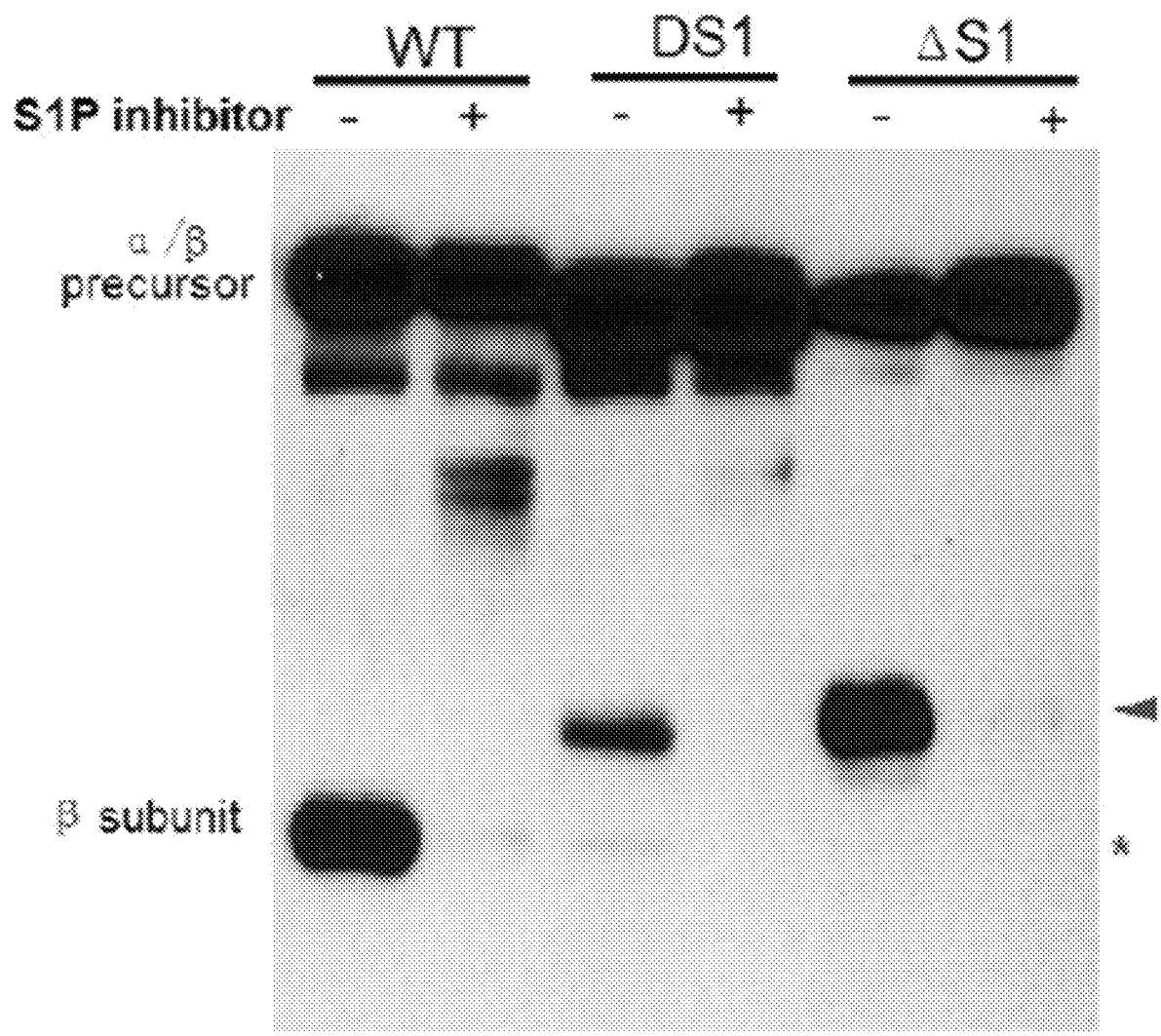
FIG. 8D depicts an immunoblot showing inhibition of S1P activity of GNPTAB$^{-/-}$ HeLa cells transfected with either WT α/β precursor, the DS1 or the ΔS1 mutant cDNA. 24 h post-transfection, PF-429242 was added to the cells at a final concentration of 10 μM and cells were incubated for a further 24 h before being harvested. Cells extracts were prepared and 20 μg of each lysate was separated by SDS-PAGE and subject to Western blotting.
Figure 9:
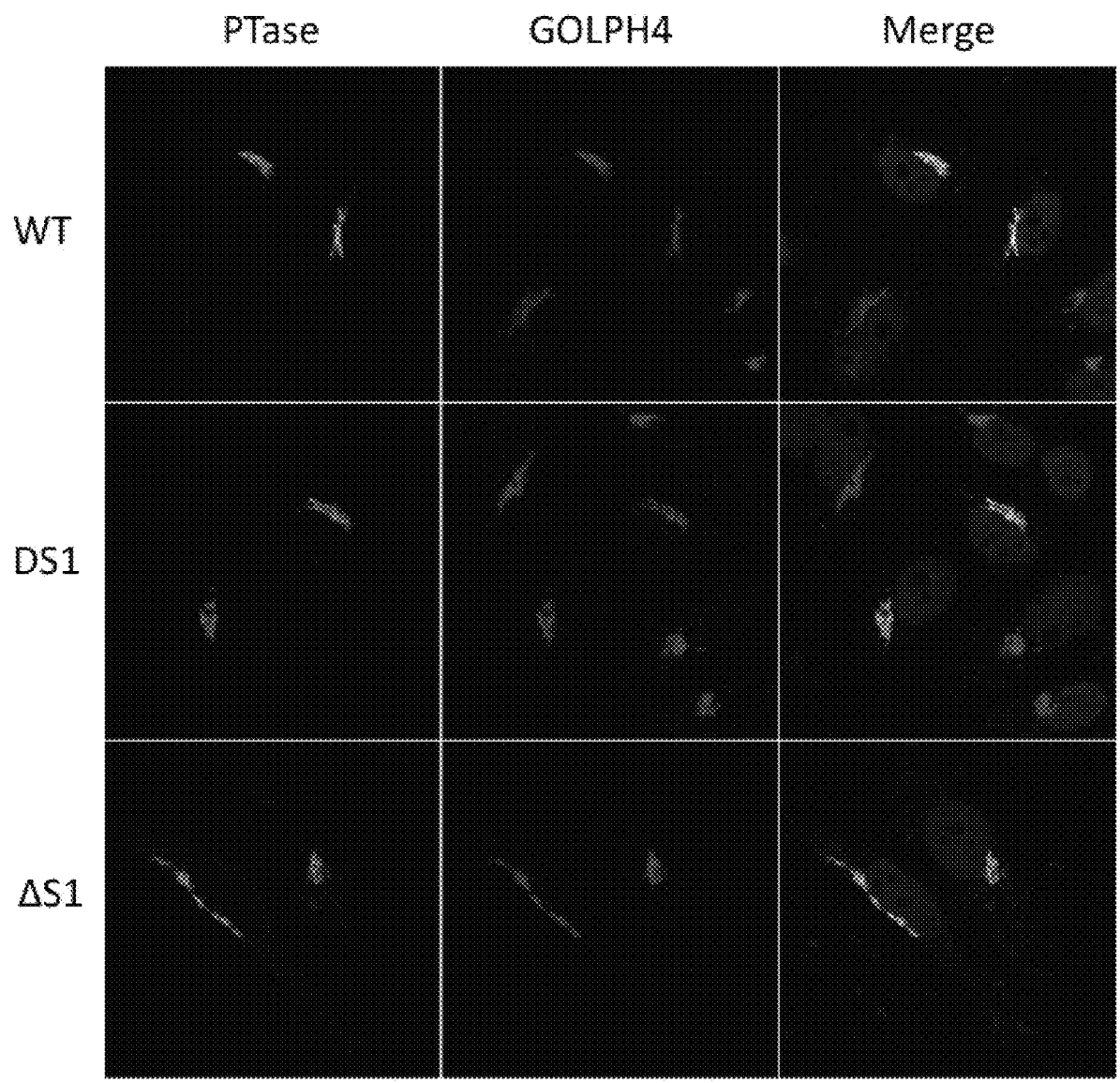
FIG. 9 depicts confocal immunofluorescence images of GNPTAB$^{-/-}$ HeLa cells transfected with either WT α/β precursor, the DS1 or the ΔS1 mutant cDNA, and colocalized with the Golgi markers GOLPH4, respectively (see Methods).

Since the 236 aa human spacer-1 sequence was replaced with the 29 aa *D. discoideum* sequence, it was possible that utilization of the alternate cleavage site is a consequence of introducing the *D. discoideum* sequence as opposed to removal of the human spacer-1 sequence. To exclude this possibility, another spacer-1 deletion mutant was made in which human spacer-1 was replaced with a 26 aa linker comprising of the small residues Gly and Ser (FIG. 8A, ΔS1). Δspacer-1 (ΔS1) behaved in every respect similar to DS1 in that the proteolytic processing mediated by S1P resulted in cleavage for the most part at the new site (Q882) (FIG. 8B), and ΔS1 had 40% of WT activity toward αMM (FIG. 8C). Moreover, the S1P inhibitor, PF-429242, blocked formation of the β subunit with ΔS1 as it did with WT and the DS1 mutant of GlcNAc PT (FIG. 8D). Also, both DS1 and ΔS1 showed identical Golgi localization to WT GlcNAc-1-PT (FIG. 9), ruling out mislocalization of these two mutants as a possible cause for the altered cleavage. These results unequivocally show that the presence of the 236aa spacer-1 sequence in human GlcNAc-1-PT ensures cleavage at K928 instead of Q882.

Example 2. Cleavage at Q882 Results in an Inactive GlcNAc-1-PT

Figure 1G:
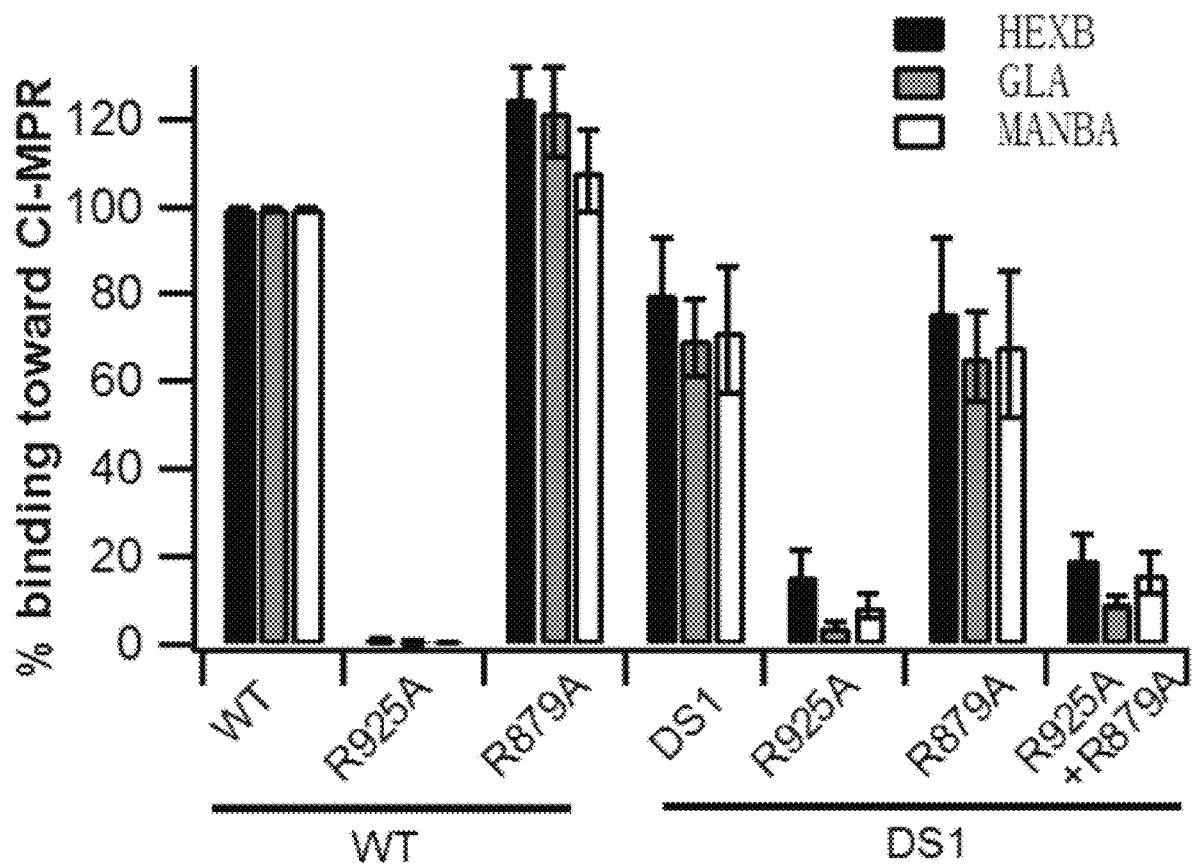
Figure 10:
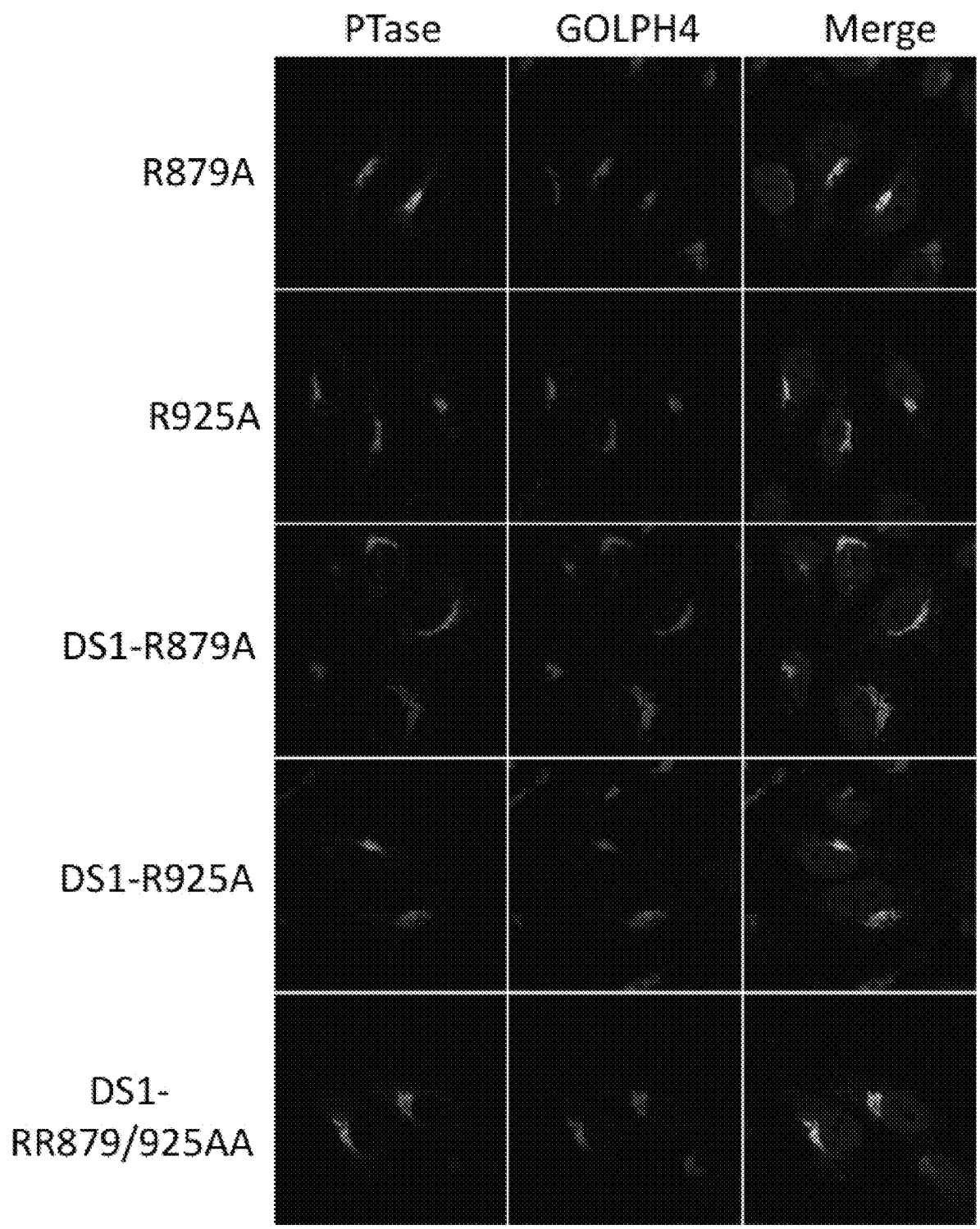
FIG. 10 depicts confocal immunofluorescence images of GNPTAB$^{-/-}$ HeLa cells transfected with either WT α/β precursor, or the indicated mutant cDNAs, and colocalized with the Golgi markers GOLPH4, respectively (Methods).

Proteolytic processing of GlcNAc-1-PT α/β precursor in the Golgi at residue K928 is imperative for a catalytically active enzyme (5, 11). Since there are two S1P cleave sites in α/β, this begs the question as to whether cleavage at the new site instead of at K928 also results in an active enzyme. In order to address this question, the activity of the point mutants shown in FIG. 1F toward αMM (FIG. 1C) and a number of lysosomal enzymes, (FIG. 1G) were tested, both in the context of WT GlcNAc-1-PT α/β precursor as well as the DS1 mutant. The various constructs were expressed in GNPTAB$^{-/-}$ HeLa cells and 48 h post-transfection, cells extracts were prepared and an aliquot of each was saved to perform the αMM activity assay (FIG. 1C). The remaining extracts were incubated with beads containing immobilized cation-independent (CI)-MPR to bind the lysosomal enzymes that had been phosphorylated. The beads were washed and assayed for the extent of binding of three lysosmal enzymes as described in Methods (FIG. 1G). As shown in FIG. 1C and FIG. 1G, the R925A mutant in the context of WT α/β precursor had only background activity toward both αMM and lysosomal enzymes, in concordance with the prevailing hypothesis that cleavage of the α/β precursor is imperative for activity. R879A/WT, on the other hand, exhibited 30% of the activity toward αMM and between 110-125% of the activity toward the three lysosomal enzymes compared to the WT α/β precursor. When these point mutations were tested individually or together in the DS1 background, the various mutants still retained 20-30% of WT αMM activity (FIG. 1C). The fact that the R925A/R879A/DS1 mutant, which is not proteolytically processed at all, retained substantial activity toward αMM (FIG. 1C) and low levels of activity toward lysosomal enzymes (FIG. 1G) indicates that uncleaved α/β in the absence of spacer-1 is partially active. All mutants displayed Golgi localization identical to WT (FIG. 10). These results show that the catalytic activity toward lysosomal enzymes associated with DS1 is due to a combination of the small amount of β originating from cleavage at K928 plus the activity contributed by the α/β precursor, with the major form of β that is cleaved at Q882 being inactive.

Figure 2A:
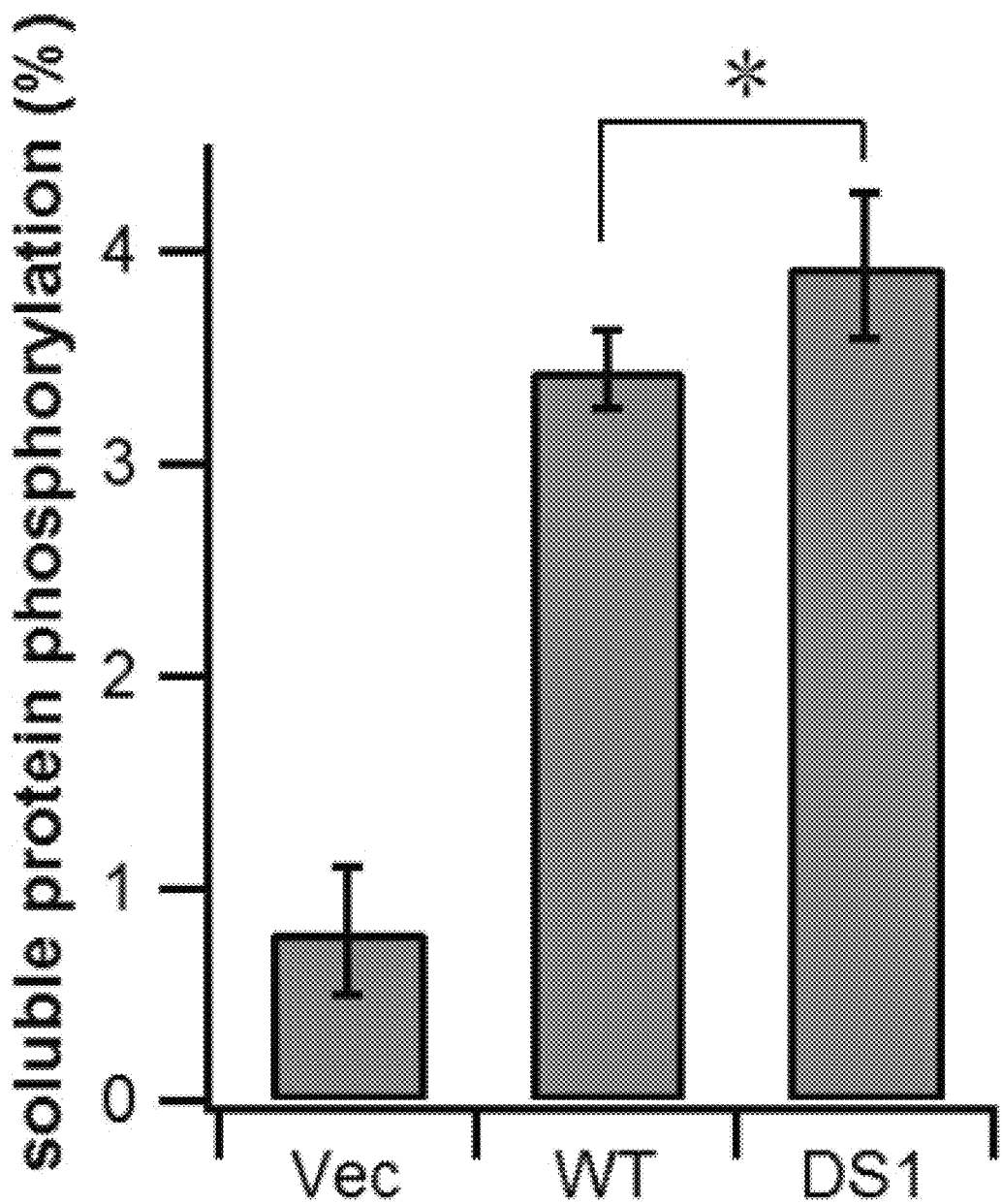
FIG. 2A, FIG. 2B and FIG. 2C depict graphs and an immunoblot showing that the deletion of spacer-1 enhances phosphorylation of several non-lysosomal glycoproteins.
Figure 2B:
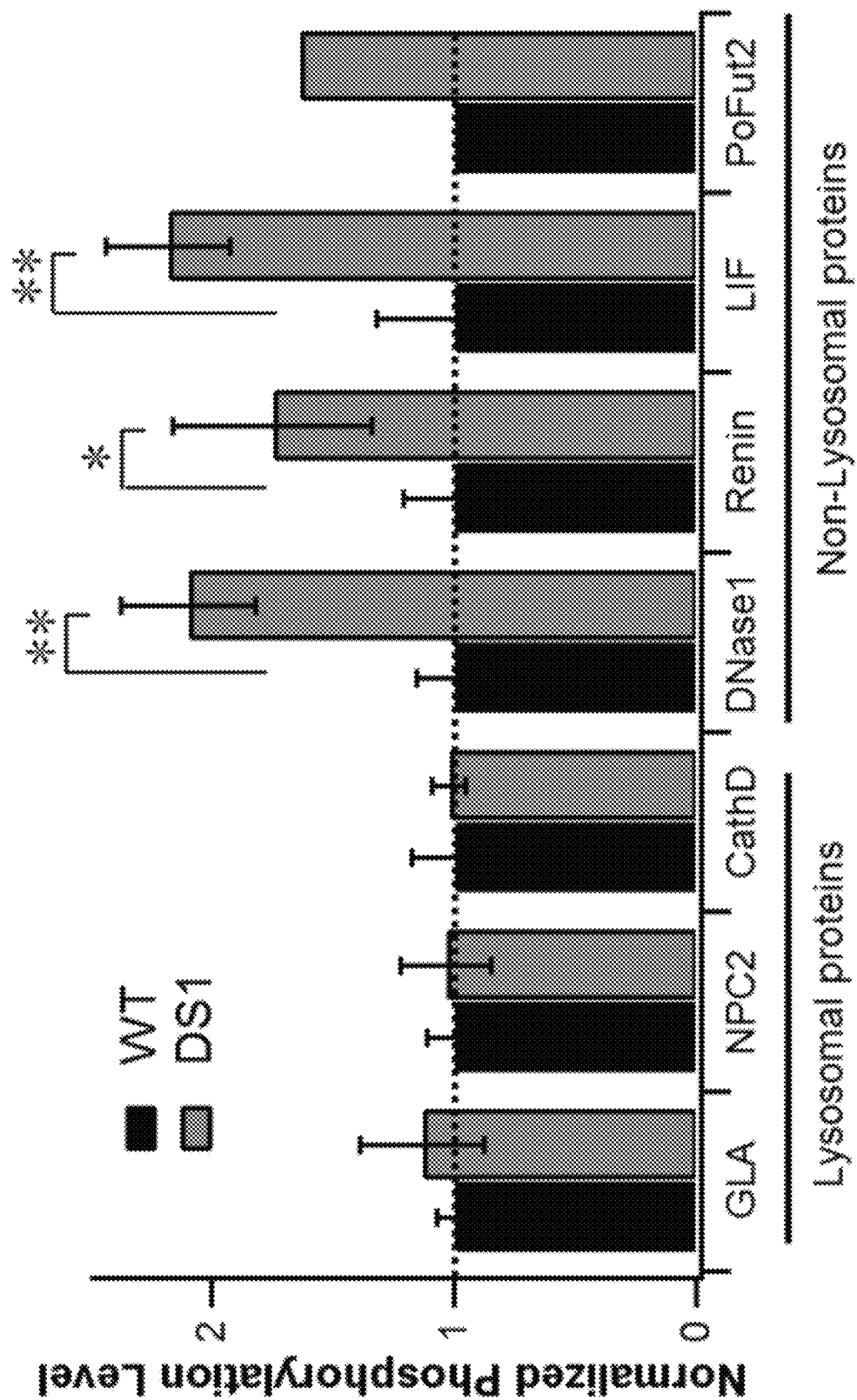
Figure 2C:
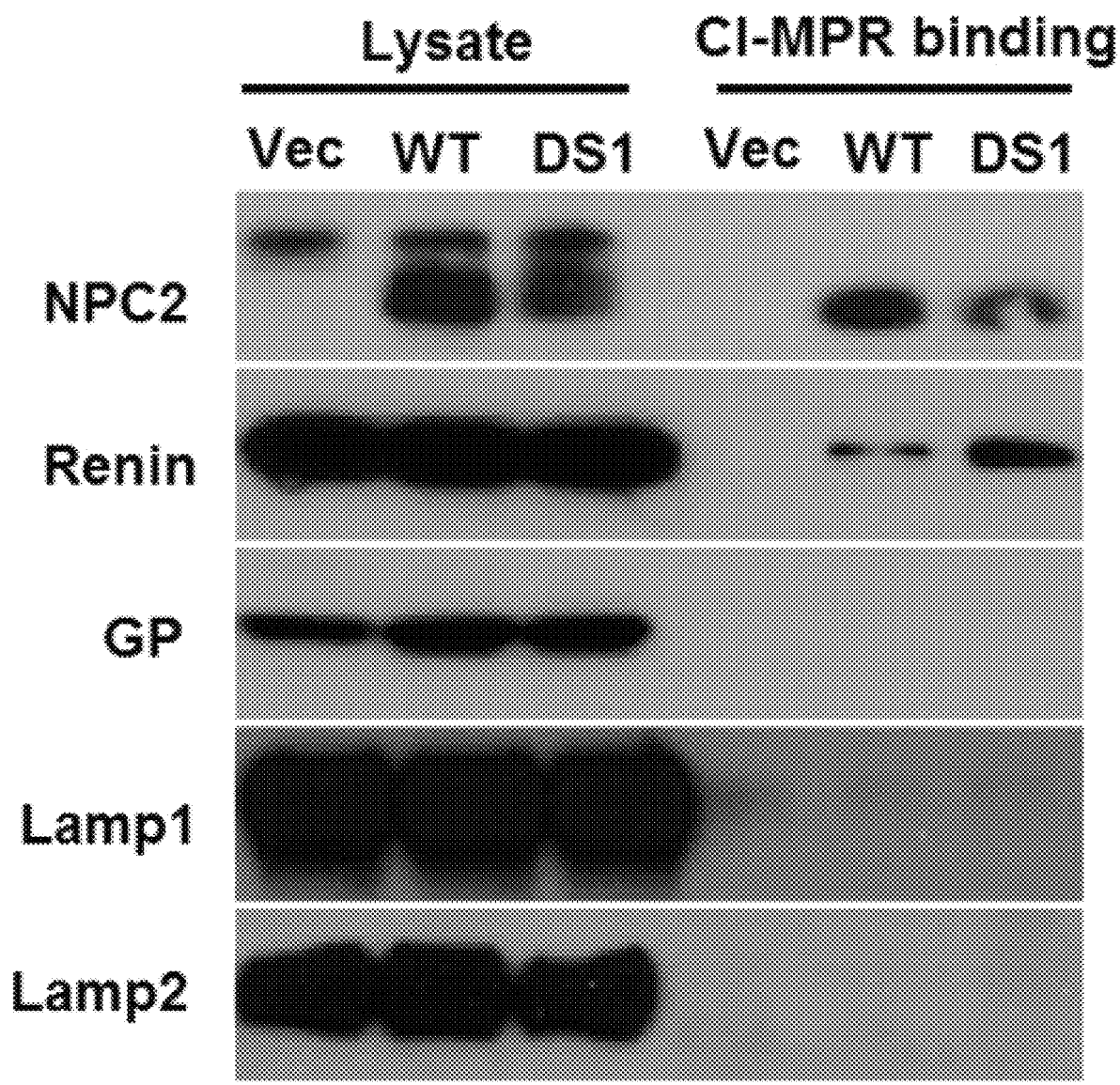

Example 3. Deletion of Spacer-1 Enhances Phosphorylation of Several Non-Lysosomal Glycoproteins The total mannose phosphorylation of soluble glycoproteins in GNPTAB$^{-/-}$ HeLa cells transfected with WT or the DS1 mutant construct, or with vector alone was determined. 48 h post-transfection, the cells were labeled for 2 h with [2-$^3$H]mannose, and then harvested, washed and lysed in detergent-free buffer followed by ultracentrifugation to separate membrane proteins from the soluble fractions. The soluble fractions were then incubated with immobilized CI-MPR to specifically bind the Man-6-P modified proteins, and then analyzed for their content of [2-$^3$H]mannose-labeled glycoproteins as described under Methods. Surprisingly, after subtraction of the vector-alone value, the DS1 mutant consistently gave a small but statistically significant increase in the level of phosphorylation of total soluble glycoproteins compared to the WT construct (FIG. 2A). The degree of phosphorylation of the lysosomal proteins, GalA, Cathepsin D (CathD), and Niemann-Pick disease, type C2 (NPC2) by either WT or DS1 was also measured using [2-$^3$H]mannose-labeling, immunoprecipitation and direct glycan analysis as described in Methods. All three lysosomal enzymes showed a similar degree of phosphorylation irrespective of whether WT or the DS1 construct was co-transfected into the GNPTAB$^{-/-}$ HeLa cells along with expression vectors for the individual enzymes (FIG. 2B, left panel, WT value set at 1.0). Taken together, these findings raised the possibility that the observed increase in total phosphorylation by DS1 was due to phosphorylation of non-lysosomal glycoproteins in addition to lysosomal proteins. In order to determine if this was the case, cDNAs for the non-lysosomal glycoproteins DNase1, Renin, leukemia inhibitory factor (LIF) and protein O-fucosyltransferase 2 (PoFUT2) were co-transfected along either WTα/β precursor or the DS1 mutant cDNA, and the degree of phosphorylation quantitated by [2-$^3$H]mannose-labeling. These glycoproteins were selected for analysis since they were known to acquire low levels of the Man-6-P tag although they are not lysosomal proteins by nature (12-15). In all four cases, the extent of mannose phosphorylation mediated by DS1 was 1.5-2 fold higher than that achieved with the WT construct (FIG. 2B, right panel). Consistent with this, Renin but not NPC2 displayed increased binding to immobilized CI-MPR when the cDNAs for these two proteins were co-transfected with DS1 relative to WT α/β precursor (FIG. 2C). Neither glycopepsinogen (GP) nor the membrane glycoproteins, Lamp1 and Lamp2, showed any binding under these conditions (FIG. 2C). These results show that in the absence of spacer-1, the phosphorylation mediated by the modified α/β subunits of a subset of non-lysosomal substrates is increased. Together, these data demonstrate that spacer-1 dictates that cleavage of the GlcNAc-1-PT α/β precursor occurs almost exclusively at K928, and functions to minimize phosphorylation of a number of non-lysosomal glycoproteins.

Figure 3B:
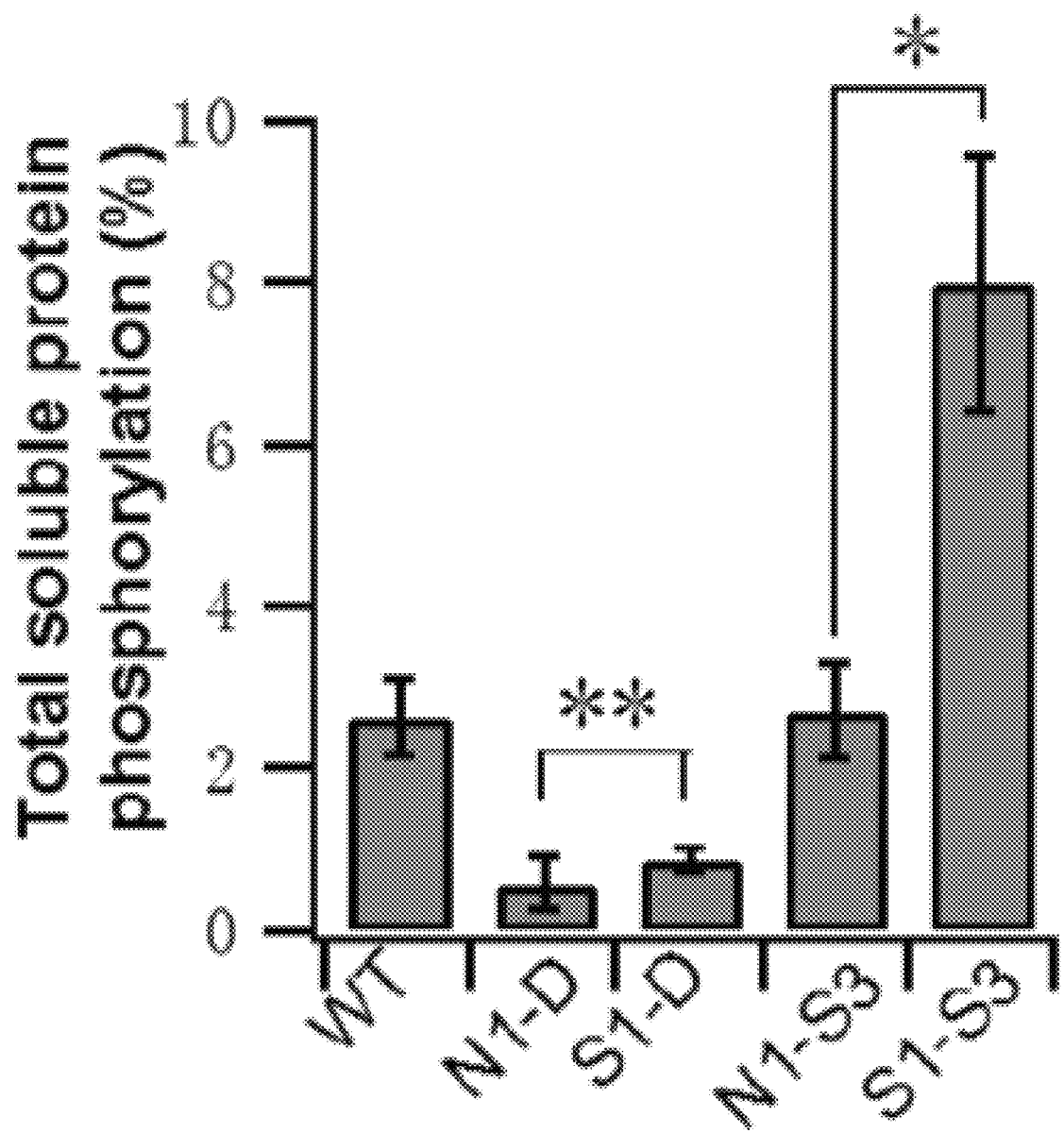
Figure 3C:
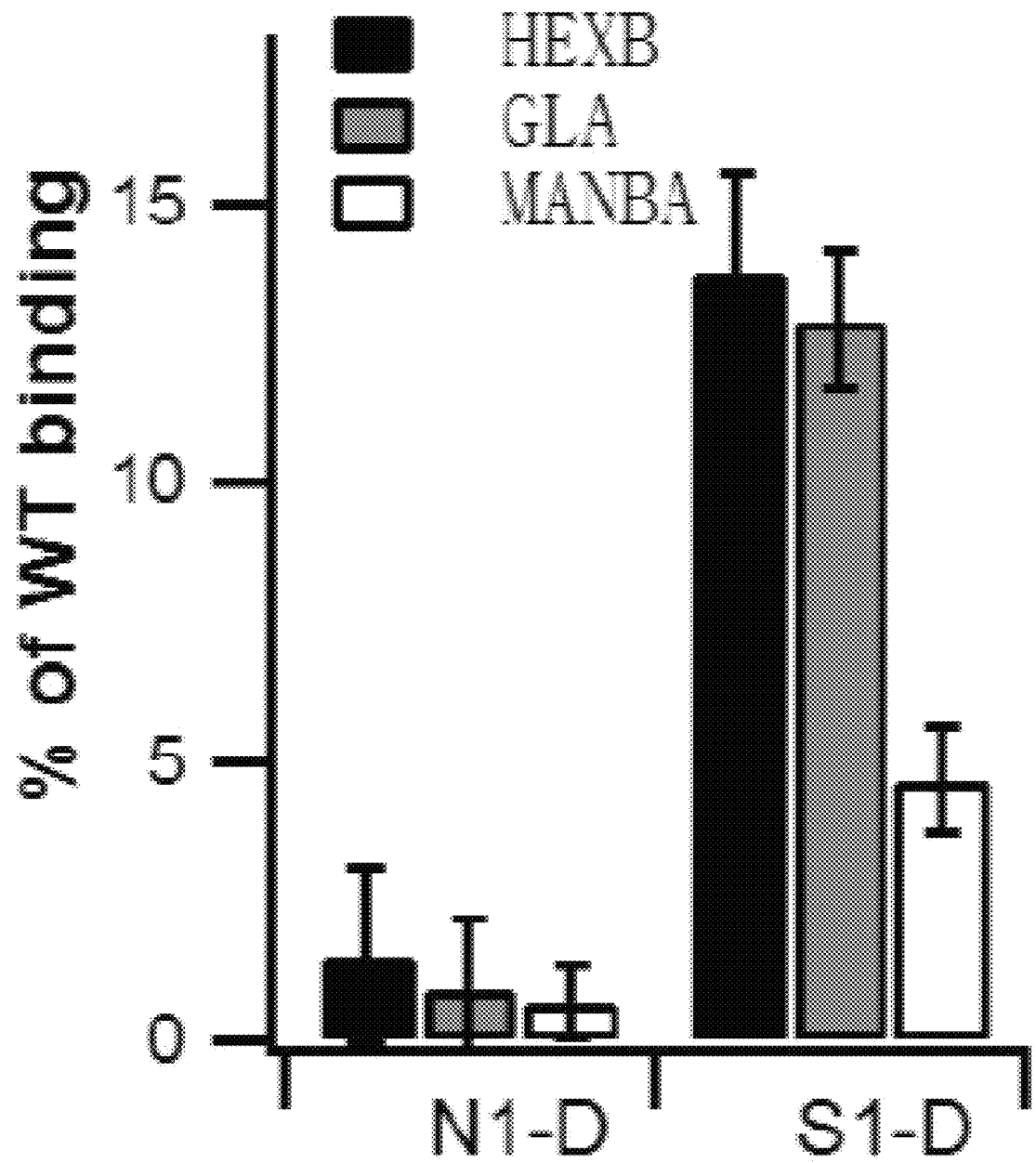

Example 4. Deletion of Amino Acids 438-926 Results in High Level Expression of an Active GlcNAc-1-PT It was previously showed that the two Notch repeats along with the DMAP interaction domain of the a subunit mediate the selective recognition of lysosomal enzymes (FIG. 3A, WT α/β). Deletion of this region (FIG. 3A, N1-D) dramatically reduced the phosphorylation of total soluble glycoproteins as determined by [2-$^3$H]mannose-labeling (FIG. 3B). Given that the majority of proteins phosphorylated by GlcNAc-1-PT are in fact lysosomal proteins, this outcome in the absence of the N1-D region is not surprising. Accordingly, phosphorylation of β-hexosaminidase (HEXB), α-Galactosidase (GLA), and β-Mannosidase (MANBA), as measured by the ability to bind to immobilized CI-MPR, was almost completely abrogated (FIG. 3C). In light of the finding that spacer-1 acts as an inhibitory domain, it was hypothesized that deleting spacer-1 in combination with N1-D (FIG. 3A, S1-D) may partially overcome the inability of GlcNAc-1-PT lacking the two Notch modules and the DMAP interaction domain to phosphorylate lysosomal enzymes. This prediction is borne out by the results showing a small but statistically significant increase in phosphorylation of total soluble proteins mediated by the S1-D mutant relative to N1-D (FIG. 3B, compare N1-D vs S1-D), as well as a small increase in phosphorylation of HEXB, GLA, and MANBA (14%, 13% and 5%, respectively of WT values) (FIG. 3C). Since the activity of the N1-D and S1-D mutants toward the simple sugar αMM is similar (FIG. 3E, N1-D vs S1-D), these increases in lysosomal enzyme phosphorylation mediated by the S1-D deletion mutant are best explained by the loss of the inhibitory function of spacer-1.

Figure 3D:
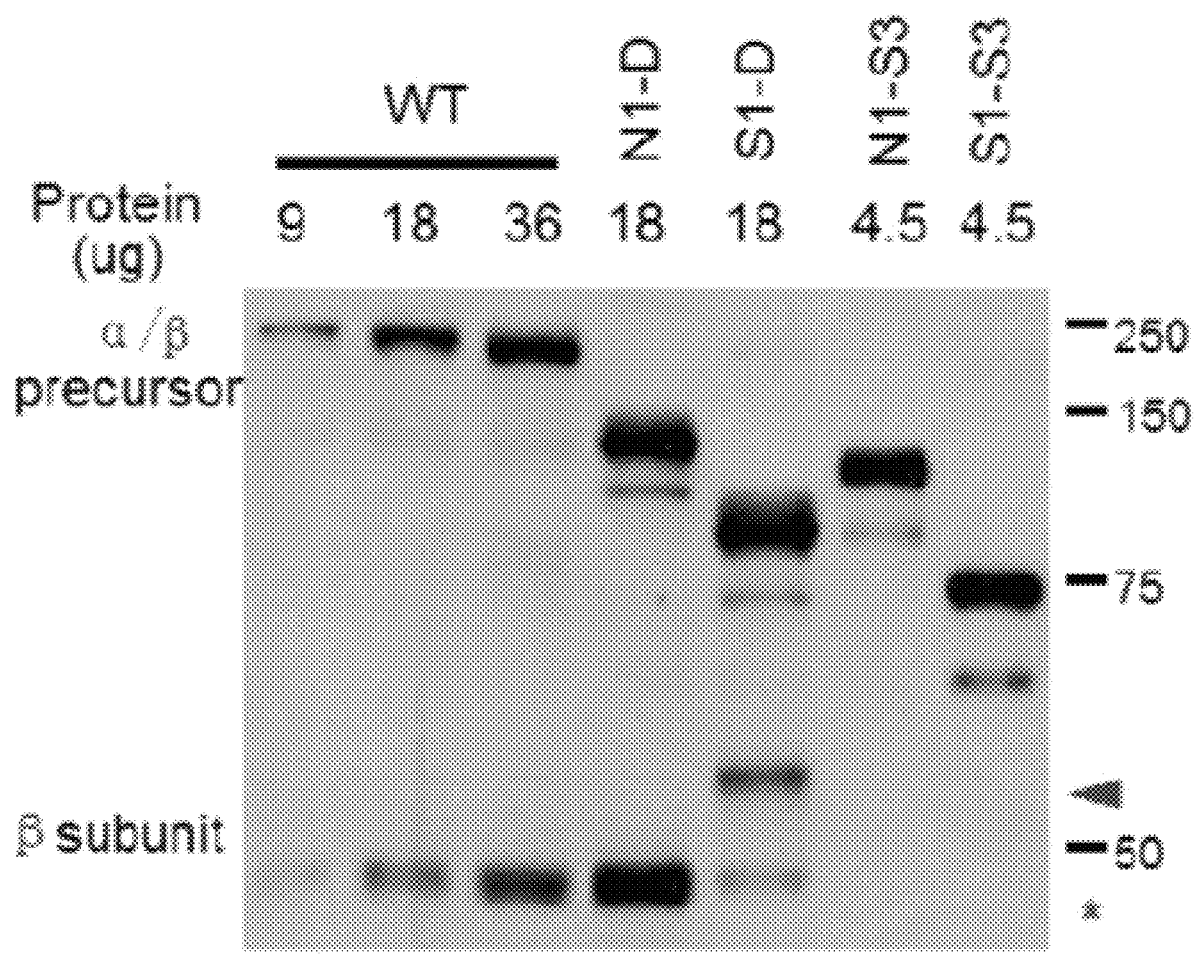
Figure 3E:
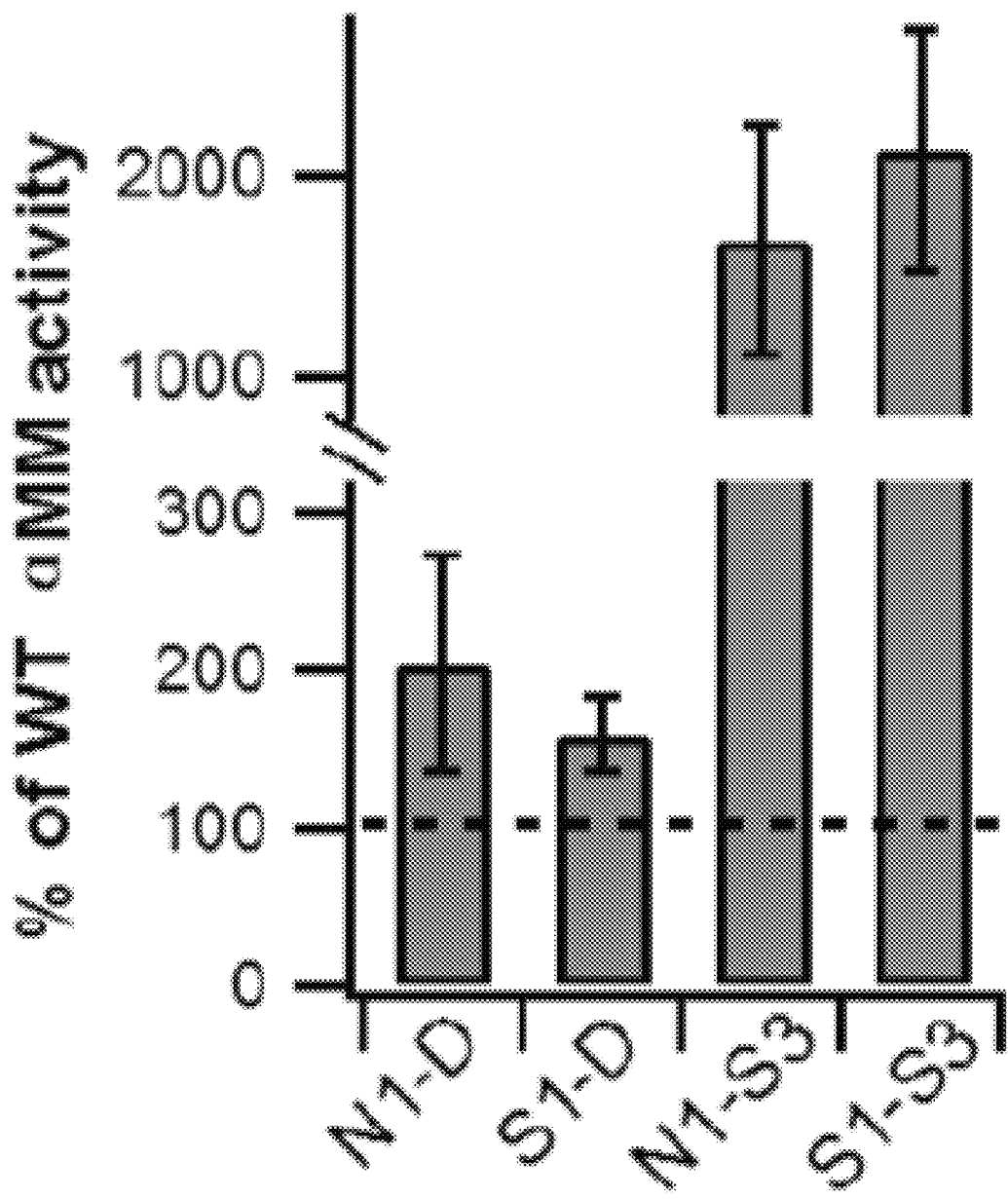

Additional domains from GlcNAc-1-PT α/β precursor were deleted and still retain catalytic activity was checked. Deletion of all aa from the beginning of Notch 1 (C438) through K928, which included the majority of spacer-3, resulted in a truncated form of GlcNAc-1-PT (FIG. 3A, N1-53) that was expressed approximately 10-fold greater than WT in the GNPTAB$^{-/-}$ HeLa cells (FIG. 3D, compare lanes 3 and 6), and in spite of the absence of the two Notch repeats and the DMAP interaction domain, this mutant restored total phosphorylation of soluble glycoproteins to WT levels (FIG. 3B, compare WT vs N1-S3). The mutant did not undergo proteolytic processing since the region deleted extended to the cleavage site (FIG. 3D), yet it displayed dramatically increased catalytic activity toward the simple sugar αMM (FIG. 3E). This result showed that cleavage of the α/β precursor is not a requirement per se for catalytic activity. Deletions beyond K928 were not tolerated.

Figure 3F:
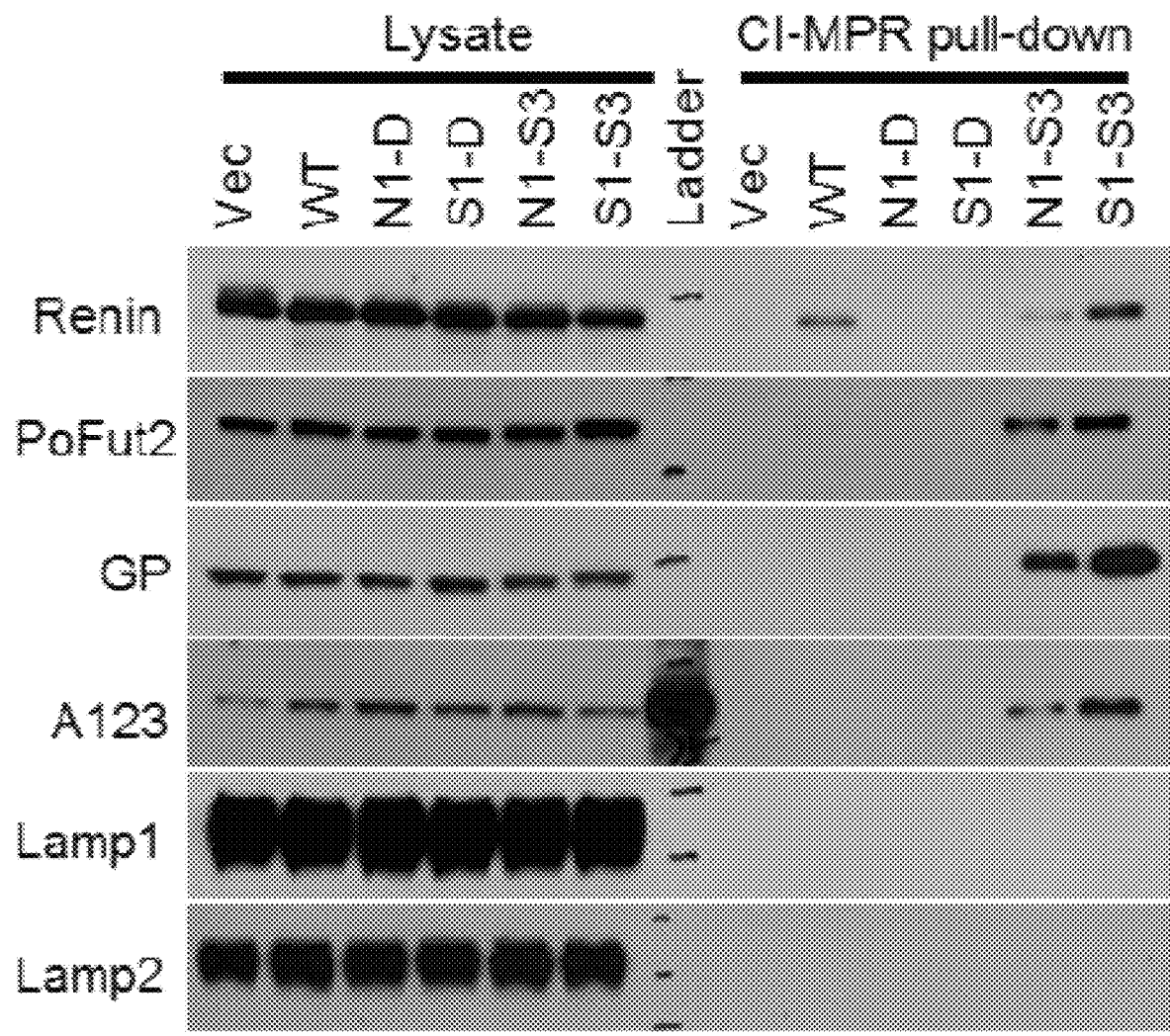
Figure 3G:
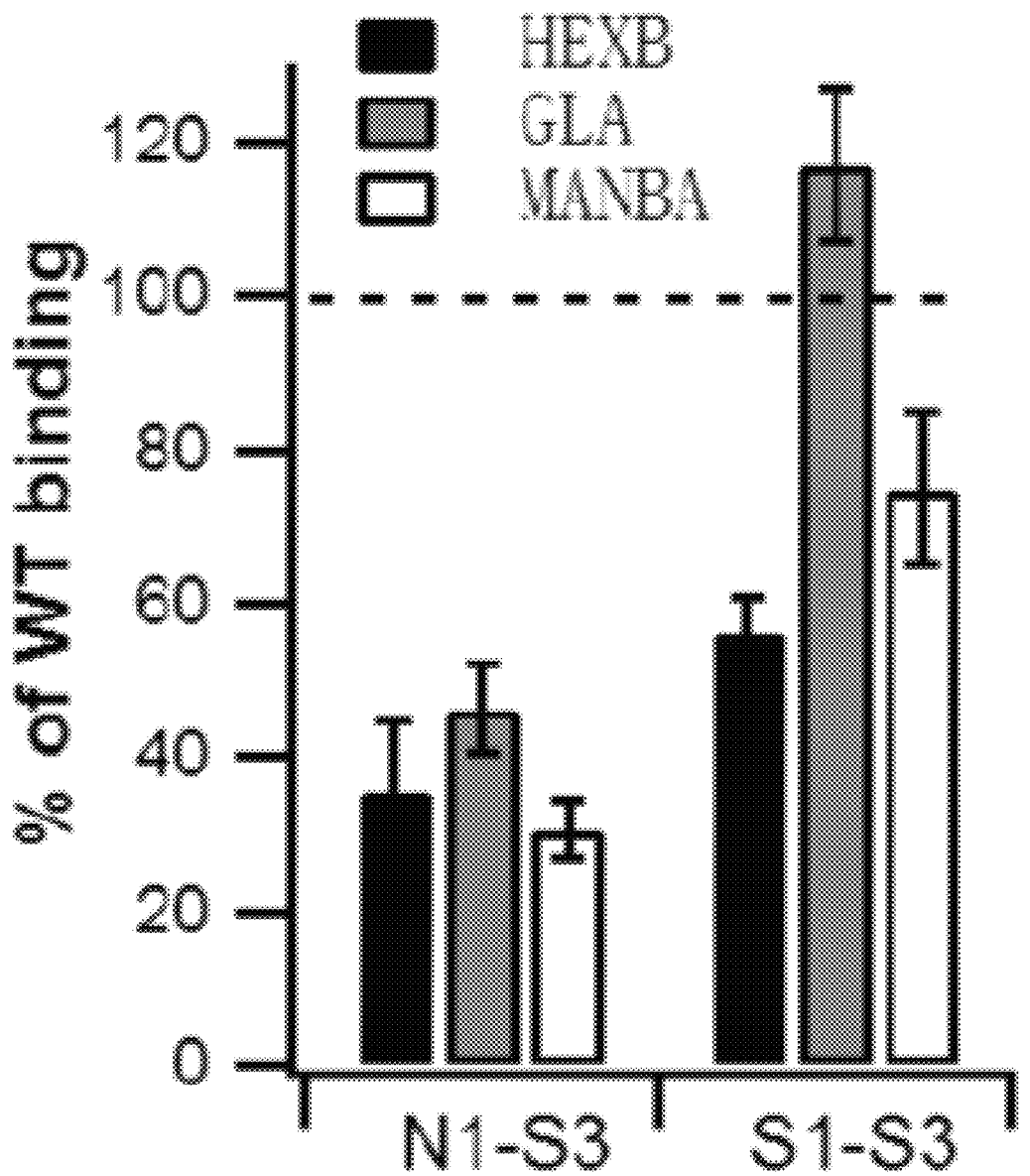
Figure 11:
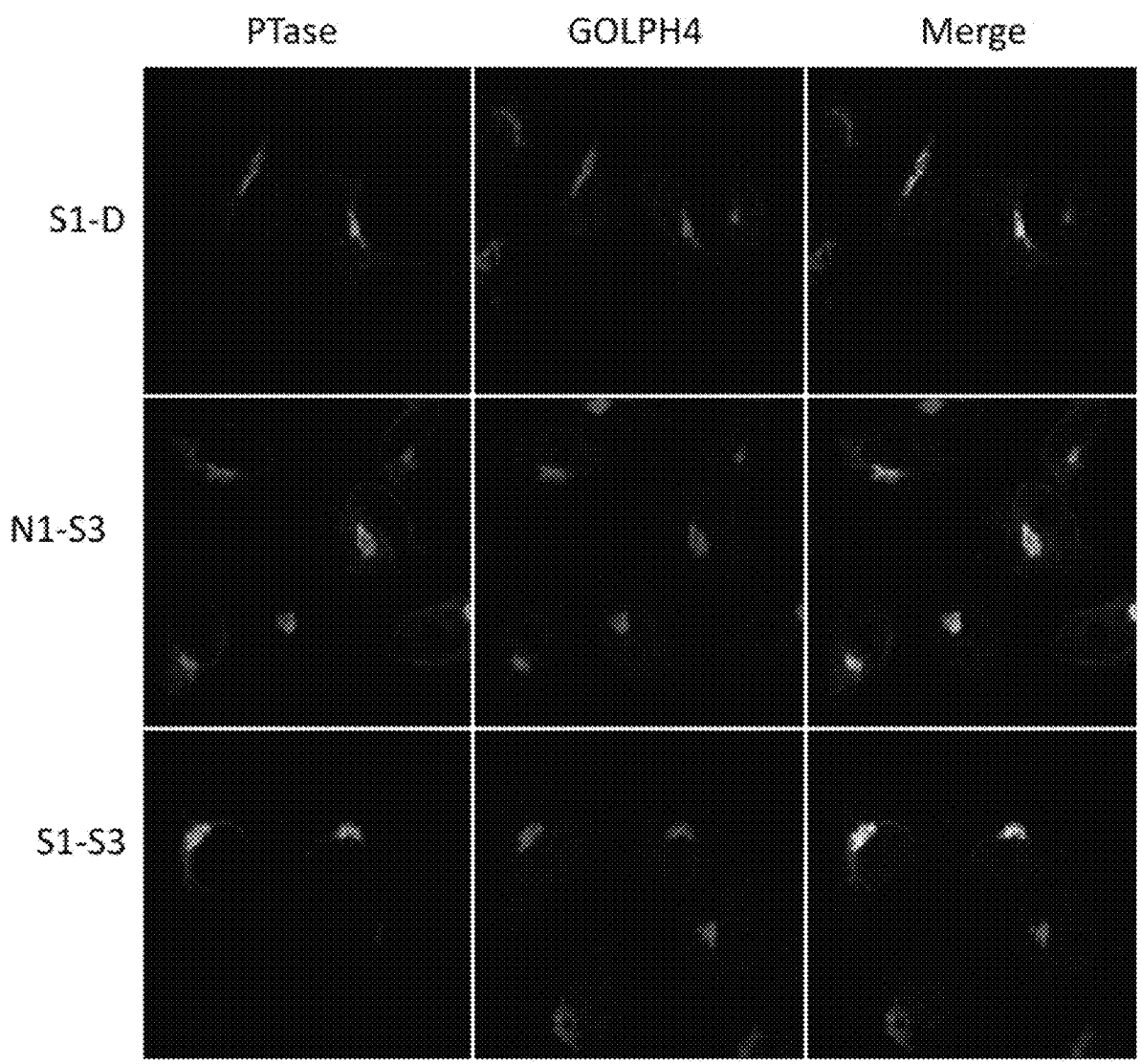
FIG. 11 depicts confocal immunofluorescence images of GNPTAB$^{-/-}$ HeLa cells transfected with either WT α/β precursor, the N1-S3 or the S1-S3 mutant cDNA, and colocalized with the Golgi markers GOLPH4, respectively (see Methods).

The outcome of deleting spacer-1 in the context of N1-S3 was determined. This new construct (FIG. 3A, S1-S3) resulted in a further truncated form of GlcNAc-1-PT α/β precursor that also displayed dramatically enhanced expression (FIG. 3D, compare lanes 3 and 7) and catalytic activity toward αMM, at levels similar to N1-S3 (FIG. 3E). Most notably, the total phosphorylation of soluble glycoproteins mediated by S1-S3 was increased more than 3-fold over WT, whereas N1-S3 was similar to WT (FIG. 3B, compare WT, N1-53 and S1-53). Since the only difference between S1-53 and N1-S3 is the absence of spacer-1, these results provide further evidence for an inhibitory role for spacer-1. The phosphorylation mediated by S1-S3 of the non-lysosomal proteins Renin, PoFut2, GP, and the von Willebrand factor A1A2A3 domains was also increased relative to N1-53 (FIG. 3F), as was the case with the lysosomal proteins HEXB, GLA, and MANBA (FIG. 3G). All four mutants (N1-D, S1-D, N1-53, and S1-53) localized to the Gogi, similar to WT (FIG. 11).

Figure 4:
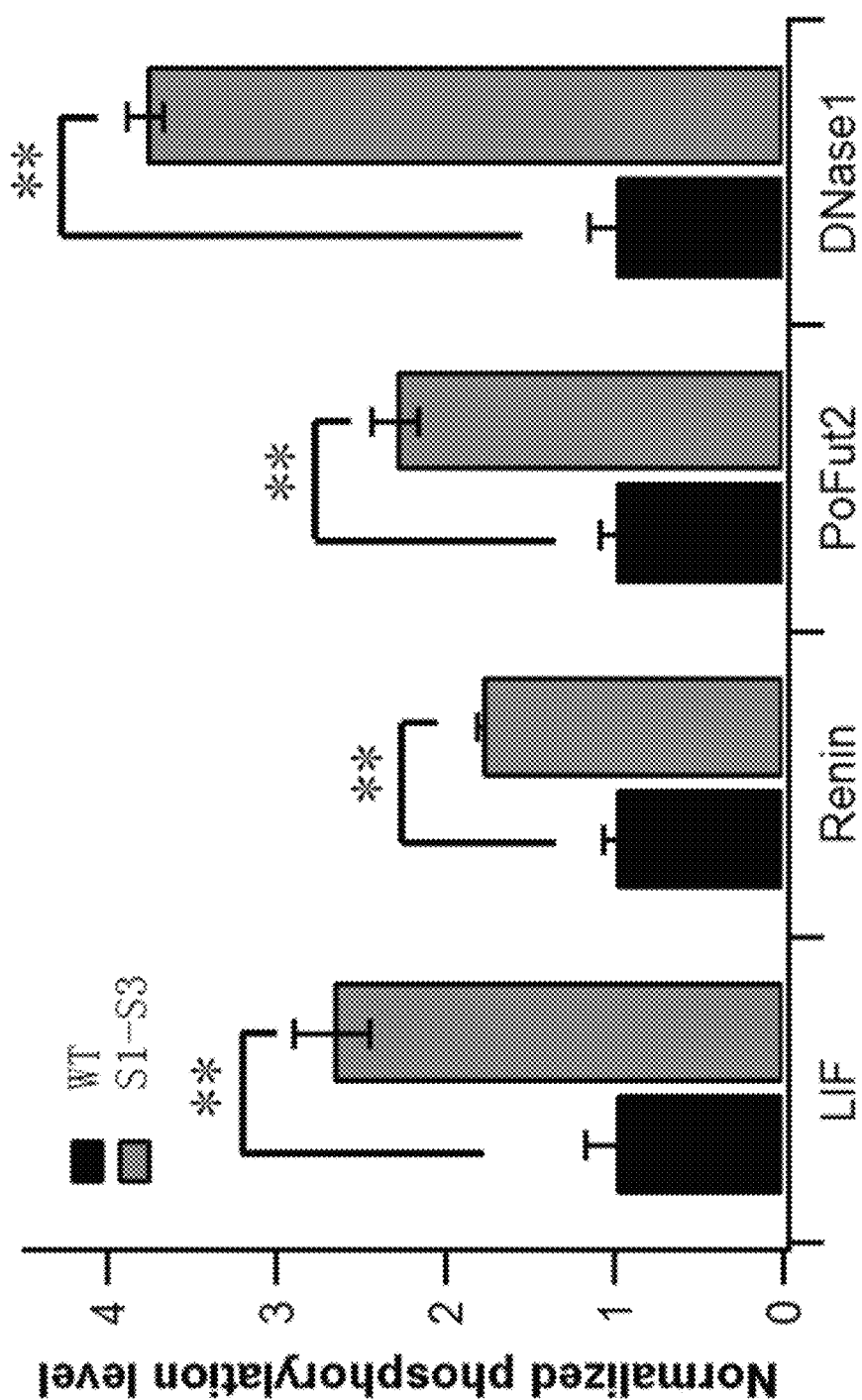
FIG. 4 depicts a graph showing that phosphorylation of non-lysosomal glycoproteins is mediated by the minimal α/β precursor. GNPTAB$^{-/-}$ HeLa cells were co-transfected with either WT α/β precursor or the S1-S3 deletion mutant cDNA, along with expression plasmids for the 4 non-lysosomal glycoproteins. 48 h post-transfection, cells were labeled for 2 h with [2-$^3$H]-mannose, followed by immunoprecipitation of the proteins secreted into the media and determination of the percent N-glycans containing Man-6-P. Values obtained with WT are set to 1. The absolute values of phosphorylation for the indicated proteins coexpressed with WT α/β precursor were: LIF, 26±5%; Renin, 22±2%; PoFut2, 26±2%, DNase I, 22±3%.

In order to obtain more quantitative measurements of the degree of Man-6-P formation mediated by the S1-S3 mutant, [2-$^3$H]mannose-labeling of cells cotransfected with cDNAs for either LIF, Renin, PoFut2, and DNase 1 along with either WT GlcNAc-1-PT or the S1-53 mutant α/β precursor cDNA was performed. Coexpression of each of these proteins with S1-S3 resulted in a 2-4 fold increase in phosphorylation relative to WT (FIG. 4), in agreement with the markedly enhanced expression and concomitant increase in activity toward αMM (FIG. 3D and FIG. 3E). The phosphorylation of these proteins was slightly higher than achieved by the DS1 mutant (compare FIG. 4 to FIG. 2B).

Discussion for Examples 1-4

The Notch modules and DMAP interaction domain of GlcNAc-1-PT have essential roles in the selective recognition of lysosomal proteins and phosphorylation of their N-linked glycans (3, 16). Numerous other glycoproteins that traverse the secretory pathway present very similar or identical N-linked glycans which either do not get phosphorylated or acquire only low levels of the Man-6-P tag (17). The prevailing explanation for this observation is that unlike lysosomal proteins, non-lysosomal proteins lack the structural determinants that are recognized and bound by the Notch modules and/or DMAP interaction domain of GlcNAc-1-PT. Thus, the presence of a high mannose oligosaccharide on a protein in itself is insufficient for in vivo phosphorylation of the glycan by GlcNAc-1-PT. In vitro, GlcNAc-1-PT is able to phosphorylate the simple sugar, αMM, but the Km of the enzyme for this substrate is well over three orders of magnitude higher than that of a lysosomal enzyme, illustrating the key role of the protein docking sites on lysosomal proteins for GlcNAc-1-PT (18). A key finding of this study is that in addition to specifically recognizing and phosphorylating lysosomal proteins, GlcNAc-1-PT contains elements (spacer-1) that serve to prevent phosphorylation of non-lysosomal proteins. This is the first function assigned to the spacer-1 domain. Spacer-1 of human GlcNAc-1-PT is 236 aa long and is highly conserved among vertebrate species. It has a defined structure (PDB ID:2N6D), consistent with a role other than just serving as a "spacer" (19). The spacer-1 region of the lower eukaryote, D. discoideum, on the other hand, is similar in length to that of N. meningitidis bacterial N-acetylglucosamine-1-phosphate transferase (FIG. 6) and it is very unlikely that it functions in the same way as the human sequence. There is no significant identity at the aa level between the human and D. discoideum spacer-1 sequence. Since the flanking Stealth 1 & 2 domains are very similar between the two species, human GlcNAc-1-PT might tolerate substitution of the human sequence for the D. discoideum sequence. Expression of this chimera in GNPTAB$^{-/-}$ HeLa cells yielded an unexpected result in that DS1, though folded efficiently in the ER and transported to the cis-Golgi just like WT enzyme, was proteolytically processed differently in the latter compartment. That it was S1P that mediated this alternate cleavage was ascertained through the use of the S1P inhibitor PF-429242. In a recent study analyzing GlcNAc-1-PT patient mutations, Velho et al. reported that an in-frame deletion of residues Y937 to M972, resulted in cleavage of the α/β precursor by S1P at an alternate upstream site within the a subunit although the study did not identify the new site (20). The identification of Q882 as the alternate cleavage site is in agreement with the higher molecular mass of the p-subunit seen with DS1. The reason why S1P cleaves at Q882 rather than at K928 within the a subunit in the absence of spacer-1 is not clear at this point. In light of the finding that deletion of residues 937-972 also resulted in cleavage at the new site, one possibility is that spacer-1 interacts with some region of spacer-3 (aa 819-955, FIG. 1) and thereby influences where S1P cleaved. An alternate explanation for usage of the new site by S1P in the absence of spacer-1 is that the steric hindrance normally afforded by this domain to prevent cleavage at Q882 is no longer present, allowing S1P to now cleave primarily at Q882, although a small amount of precursor is also cleaved at K928. Interestingly, It was determined that WT GlcNAc-1-PT yields a trace amount of the catalytically inactive enzyme as a result of proteolytic processing at Q882. These results raise the possibility that vertebrate GlcNAc-1-PT acquired spacer-1 to facilitate cleavage at K928 and maximize its catalytic efficiency.

In addition to dictating the cleavage site utilized by S1P to generate the correctly processed form of GlcNAc-1-PT, the results also show spacer-1 to have an important role in minimizing phosphorylation of the high mannose glycans of non-lysosomal enzymes. It has been well documented that a number of non-lysosomal glycoproteins, including DNase I, Renin, LIF, and PoFut2 acquire low levels of the Man-6-P tag on their oligosaccharide chains. While the physiological significance of the low level Man-6-P modification of these proteins is not clear, it seems likely that extensive phosphorylation of these proteins by GlcNAc-1-PT would be counter-productive to a cell since the Man-6-P modified proteins would be segregated from the secretory pathway for delivery to the endosomal/lysosomal compartment. The data showing a 1.5-2 fold increase in the phosphorylation mediated by DS1 over the WT enzyme of DNase I, Renin, LIF, and PoFut2 indicates a role for spacer-1 in inhibiting phosphorylation of non-lysosomal proteins.

It was previously showed that deletion of the two Notch modules and the DMAP interaction domain (N1-D) virtually abolished the phosphorylation activity of the mutant GlcNAc-1-PT toward all lysosomal enzymes tested (3). In this regard, it is interesting that the spacer-1 deletion, when combined with the Notch1-DMAP deletion (S1-D), was able to restore low levels of phosphorylation of HEXB, GLA, and MANBA (14%, 13% and 5%, respectively of WT values). Since the N1-53 mutant does not require proteolytic processing for catalytic activity, it serves as a good control for assessing the impact of the spacer-1 deletion in the same context. This new construct, S1-53, which resembles bacterial sugar phosphate transferases (FIG. 6), was expressed at high levels, similar to those obtained with N1-53, and had similar activity toward αMM. However, the S1-53 construct increased phosphorylation of total soluble glycoproteins by almost 4-fold over WT, whereas the N1-S3 value was similar to WT. The S1-S3-mediated phosphorylation of the lysosomal enzymes HEXB, GLA, and MANBA was also increased compared N1-S3, as was the phosphorylation of the non-lysosomal glycoproteins proteins glycopepsinogen and the vWF A1A2A3 domains. The ability of the S1-S3 construct to phosphorylate non-lysosomal proteins that are not acted upon by the WT enzyme indicates that it can function in the absence of protein-docking sites, similar to bacterial sugar phosphate transferases.

Figure 5:
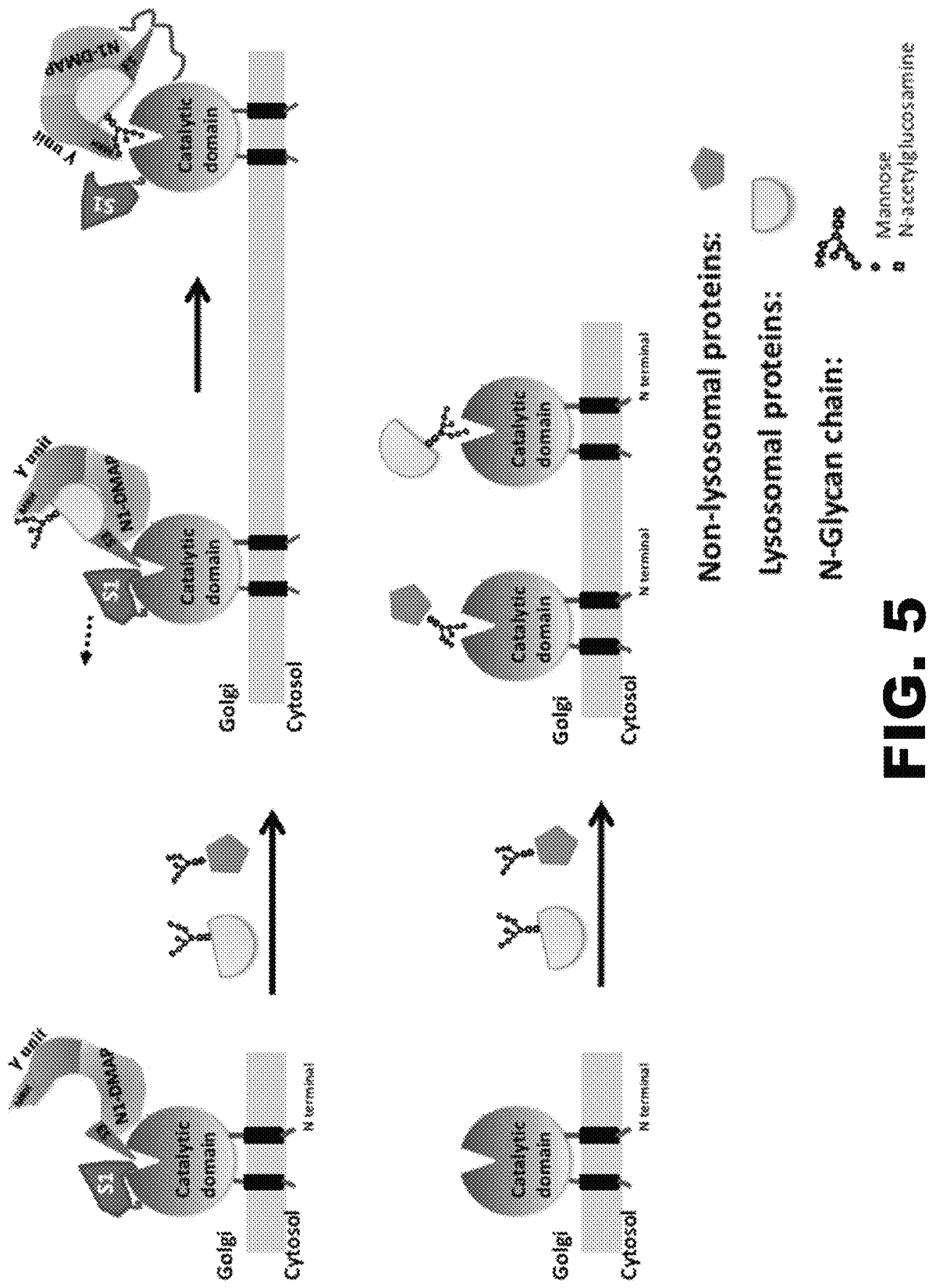
FIG. 5 depicts a model for GlcNAc-1-PT function. (Top) GlcNAc-1-PT, in the basal state, is unable to engage the glycan chains on substrate molecules since the spacer-1 domain (purple) interferes with the catalytic site formed by the four Stealth domains (pink). Binding of the lysosomal enzyme protein-docking site to the Notch modules/DMAP interaction domain (orange) induces a conformational change such that the spacer-1 domain is now displaced, allowing mannose residues of the lysosomal enzyme high-mannose glycans to enter the catalytic site and be phosphorylated. In some instances, the Man-6-P receptor homology domain of the γ subunit (green) will help guide the oligosaccharides toward the catalytic site. (Bottom) The minimal enzyme lacking the spacer-1 domain and the Notch modules/DMAP interaction domain is neither inhibited nor requires protein-docking sites on substrate molecules for phosphorylation. This enzyme is expressed at very high levels and able to phosphorylate all the soluble glycoproteins passing through the Golgi irrespective of their final destination.

Taken together, these findings provide support for the hypothesis that GlcNAc-1-PT α/β precursor acquired in the course of vertebrate evolution both positive (Notch modules and DMAP interaction domain) and negative (spacer-1) regulatory domains that serve to facilitate phosphorylation of lysosomal proteins while simultaneously negating the inherent capability of the enzyme to phosphorylate non-lysosomal glycoproteins. Based on these findings, we propose the following model to explain how GlcNAc-1-PT functions. In the basal state (FIG. 5A), the spacer-1 domain interferes with oligosaccharide engagement of the catalytic site formed by the four Stealth domains. Upon binding of the lysosomal enzyme protein docking site to the Notch modules and DMAP interaction domain, a conformational change occurs such that the spacer-1 domain is displaced, allowing mannose residues of the lysosomal enzyme high-mannose glycans to enter the catalytic site and be phosphorylated. In some instances, the mannose-6-phosphate receptor homology domain of the γ subunit will help guide the oligosaccharides toward the catalytic site. Weak-binding non-lysosomal glycoproteins such as DNase I may be unable to induce the conformational change required to displace spacer-1, limiting the extent of their phosphorylation. Upon deletion of spacer-1, phosphorylation of these proteins is increased. Non-lysosomal glycoproteins that totally lack the structural determinants for binding the Notch modules and DMAP interaction domain fail to be phosphorylated at all. Removal of spacer-1 together with the N1-S3 elements results in an enzyme that is highly expressed with full catalytic activity, allowing it to phosphorylate all the soluble glycoproteins passing through the Golgi (FIG. 5B).

Methods for Examples 1-4

Cell lines—The GNPTAB$^{-/-}$ HeLa cell line has been described in detail elsewhere (3). Cells were maintained in DMEM (Life Technologies) containing 0.11 g/L sodium pyruvate and 4.5 g/L glucose, supplemented with 10% (vol/vol) FBS (Atlanta Biologicals), 100,000 U/L penicillin, 100 mg/L streptomycin (Life Technologies) and 2 mM L-glutamine (Life Technologies).

DNA constructs—Human GNPTAB-V5/His in pcDNA6 has been described (11). The various α/β deletion constructs were made by either a 2-step overlap-extension (OE) PCR process wherein a PCR-generated restriction fragment encoding the deletion in question was swapped for the native cDNA within the same region. In order to generate the DS1 construct, a 0.5 kb gBlocks gene fragment was synthesized (IDT Inc.) that encoded the *D. discoideum* spacer-1 sequence together with the human Stealth1 and Stealth 2 sequences and utilized in the first step of the OE-PCR. Point mutations were generated by the QuikChange site-directed mutagenesis method and all sequences were confirmed to be correct by DNA sequencing.

The LIF cDNA construct was kindly provided by Richard Street (University of Georgia. Athens, Ga.) while the PoFut2-myc cDNA was a gift from Robert Haltiwanger (University of Georgia. Athens, Ga.). DNase I, glycopepsinogen, CathD-myc, α-GalA, and NPC2-myc have been described (3, 12, 21). Renin-HA cDNA was purchased from Addgene (Cambridge, Mass.), while the plasmid, vWF-A1A2A3-Strep-pCDNA6, was provided by J. Evan Sadler (Washington University School of Medicine, St. Louis, Mo.).

Immunofluorescence microscopy—To visualize the subcellular localization of WT α/β and the various mutants, the different constructs were transfected into GNPTAB$^{-/-}$ HeLa cells using Lipofectamine 3000 (Life Technologies) according to the manufacturer's protocol. 24 h post-transfection, the cells were fixed and the α/β subunits were detected with mouse anti-V5 monoclonal antibody (Life Technologies). The Golgi marker, GOLPH4, was detected with rabbit anti-GOLPH4 polyclonal antibody (Abcam), respectively. The processed cells were mounted in ProLong® Gold antifade mounting medium (Life Technologies), and the images were acquired with either an LSM880 confocal microscope (Carl Zeiss Inc.). Images were analyzed by Image J software (Fiji).

Western blotting—Proteins resolved by SDS-PAGE under reducing conditions were transferred to nitrocellulose membrane and detected with antibodies as indicated in the figure legends.

[2-$^3$H]Mannose labeling experiments for total soluble glycoproteins—Labeling experiments were performed with transfected GNPTAB$^{-/-}$ HeLa cells as follows: 48 h post-transfection, cells in 6-well plates were incubated with 10 μCi of [2-$^3$H]mannose (Perkin Elmer) for 2 h. Following the 2 h pulse, cells were rinsed twice with PBS and harvested, then resuspended in detergent-free buffer containing 25 mM Tris.Cl (pH 7.2) and 150 mM NaCl at 4° C. with a protease inhibitor cocktail (Life Technologies). Cell were lysed by sonication, then subjected to ultracentrifugation at 100,000×g for 1 h to separate the membrane proteins from the soluble fraction. 100 μl of the soluble fraction was then incubated with purified CI-MPR that was covalently conjugated to Cyanogen bromide-activated-Sepharose 4B in order to pellet the mannose-phosphorylated glycoproteins, while 10 μl of the soluble fraction was precipitated by 1.5% phosphotungstic acid to obtain total [2-$^3$H]mannose label incorporation into the soluble proteins. This method allowed for accurate quantification of all the mannose labeled glycoproteins that were phosphorylated by either WT or mutant GlcNAc-1-PT.

[2-$^3$H]Mannose labeling experiments for lysosomal enzymes—Labeling experiments were performed with transfected GNPTAB$^{-/-}$ HeLa cells as follows: 48 h post-transfection, cells in 60-mm tissue culture plates were incubated with 50-150 μCi of [2-$^3$H]mannose (Perkin Elmer) for 2 h, followed by the addition of complete medium containing 5 mM glucose, 5 mM mannose and 10 mM NH4Cl to stop mannose uptake and induce secretion. The cells were incubated for an additional 3 h before the media was collected. In several experiments, cell extracts were prepared and subjected to Western blotting for β subunit content to confirm that the constructs were being expressed at comparable levels.

Immunoprecipitation and oligosaccharide analysis—Acid hydrolases secreted into the media were immunoprecipitated, and oligosaccharides isolated and analyzed essentially as described in detail previously (23). For the CathD-myc, NPC2-myc, PoFut2-myc and Renin-HA experiments, 20 μl anti-myc monoclonal antibody (Santa Cruz Biotechnology) or 5 μl anti-HA monoclonal antibody (Sigma-Aldrich) was pre-bound to 100 μl Protein G-agarose-PLUS beads (Santa Cruz Biotechnology) prior to immunoprecipitation of labeled lysosomal hydrolases from the media. In the case of GLA, DNase I, and LIF, the secreted enzymes were immunoprecipitated with Protein G-agarose-PLUS beads pre-bound to anti-β-Gal antibody (Amicus Therapeutics), and rProteinA-agarose beads (RepliGen) pre-bound to anti-DNase I antibody (Sigma, St. Louis, Mo.), or anti-LIF antibody (generously provided by Frederic Blanchard, University of Nantes, Nantes, France). Immunoprecipitated material was treated with Endo H (NEB) and filtered with Ultracel-10K (EMD Millipore). The filtrate containing neutral and phosphorylated high mannose glycans was treated with mild acid to remove any N-acetylglucosamine residues still attached to the phosphate moieties and applied to a QAE-column matrix to separate the oligosaccharides bearing zero, one or two Man-6-P residues. The retentate containing Endo H-resistant complex oligosaccharides was treated with Pronase (Roche Diagnostics) and fractionated on ConA-sepharose 4B (GE Healthcare). The [2-$^3$H]-mannose content of each fraction was determined and the percent phosphorylation was calculated as described (23). In all cases, values obtained with the mock transfection were subtracted.

References for Examples 1-4

1. Kornfeld S (1986) Trafficking of lysosomal enzymes in normal and disease states. *The Journal of clinical investigation* 77(1):1-6.
2. Reitman M L & Kornfeld S (1981) Lysosomal enzyme targeting. N-Acetylglucosaminylphosphotransferase selectively phosphorylates native lysosomal enzymes. *The Journal of biological chemistry* 256(23):11977-11980.

3. van Meel E, et al. (2016) Multiple Domains of GlcNAc-1-phosphotransferase Mediate Recognition of Lysosomal Enzymes. *The Journal of biological chemistry* 291(15): 8295-8307.
4. Bao M, Booth J L, Elmendorf B J, & Canfield W M (1996) Bovine UDP-N-acetylglucosamine:lysosomal-enzyme N-acetylglucosamine-1-phosphotransferase. I. Purification and subunit structure. *The Journal of biological chemistry* 271(49):31437-31445.
5. Kudo M, et al. (2005) The alpha- and beta-subunits of the human UDP-N-acetylglucosamine:lysosomal enzyme N-acetylglucosamine-1-phosphotransferase [corrected] are encoded by a single cDNA. *The Journal of biological chemistry* 280(43):36141-36149.
6. Marschner K, Kollmann K, Schweizer M, Braulke T, & Pohl S (2011) A key enzyme in the biogenesis of lysosomes is a protease that regulates cholesterol metabolism. *Science* 333(6038):87-90.
7. Sperisen P, Schmid C D, Bucher P, & Zilian O (2005) Stealth proteins: in silico identification of a novel protein family rendering bacterial pathogens invisible to host immune defense. *PLoS computational biology* 1(6):e63.
8. De Pace R, et al. (2015) Subunit interactions of the disease-related hexameric GlcNAc-1-phosphotransferase complex. *Human molecular genetics* 24(23):6826-6835.
9. Hay B A, et al. (2007) Aminopyrrolidineamide inhibitors of site-1 protease. *Bioorganic & medicinal chemistry letters* 17(16):4411-4414.
10. Elagoz A, Benjannet S, Mammarbassi A, Wickham L, & Seidah N G (2002) Biosynthesis and cellular trafficking of the convertase SKI-1/S1P: ectodomain shedding requires SKI-1 activity. *The Journal of biological chemistry* 277(13):11265-11275.
11. Qian Y, et al. (2015) Analysis of Mucolipidosis II/III GNPTAB Missense Mutations Identifies Domains of UDP-GlcNAc:lysosomal Enzyme GlcNAc-1-phosphotransferase Involved in Catalytic Function and Lysosomal Enzyme Recognition. *The Journal of biological chemistry* 290(5):30453056.
12. Nishikawa A, Nanda A, Gregory W, Frenz J, & Kornfeld S (1999) Identification of amino acids that modulate mannose phosphorylation of mouse DNase I, a secretory glycoprotein. *The Journal of biological chemistry* 274(27):19309-19315.
13. Blanchard F, et al. (1998) The mannose 6-phosphate/insulin-like growth factor II receptor is a nanomolar affinity receptor for glycosylated human leukemia inhibitory factor. *The Journal of biological chemistry* 273(33):20886-20893.
14. Faust P L, Chirgwin J M, & Kornfeld S (1987) Renin, a secretory glycoprotein, acquires phosphomannosyl residues. *The Journal of cell biology* 105(5):1947-1955.
15. Sleat D E, Zheng H, Qian M, & Lobel P (2006) Identification of sites of mannose 6-phosphorylation on lysosomal proteins. *Molecular & cellular proteomics: MCP* 5(4):686-701.
16. Qian Y, Flanagan-Steet H, van Meel E, Steet R, & Kornfeld S A (2013) The DMAP interaction domain of UDP-GlcNAc:lysosomal enzyme N-acetylglucosamine-1-phosphotransferase is a substrate recognition module. *Proceedings of the National Academy of Sciences of the United States of America* 110(25):10246-10251.
17. Sleat D E, et al. (2013) Extending the mannose 6-phosphate glycoproteome by high resolution/accuracy mass spectrometry analysis of control and acid phosphatase 5-deficient mice. *Molecular & cellular proteomics: MCP* 12(7):1806-1817.
18. Lang L, Reitman M, Tang J, Roberts R M, & Kornfeld S (1984) Lysosomal enzyme phosphorylation. Recognition of a protein-dependent determinant allows specific phosphorylation of oligosaccharides present on lysosomal enzymes. *The Journal of biological chemistry* 259(23):14663-14671.
19. Serrano P, Geralt, M., Wuthrich, K. (2015) NMR structure of the 140-315 fragment of the N-acetylglucosamine-1-phosphate transferase, alpha and beta subunits.
20. Velho R V, et al. (2015) Analyses of disease-related GNPTAB mutations define a novel GlcNAc-1-phosphotransferase interaction domain and an alternative site-1 protease cleavage site. *Human molecular genetics* 24(12):3497-3505.
21. Steet R, Lee W S, & Kornfeld S (2005) Identification of the minimal lysosomal enzyme recognition domain in cathepsin D. *The Journal of biological chemistry* 280(39):33318-33323.
22. Valenzano K J, Remmler J, & Lobel P (1995) Soluble insulin-like growth factor II/mannose 6-phosphate receptor carries multiple high molecular weight forms of insulin-like growth factor II in fetal bovine serum. *The Journal of biological chemistry* 270(27):16441-16448.
23. Dustin M L, Baranski T J, Sampath D, & Kornfeld S (1995) A novel mutagenesis strategy identifies distantly spaced amino acid sequences that are required for the phosphorylation of both the oligosaccharides of procathepsin D by N-acetylglucosamine 1-phosphotransferase. *The Journal of biological chemistry* 270(1):170-179.

Example 5. Method for Producing Highly Phosphorylated Lysosomal Enzymes for Enzyme Replacement Therapy Enzyme Replacement Therapy (ERT) is currently the major form of treatment for a number of lysosomal storage diseases, although its efficacy varies among the individual disorders [1]. Most of these inherited disorders arise from the lack of activity of a single lysosomal enzyme which leads to the accumulation of the material normally degraded by the enzyme. The buildup of the storage material in the lysosome eventually results in cell and organ dysfunction. The goal of ERT is to introduce sufficient amounts of normal enzyme into the lysosomes of the defective cells to clear the storage material and restore lysosome function. This form of therapy was first used in patients with Type 1 Gaucher disease who lack acid 3-glucocebrosidase activity and accumulate glucosylceramide primarily in macrophage type cells [2]. The replacement enzyme, containing N-linked glycans with terminal mannose residues, is infused intravenously and taken up by macrophages via cell surface mannose receptors. The endocytosed enzyme is then transported via endosomes to lysosomes where it functions with good clinical results in this disorder [3].

Since most cell types lack mannose receptors, the replacement enzymes used to treat lysosomal storage disorders that involve cell types other than macrophages utilize binding to mannose 6-phosphate (Man-6-P) receptors at the cell surface for subsequent delivery to lysosomes. These enzymes are purified from the secretions of mammalian cells, mostly Chinese Hamster Ovary cells, engineered to produce high levels of the enzyme of interest. This approach is dependent upon the ability of the endogenous GlcNAc-1-phosphotransferase to phosphorylate mannose residues of the N-glycans of the expressed lysosomal enzyme. Some of the replacement enzymes produced by this technique are highly phosphorylated and bind well to the Man-6-P receptors. Others, however, are poorly phosphorylated, limiting their effectiveness in ERT. This includes the Pompe disease enzyme (acid α-glucosidase, GAA) and the alpha-mannosidosis enzyme (lysosomal acid α-mannosidase, LAMAN) [4, 5].

Figure 12A:
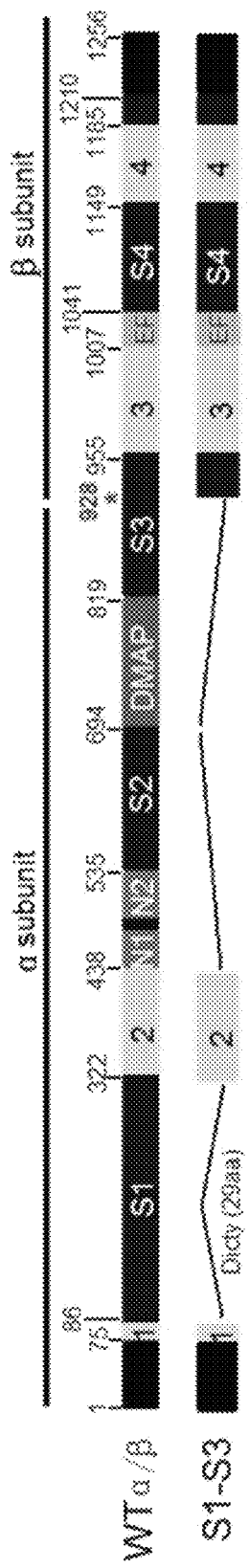
FIG. 12A, FIG. 12B and FIG. 12C depict a schematic and graphs showing the expression of a minimal GlcNAc-1-phosphotransferase and analysis of enzyme activity.

The activity of the endogenous GlcNAc-1-phosphotransferase may be insufficient to effectively phosphorylate the high levels of GAA and LAMAN being synthesized by the producing cells. To examine this possibility, Expi293F or cation-independent mannose 6-phosphate receptor (CI-MPR) negative mouse D9 L cells were co-transfected with plasmids encoding a lysosomal enzyme of interest along with the cDNA for the GlcNAc-1-phosphotransferase α/β precursor. While GlcNAc-1-phosphotransferase is an α2β2γ2 hexamer encoded by two genes (GNPTAB and GNPTG), the α/β subunits are able to phosphorylate most lysosomal enzymes in the absence of γ [6]. In addition, a truncated α/β precursor (S1-S3) that lacks a number of the a subunit elements while retaining the catalytic "Stealth" domains was also tested (FIG. 12A). This truncated enzyme is expressed at very high levels resulting in a 20-fold greater catalytic activity than occurs with the WT enzyme [7].

Figure 12B:
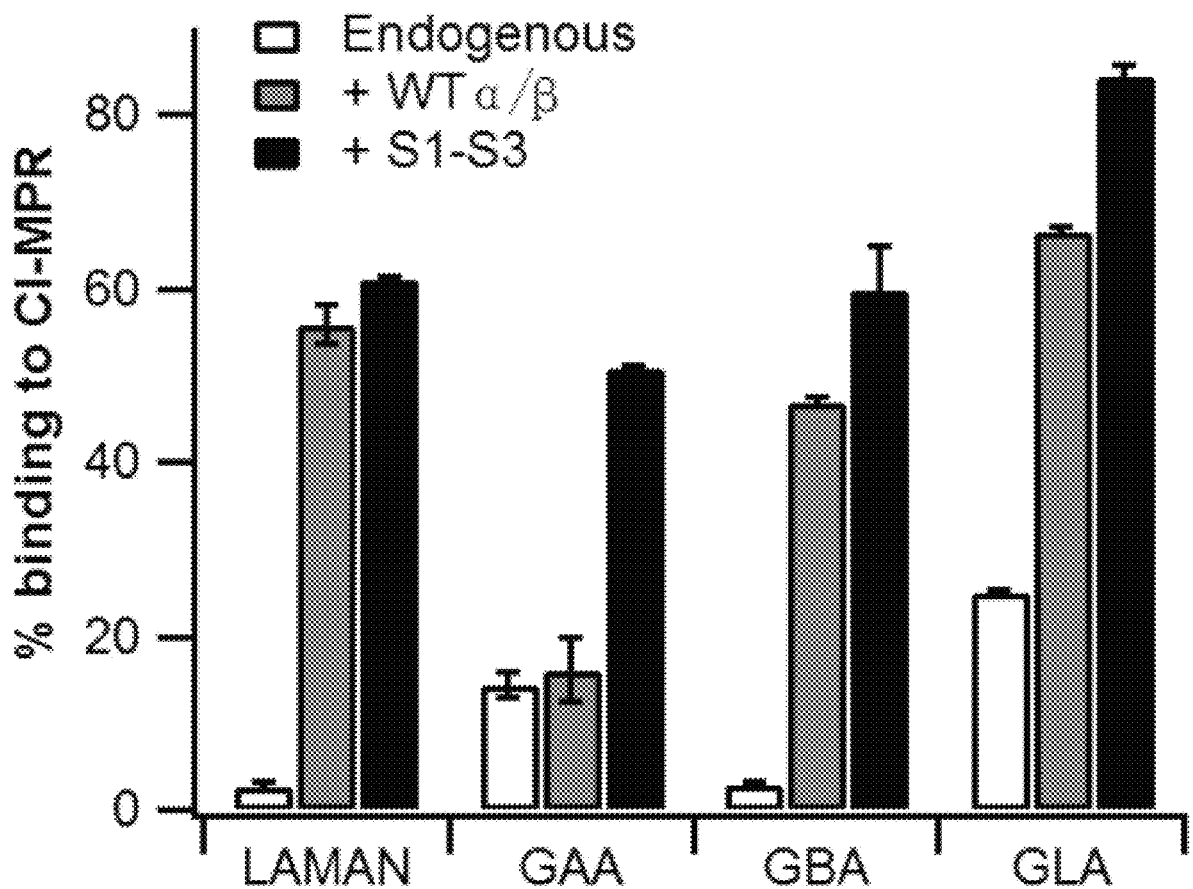
Figure 12C:
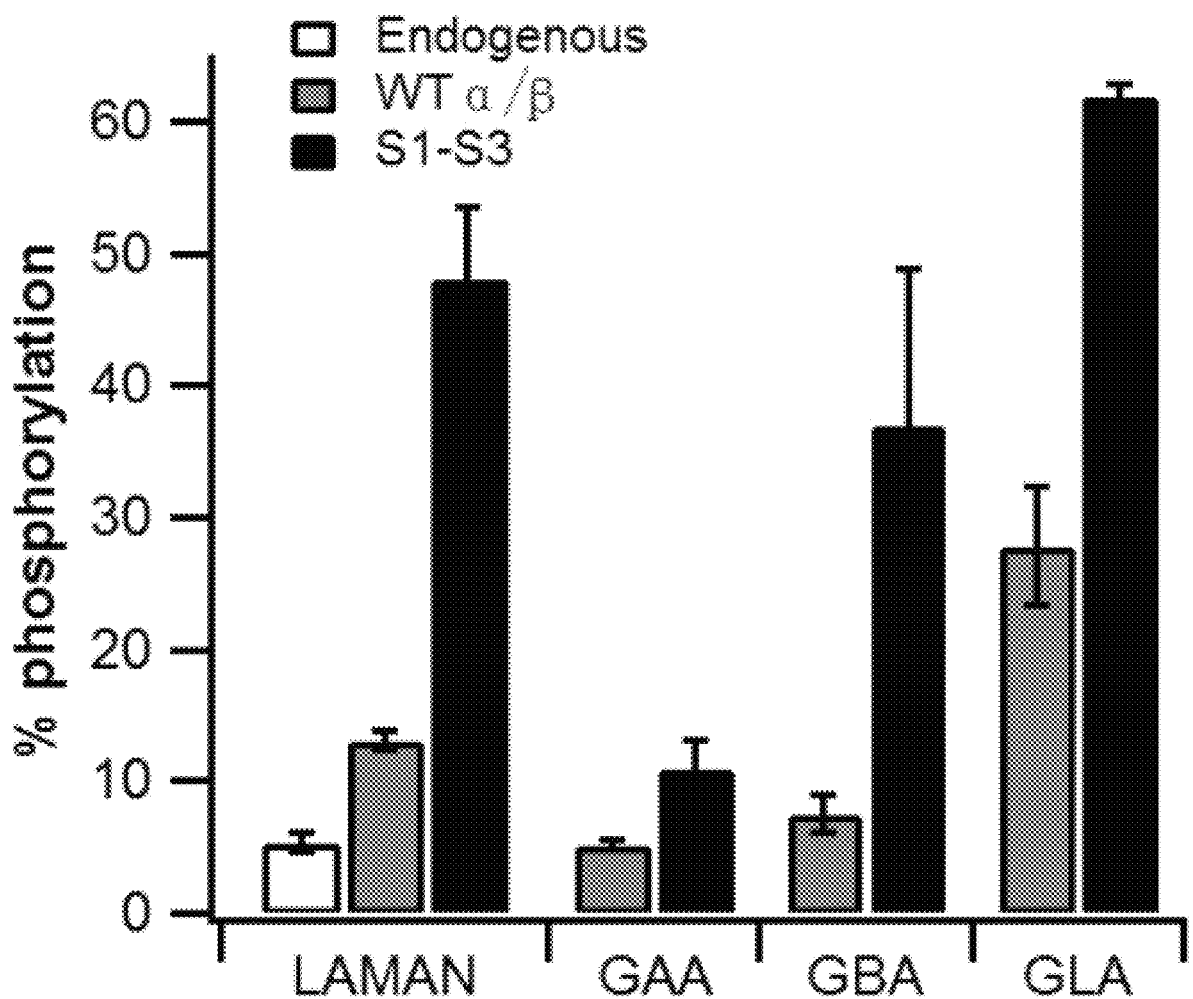

The binding of four lysosomal enzymes secreted by the transfected cells to CI-MPR-beads is shown in FIG. 12B. Increased binding, in this case, reflects a higher degree of phosphorylation of these enzymes. In all instances, the enzyme secreted by cells co-transfected with the truncated α/β precursor bound to the CI-MPR-beads to a much greater extent than observed with enzyme expressed alone in the cells. The effect of co-transfection with the WT α/β precursor on the lysosomal enzyme binding to the CI-MPR-beads was variable, ranging from minimal stimulation of GAA binding to 12-fold enhanced binding in the case of LAMAN. To look more directly at the effects of the α/β precursor constructs on lysosomal enzyme phosphorylation, HeLa cells with a CRISPR-Cas9 inactivated GNPTAB gene [8] were transfected with the various plasmids and then incubated with [2-$^3$H] mannose for 1 hr to label the N-linked glycans of the lysosomal enzymes. As a control, the parental HeLa cells with active endogenous GlcNAc-1-phosphotransferase were transfected with only the plasmids encoding the lysosomal enzymes. Following a 4 h chase in the presence of NH4C1 to stimulate secretion of the labeled enzyme, the media was harvested and the lysosomal enzyme of interest was immunoprecipitated. The immunoprecipitates were then analyzed for their content of high mannose N-linked glycans with one or two Man-6-P residues [8, 9]. These experiments showed that the truncated α/β precursor stimulated mannose phosphorylation at various levels over the parental HeLa cells, depending on the lysosomal enzyme (FIG. 12C). Further, the truncated enzyme increased the formation of glycans with two Man-6-P residues (Table 2). This is important since glycans with 2 Man-6-P residues bind with much higher affinity to the CI-MPR than glycans with only 1 Man-6-P residue [10]. The WT α/β precursor also stimulated Man-6-P formation, but to a lesser extent than observed with the mutant α/p.

The impact of the increased Man-6-P content of the various lysosomal enzymes on their uptake by HeLa cells is shown in Table 1. With the exception of GAA, the enzymes secreted by cells co-transfected with plasmids encoding either WT or truncated α/β precursor were internalized many fold better than enzyme secreted by cells utilizing only the endogenous GlcNAc-1-phosphotransferase. Most of the uptake was blocked by the presence of 5 mM Man-6P in the media, showing that the uptake is mediated by the Man-6-P receptor. The results with LAMAN were particularly striking, with Man-6-P-inhibitable uptake being stimulated by 130- to 153-fold. In the case of GAA, the Man-6-P-dependent uptake of enzyme secreted by cells co-transfected with the truncated α/β precursor was 2.6-fold greater than GAA secreted by cells co-transfected with WT α/β precursor or only expressing the endogenous GlcNAc-1-phosphotransferase.

These findings establish that lysosomal enzyme phosphorylation can be substantially increased by co-transfection with either WT or truncated α/8 precursor of GlcNAc-1-phosphotransferase. The enhanced phosphorylation increases binding to the CI-MPR and uptake by cells. This effect even occurs with lysosomal enzymes such as GalA that are well phosphorylated by the endogenous GlcNAc-1-phosphotransferase. But most important is the finding that this method enhances the phosphorylation and uptake of LAMAN and GAA, two lysosomal enzymes that are poorly phosphorylated by endogenous GlcNAc-1-phosphotransferase. Enzymes prepared by this method have the potential to significantly improve their usefulness in ERT. In addition to providing better cell uptake, these preparations may allow lower doses to be administered to patients, perhaps at less frequent intervals. The method should be applicable to the production of lysosomal enzymes for other lysosomal storage diseases that may be amenable to ERT. In addition, the production of GBA containing high levels of Man-6-P offers the opportunity to restore enzyme activity to cell types in patients with Gaucher disease that lack the mannose receptor. This might serve to provide additional benefit to the current therapy which is directed specifically to macrophages.

Methods for Example 5

Cell lines—Expi293F cells are from Life Technologies. These cells were grown in suspension in Expi293 expression medium (Life Technologies). The GNPTAB$^{-/-}$ HeLa cell line has been described in detail elsewhere [8]. Parental and GNPTAB$^{-/-}$ HeLa cell were maintained as a monolayer in DMEM (Life Technologies) containing 0.11 g/L sodium pyruvate and 4.5 g/L glucose, supplemented with 10% (vol/vol) FBS (Atlanta Biologicals), 100,000 U/L penicillin, 100 mg/L streptomycin (Life Technologies) and 2 mM L-glutamine (Life Technologies). CI-MPR negative mouse L-cells (D9 cell line) have been described [11]. D9 cells were maintained as a monolayer in α-MEM (Life Technologies) containing 100,000 U/L penicillin and 100 mg/L streptomycin (Life Technologies).

DNA constructs— Human GNPTAB-V5/His and the S1-S3 deletion mutant in pcDNA6 has been described [7]. The LAMAN-myc-Flag cDNA was purchased from Origene while the GAA cDNA was a kind gift of Eline van Meel (Leiden University, The Netherlands). The GBA and GLA cDNAs were generously provided by Amicus Therapeutics.

CI-MPR affinity chromatography and enzyme assays— Soluble bovine CI-MPR was purified from fetal bovine serum and covalently conjugated to Cyanogen bromide-activated-Sepharose 4B (Sigma-Aldrich) as described [12]. Media from 2-day transfected Expi293F cells or mouse D9 cells were incubated with the CI-MPR beads at 4° C. for 1 h to bind the phosphorylated lysosomal enzymes. The beads were then sedimented, washed with buffer (25 mM Tris-Cl, pH7.2, 150 mM NaCl and 1% Triton-X 100), and assayed for lysosomal enzyme activity as described [13]. The amount of the starting enzyme recovered on the beads was calculated.

Cell uptake of lysosomal enzymes—Parental HeLa cells were plated on a 12-well plate at around 80% density one day prior to the cell uptake experiment. Media containing each enzyme from the producing cells was added to the parental HeLa cells in a final volume of 500 µl. For competition experiments, Man-6-P was added to a final concentration of 5 mM. Cells were incubated for an additional 24 h, following which media and cells were collected separately. Cells were rinsed twice with PBS, then lysed in 25 mM Tris-Cl, pH 7.2, 150 mM NaCl, 1% Triton-X 100, and protease inhibitor cocktail (Life Technologies). The media and lysed cells were centrifuged at 20,000×g, and the activity of the enzyme in the supernatant of the media and cell lysate was assayed.

[2-$^3$H]Mannose labeling experiments for lysosomal enzymes—Labeling experiments were performed with transfected GNPTAB$^{-/-}$ parental HeLa cells as follows: 48 h post-transfection, cells in 60-mm tissue culture plates were incubated with 50-150 µCi of [2-$^3$H]mannose (Perkin Elmer) for 2 h, followed by the addition of complete medium containing 5 mM glucose, 5 mM mannose and 10 mM NH4Cl to stop mannose uptake and induce secretion. The cells were incubated for an additional 3 h before the media was collected for analysis.

Immunoprecipitation and oligosaccharide analysis—Acid hydrolases secreted into the media were immunoprecipitated, and oligosaccharides isolated and analyzed essentially as described in detail previously [9]. Since the LAMAN, GAA and GBA cDNAs were appended with a myc-tag, 20 µl anti-myc monoclonal antibody (Santa Cruz Biotechnology) was pre-bound to 100 µl Protein G-agarose-PLUS beads (Santa Cruz Biotechnology) prior to immunoprecipitation of labeled lysosomal hydrolases from the media. In the case of GLA, the secreted enzyme was immunoprecipitated with Protein G-agarose-PLUS beads pre-bound to anti-p-Gal antibody (Amicus Therapeutics). Immunoprecipitated material was treated with Endo H (NEB) and filtered with Ultracel-10K (EMD Millipore). The filtrate containing neutral and phosphorylated high mannose glycans was treated with mild acid to remove any N-acetylglucosamine residues still attached to the phosphate moieties and applied to a QAE-column matrix to separate the oligosaccharides bearing zero, one or two Man-6-P residues. The retentate containing Endo H-resistant complex oligosaccharides was treated with Pronase (Roche Diagnostics) and fractionated on ConA-sepharose 4B (GE Healthcare). The [2-$^3$H]-mannose content of each fraction was determined and the percent phosphorylation was calculated as described [9].

TABLE 1

Cell uptake of lysosomal enzymes phosphorylated with endogenous GlcNAc-1-phosphotransferase or overexpressed WT enzyme or the S1-S3 mutant. Uptake experiments were performed either in the absence of Man-6-P, or with 5 mM Man-6-P to competitively inhibit uptake of the phosphorylated enzymes.

| Enzyme | PTase | Total U Added | Man-6-P | % uptake* | M6PR Dependent | Fold Increase |
|---|---|---|---|---|---|---|
| LAMAN | Endogenous | 670 | − | 0.76 ± 0.23 | 0.14 | |
|  |  |  | + | 0.62 ± 0.27 |  |  |
|  | WT α/β | 359 | − | 24.70 ± 1.34 | 21.5 | 153 X |
|  |  |  | + | 3.20 ± 0.77 |  |  |
|  | S1-S3 | 530 | − | 22.46 ± 4.07 | 18.2 | 130 X |
|  |  |  | + | 4.3 ± 1.19 |  |  |
| GAA | Endogenous | 5.7 | − | 4.05 ± 0.46 | 3.8 |  |
|  |  |  | + | 0.22 ± 0.42 |  |  |
|  | WT α/β | 3.8 | − | 3.31 ± 1.13 | 2.9 | 0.8 X |
|  |  |  | + | 0.44 ± 1.18 |  |  |
|  | S1-S3 | 3.2 | − | 12.79 ± 0.90 | 8.8 | 2.6 X |
|  |  |  | + | 2.99 ± 1.59 |  |  |
| GBA | Endogenous | 2.7 | − | 10.74 ± 1.94 | 5.1 |  |
|  |  |  | + | 5.65 ± 1.51 |  |  |
|  | WT α/β | 2.3 | − | 46.73 ± 4.00 | 37.4 | 7.3 X |
|  |  |  | + | 9.37 ± 1.26 |  |  |
|  | S1-S3 | 2.8 | − | 40.74 ± 11.53 | 41.1 | 8.0 X |
|  |  |  | + | 8.87 ± 4.21 |  |  |
| GLA | Endogenous | 194 | − | 2.72 ± 0.91 | 1.7 |  |
|  |  |  | + | 1.00 ± 0.11 |  |  |
|  | WT α/β | 141 | − | 9.53 ± 0.11 | 8.2 | 4.8 X |
|  |  |  | + | 1.30 ± 0.13 |  |  |
|  | S1-S3 | 237 | − | 7.01 ± 0.69 | 8.1 | 3.5 X |
|  |  |  | + | 0.95 ± 0.11 |  |  |

Note:
1U = 1 nmol 4-Methylumbelliferone released per hour
*% uptake per 200 ug cell protein in 24 hour

TABLE 2

Distribution of high mannose glycans with one or two Man-6-P residues present on lysosomal enzymes. The data presented in FIG. 12C is further broken down to show the content of glycans with 1 or 2 Man-6-P residues among the lysosomal enzymes acted upon by the endogenous GlcNAc-1-phosphotransferase or the overexpressed WT α/β precursor or the S1-S3 deletion mutant.

| Enzyme | PTase | % Oligosaccharide phosphorylation | | |
|---|---|---|---|---|
|  |  | HM + 1PM | HM + 2PM | Total |
| LAMAN | Endogenous | 4.5 | 1.0 | 5.5 |
|  | WT | 9.7 | 3.4 | 13.1 |
|  | S1-S3 | 24.3 | 23.9 | 48.2 |

TABLE 2-continued

Distribution of high mannose glycans with one or two Man-6-P residues present on lysosomal enzymes. The data presented in FIG. 12C is further broken down to show the content of glycans with 1 or 2 Man-6-P residues among the lysosomal enzymes acted upon by the endogenous GlcNAc-1-phosphotransferase or the overexpressed WT α/β precursor or the S1-S3 deletion mutant.

| Enzyme | PTase | % Oligosaccharide phosphorylation | | |
|---|---|---|---|---|
| | | HM + 1PM | HM + 2PM | Total |
| GAA | WT | 4.2 | 1.1 | 5.2 |
| | S1-S3 | 8.3 | 2.7 | 11.0 |
| GBA | WT | 6.4 | 1.2 | 7.6 |
| | S1-S3 | 27.2 | 9.7 | 36.9 |
| GLA | WT | 23.7 | 4.0 | 27.8 |
| | S1-S3 | 49.6 | 12.4 | 62.0 |

HM—High Mannose oligosaccharide
PM—phosphomonoester

References for Example 5

1. Lachmann, R. H., *Enzyme replacement therapy for lysosomal storage diseases*. Curr Opin Pediatr, 2011. 23(6): p. 588-93.
2. Barton, N. W., et al., *Replacement therapy for inherited enzyme deficiency—macrophage-targeted glucocerebrosidase for Gaucher's disease*. N Engl J Med, 1991. 324(21): p. 1464-70.
3. Weinreb, N.J., et al., *Long-term clinical outcomes in type 1 Gaucher disease following 10 years of imiglucerase treatment*. J Inherit Metab Dis, 2013. 36(3): p. 543-53.
4. McVie-Wylie, A. J., et al., *Biochemical and pharmacological characterization of different recombinant acid alpha-glucosidase preparations evaluated for the treatment of Pompe disease*. Mol Genet Metab, 2008. 94(4): p. 448-55.
5. Roces, D. P., et al., *Efficacy of enzyme replacement therapy in alpha-mannosidosis mice: a preclinical animal study*. Hum Mol Genet, 2004. 13(18): p. 1979-88.
6. Qian, Y., et al., Functions of the alpha, beta, and gamma subunits of *UDP-GlcNAc:lysosomal enzyme N-acetylglucosamine-1-phosphotransferase*. J Biol Chem, 2010. 285 (5): p. 3360-70.
7. Lin Liu, W.-S. L., Balraj Doray, and Stuart Kornfeld, *Regulation of Lysosmal Enzyme Phosphorylation: Role of the Spacer-1 Domain of GlcNAc-1-Phosphotransferase*. manuscript in preparation.
8. van Meel, E., et al., *Multiple Domains of GlcNAc-1-phosphotransferase Mediate Recognition of Lysosomal Enzymes*. J Biol Chem, 2016. 291(15): p. 8295-307.
9. Dustin, M. L., et al., *A novel mutagenesis strategy identifies distantly spaced amino acid sequences that are required for the phosphorylation of both the oligosaccharides of procathepsin D by N-acetylglucosamine 1-phosphotransferase*. J Biol Chem, 1995. 270(1): p. 170-9.
10. Tong, P. Y., W. Gregory, and S. Kornfeld, *Ligand interactions of the cation-independent mannose 6-phosphate receptor. The stoichiometry of mannose 6-phosphate binding*. J Biol Chem, 1989.264(14): p. 7962-9.
11. Gabel, C. A. and S. A. Foster, *Lysosomal enzyme trafficking in mannose 6-phosphate receptor-positive mouse L-cells: demonstration of a steady state accumulation of phosphorylated acid hydrolases*. J Cell Biol, 1986. 102(3): p. 943-50.
12. Valenzano, K. J., J. Remmler, and P. Lobel, *Soluble insulin-like growth factor II/mannose 6-phosphate receptor carries multiple high molecular weight forms of insulin-like growth factor II in fetal bovine serum*. J Biol Chem, 1995. 270(27): p. 16441-8.
13. Qian, Y., et al., *Analysis of Mucolipidosis GNPTAB Missense Mutations Identifies Domains of UDP-GlcNAc: lysosomal Enzyme GlcNAc-1-phosphotransferase Involved in Catalytic Function and Lysosomal Enzyme Recognition*. J Biol Chem, 2015. 290(5): p. 3045-56.

What is claimed is:

1. A method to increase binding of a protein of interest to cell surface mannose 6-phosphate receptor (Man-6-P), the method comprising expressing a modified GlcNAc-1-PT α/β subunit in a cell, wherein the modified GlcNAc-1-PT α/β subunit comprises an internal deletion of amino acids with reference to full-length human GlnNAc-1-PT α/β subunit having the sequence of SEQ ID NO:1, wherein amino acids 86 to 322 and amino acids 438 to 928 are deleted, and wherein the increased binding of a protein of interest to cell surface mannose 6-phosphate receptor (Man-6-P) is compared to the binding of a protein of interest to cell surface mannose 6-phosphate receptor (Man-6-P) in a cell expressing endogenous GlcNAc-1-PT α/β subunit.

2. The method of claim 1, wherein the protein of interest is a lysosomal protein.

3. The method of claim 2, wherein the lysosomal protein is selected from the group consisting of β-glucocebrosidase (GBA), GalA, Cathepsin D (CathD), Niemann-Pick disease type C2 (NPC2), β-hexosaminidase (HEXB), α-Galactosidase (GLA), β-Mannosidase (MANBA), alpha-L-idurnoidase, iduronate sulfatase, arylsulfatase B, acid α-glucosidase (GAA), and lysosomal acid a mannosidase (LAMAN).

4. The method of claim 1, wherein the protein of interest is a non-lysosomal protein.

5. The method of claim 4, wherein the non-lysosomal protein is selected from the group consisting of DNaseI, Renin, leukemia inhibitory factor (LIF), protein O-fucosyltransferase 2 (PoFUT2), glycopepsinogen (GP), and the von Willebrand factor A1A2A3 domains.

6. The method of claim 1, wherein the protein of interest is selected from the group consisting of the Pompe disease enzyme (acid a-glucosidase, GAA) and the alpha-mannosidosis enzyme (lysosomal acid a-mannosidase, LAMAN).

7. The method of claim 1, wherein the amount of glycans with 2 Man-6-P residues is increased relative to GlcNAc-1-PT α/β subunit.

8. The method of claim 1, wherein the phosphorylation of the protein of interest is enhanced.

* * * * *